US010836820B2

(12) United States Patent
Horlick et al.

(10) Patent No.: US 10,836,820 B2
(45) Date of Patent: *Nov. 17, 2020

(54) METHOD OF TREATING INFLAMMATORY DISORDER WITH ANTIBODIES DIRECTED AGAINST INTERLEUKIN-33 (IL-33)

(71) Applicant: AnaptysBio, Inc., San Diego, CA (US)

(72) Inventors: Robert A. Horlick, San Diego, CA (US); David J. King, Encinitas, CA (US); Andrew John McKnight, San Diego, CA (US)

(73) Assignee: AnaptysBio, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,476

(22) Filed: Jul. 23, 2018

(65) Prior Publication Data

US 2018/0346562 A1 Dec. 6, 2018

Related U.S. Application Data

(62) Division of application No. 15/110,724, filed as application No. PCT/US2015/010785 on Jan. 9, 2015, now Pat. No. 10,059,764.

(60) Provisional application No. 61/925,946, filed on Jan. 10, 2014.

(51) Int. Cl.
*A61K 39/395* (2006.01)
*C07K 16/24* (2006.01)

(52) U.S. Cl.
CPC ........ *C07K 16/244* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,828,981 A | 5/1989 | Maggio | |
| 5,122,464 A | 6/1992 | Wilson et al. | |
| 5,464,758 A | 11/1995 | Gossen et al. | |
| 5,770,359 A | 6/1998 | Wilson et al. | |
| 5,814,618 A | 9/1998 | Bujard et al. | |
| 7,112,715 B2 | 9/2006 | Chambon et al. | |
| 7,560,530 B1 | 7/2009 | Chackerian et al. | |
| 7,915,388 B2 | 3/2011 | Wu et al. | |
| 8,119,771 B2 | 2/2012 | Martin | |
| 8,147,817 B2 | 4/2012 | Lee | |
| 8,187,596 B1 | 5/2012 | Chackerian et al. | |
| 8,383,778 B2 | 2/2013 | Hsieh et al. | |
| 8,568,992 B2 | 10/2013 | Walker et al. | |
| 8,604,177 B2 | 12/2013 | Wu et al. | |
| 8,841,417 B2 | 9/2014 | Wu et al. | |
| 8,999,331 B2 | 4/2015 | Hsieh et al. | |
| 9,090,694 B2 | 7/2015 | Duffy et al. | |
| 9,212,227 B2 | 12/2015 | Duffy et al. | |
| 9,382,318 B2 | 7/2016 | Smith et al. | |
| 9,409,896 B2 | 8/2016 | Burak et al. | |
| 9,447,183 B2 | 9/2016 | Wu et al. | |
| 9,447,184 B2 | 9/2016 | Wu et al. | |
| 9,453,072 B2 | 9/2016 | Murphy et al. | |
| 9,592,293 B2 | 3/2017 | Wu et al. | |
| 9,611,307 B2 | 4/2017 | Girard et al. | |
| 9,637,535 B2 | 5/2017 | Murphy et al. | |
| 10,059,764 B2 | 8/2018 | Horlick et al. | |
| 2008/0166352 A1 | 7/2008 | Siu et al. | |
| 2009/0041718 A1 | 2/2009 | Schmitz et al. | |
| 2009/0093024 A1 | 4/2009 | Bowers et al. | |
| 2010/0008851 A1 | 1/2010 | Nicolaides et al. | |
| 2010/0260705 A1 | 10/2010 | Martin | |
| 2010/0260770 A1 | 10/2010 | Coyle | |
| 2011/0287485 A1 | 11/2011 | Bowers et al. | |
| 2012/0156194 A1 | 6/2012 | Arron et al. | |
| 2012/0207752 A1 | 8/2012 | Chackerian et al. | |
| 2012/0263709 A1 | 10/2012 | Rankin et al. | |
| 2013/0171096 A1 | 7/2013 | Hsieh et al. | |
| 2013/0209489 A1 | 8/2013 | Han et al. | |
| 2013/0280253 A1 | 10/2013 | Hsei et al. | |
| 2013/0287777 A1 | 10/2013 | Smith et al. | |
| 2013/0336980 A1 | 12/2013 | Smith et al. | |

(Continued)

FOREIGN PATENT DOCUMENTS

KR 101 567 758 B1 11/2015
WO WO 1992/008796 A1 5/1992

(Continued)

OTHER PUBLICATIONS

Alase et al., "Interleukin-33 modulates the expression of human β-defensin 2 in human primary keratinocytes and may influence the susceptibility to bacterial superinfection in acute atopic dermatitis" *British Journal of Dermatology*, 167(6), 1386-1389 (2012).

(Continued)

*Primary Examiner* — Dong Jiang
(74) *Attorney, Agent, or Firm* — Leydig, Voit & Mayer, Ltd.

(57) ABSTRACT

The invention relates to an isolated immunoglobulin heavy chain polypeptide and an isolated immunoglobulin light chain polypeptide that bind to interleukin-33 (IL-33). The invention provides an IL-33-binding agent that comprises the aforementioned immunoglobulin heavy chain polypeptide and immunoglobulin light chain polypeptide. The invention also provides related vectors, compositions, and methods of using the IL-33-binding agent to treat a disorder in a mammal that is responsive to IL-33 inhibition.

8 Claims, 7 Drawing Sheets

Specification includes a Sequence Listing.

(56) References Cited

U.S. PATENT DOCUMENTS

| | | |
|---|---|---|
| 2014/0004107 A1 | 1/2014 | Smith et al. |
| 2014/0010822 A1 | 1/2014 | Fox et al. |
| 2014/0044645 A1 | 2/2014 | Aaron et al. |
| 2014/0044702 A1 | 2/2014 | Aaron et al. |
| 2014/0099280 A1 | 4/2014 | Girard et al. |
| 2014/0099313 A1 | 4/2014 | Wu et al. |
| 2014/0105887 A1 | 4/2014 | Chackerian et al. |
| 2014/0140954 A1 | 5/2014 | Schmitz et al. |
| 2014/0205562 A1 | 7/2014 | Wu et al. |
| 2014/0212379 A1 | 7/2014 | Wu et al. |
| 2014/0212412 A1 | 7/2014 | Rankin et al. |
| 2014/0220020 A1 | 8/2014 | Wu et al. |
| 2014/0271642 A1 | 9/2014 | Murphy et al. |
| 2014/0271658 A1 | 9/2014 | Murphy et al. |
| 2015/0038552 A1 | 2/2015 | Rothenberg et al. |
| 2015/0150947 A1 | 6/2015 | Unemori |
| 2015/0250808 A1 | 9/2015 | Deretic et al. |
| 2015/0315262 A1 | 11/2015 | Beyaert et al. |
| 2016/0168242 A1 | 6/2016 | Hass et al. |
| 2016/0289322 A1 | 10/2016 | Fujino et al. |
| 2016/0333090 A1 | 11/2016 | Horlick et al. |
| 2016/0338955 A1 | 11/2016 | Bredehorst et al. |
| 2016/0362487 A1 | 12/2016 | Murphy et al. |
| 2017/0008957 A1 | 1/2017 | Fox et al. |
| 2017/0037134 A1 | 2/2017 | Behrens et al. |
| 2017/0066831 A1 | 3/2017 | Duffy et al. |
| 2017/0067108 A1 | 3/2017 | Abbas et al. |
| 2017/0096483 A1 | 4/2017 | Orengo et al. |

FOREIGN PATENT DOCUMENTS

| | | |
|---|---|---|
| WO | WO 1994/028143 A1 | 12/1994 |
| WO | WO 2005/079844 A2 | 9/2005 |
| WO | WO 2006/085938 A2 | 8/2006 |
| WO | WO 2008/132709 A1 | 11/2008 |
| WO | WO 2008/144610 A1 | 11/2008 |
| WO | WO 2011/031600 A1 | 3/2011 |
| WO | WO 2012/103240 A2 | 8/2012 |
| WO | WO 2012/113927 A1 | 8/2012 |
| WO | WO 2013/063095 A1 | 5/2013 |
| WO | WO 2013/063395 A1 | 5/2013 |
| WO | WO 2013/126834 A1 | 8/2013 |
| WO | WO 2014/062621 A1 | 4/2014 |
| WO | WO 2014/126277 A1 | 8/2014 |
| WO | WO 2014/152195 A1 | 9/2014 |
| WO | WO 2014/164959 A2 | 10/2014 |
| WO | WO 2015/023504 A1 | 2/2015 |
| WO | WO 2015/099175 A1 | 7/2015 |
| WO | WO 2015/106080 A2 | 7/2015 |
| WO | WO 2015/143343 A2 | 9/2015 |
| WO | WO 2015/155370 A1 | 10/2015 |
| WO | WO 2015/164354 A1 | 10/2015 |
| WO | WO 2015/155370 A4 | 12/2015 |
| WO | WO 2016/077366 A8 | 5/2016 |
| WO | WO 2016/077381 A8 | 6/2016 |
| WO | WO 2016/140921 A1 | 9/2016 |
| WO | WO 2017/062456 A2 | 4/2017 |
| WO | WO 2017/124110 A1 | 7/2017 |

OTHER PUBLICATIONS

Altschul et al., *J. Molecular Biol.*, 215(3): 403-410 (1990).
Altschul et al., *Nucleic Acids Res.*, 25(17): 3389-3402 (1997).
An (ed.), *Therapeutic Monoclonal Antibodies: From Bench to Clinic*, John Wiley & Sons, Inc., Hoboken, New Jersey (2009).
Ausubel et al., *Current Protocols in Molecular Biology*, Greene Publishing Associates and John Wiley & Sons, New York, N.Y. (1994).
Beigert et al., *Proc. Natl. Acad. Sci. USA*, 106(10): 3770-3775 (2009).
Bird et al., *Science*, 242: 423-426 (1988).
Braitbard et al., "Competition between bound and free peptides in an ELISA-based procedure that assays peptides derived from protein digests," *Proteome Science.*, 4(12): (2006).
Brash et al., *Mol. Cell Biol.*, 7: 2031-2034 (1987).
Chackerian et al, "IL-1 receptor accessory protein and ST2 comprise the IL-33 receptor complex." *The Journal of Immunology* 179.4: 2551-2555 (2007).
Cherry et al., "A Novel Il-1 Family Cytokine, Il-33, Potently Activates Human Eosinophils" *J Allergy Clin Immunol* 121.6 (2008): 1484.
Coyle et al. "Crucial role of the interleukin 1 receptor family member T1/ST2 in T helper cell type 2-mediated lung mucosal immune responses." *The Journal of experimental medicine* 190.7 (1999): 895-902.
Choi et al., "Interleukin-33 induces angiogenesis and vascular permeability through ST2/TRAF6-mediated endothelial nitric oxide production." *Blood* 114.14 (2009): 3117-3126.
Colbére-Garapin et al., "A new dominant hybrid selective marker for higher eukaryotic cells." *Journal of molecular biology* 150.1 (1981): 1-14.
Conese et al., "Gene therapy progress and prospects: episomally maintained self-replicating systems." *Gene therapy* 11.24 (2004): 1735-1741.
Goff et al., "A placebo-controlled trial of D-cycloserine added to conventional neuroleptics in patients with schizophrenia." *Archives of general psychiatry* 56.1 (1999): 21-27.
David et al., "Protein iodination with solid state lactoperoxidase." *Biochemistry* 13.5 (1974): 1014-1021.
Durbin et al., eds., *Biological Sequence Analysis: Probalistic Models of Proteins and Nucleic Acids*, Cambridge University Press, Cambridge, UK (2009).
Fuhrmann-Benzakein et al. "Inducible and irreversible control of gene expression using a single transgene," *Nucleic acids research* 28.23 (2000): e99-e99.
Goeddel, *Gene Expression Technology: Methods in Enzymology*, vol. 185, Academic Press, San Diego, Calif. (1990).
Gudbjartsson et al., "Sequence variants affecting eosinophil numbers associate with asthma and myocardial infarction." *Nature genetics* 41.3 (2009): 342-347.
Gusfield, *Algorithms on Strings, Trees and Sequences*, Cambridge University Press, Cambridge UK (1997).
Harlow et al., (eds.) *Antibodies: A Laboratory Manual*, CSH Press (1988).
Holliger et al., "Engineered antibody fragments and the rise of single domains." *Nature biotechnology* 23.9 (2005): 1126-1136.
Hou et al., *J. Biochem.*, 144(1): 115-120 (2008).
Hunter et al., "Preparation of Iodine-131 Labelled Human Growth Hormone of High Specific Activity," *Nature*, 194: 495-496 (1962).
Huston et al., "Protein engineering of antibody binding sites: Recovery of specific activity in an anti-digoxin single-chain Fv analogue produced in *Escherichia coli*," *Proc. Natl. Acad. Sci. USA*, 85: 5879-5883 (1988).
Imai et al., "Skin-specific expression of IL-33 activates group 2 innate lymphoid cells and elicits atopic dermatitis-like inflammation in mice." *Proceedings of the National Academy of Sciences* 110.34 (2013): 13921-13926.
Indra et al., "Temporally-controlled site-specific mutagenesis in the basal layer of the epidermis: comparison of the recombinase activity of the tamoxifen-inducible Cre-ERT and Cre-ERT2 recombinases." *Nucleic acids research* 27.22 (1999): 4324-4327.
Janeway et al., Immunobiology: the immune system in health and disease, 6th Ed., Chapter 7 (2005).
Jack et al., *Proc. Natl. Acad. Sci. USA*, 85: 1581-1585 (1988).
Johnston "Biolistic transformation: microbes to mice." *Nature (London)* 346.6286 (1990): 776-777.
Kashmiri et al., *Methods*, 36 (1): 25-34 (2005).
Kent et al., *Science*, 237: 901-903 (1987).
Kitts et al.,Possee. "A method for producing recombinant baculovirus expression vectors at high frequency," *Biotechniques* 14.5 (1993): 810-817.
Köhler et al., "Derivation of specific antibody-producing tissue culture and tumor lines by cell fusion," *Eur. J. Immunol.*, 6: 511-519 (1976).
Kramer et al., "Transgene Control Engineering in Mammalian Cells," *Methods Molecular Biology*, 308: 123-143 (2005).

(56) References Cited

OTHER PUBLICATIONS

Lefrancais et al., "IL-33 is processed into mature bioactive forms by neutrophil elastase and cathepsin G," *Proc. Natl. Acad. Sci. USA*, 109(5): 1673-1678 (2012).
Li et al. "IL-33 blockade suppresses the development of experimental autoimmune encephalomyelitis in C57BL/6 mice." *Journal of neuroimmunology* 247.1 (Mar. 2012): 25-31.
Liu et al., "Anti-IL-33 antibody treatment inhibits airway inflammation in a murine model of allergic asthma," Biochemical and Biophysical Research Communications, Jun. 7, 2009, pp. 181-185, vol. 386.
Lonberg, *Nat. Biotechnol.*, 23(9): 1117-25 (2005).
Lonberg, *Handb. Exp. Pharmacol.*, 181: 69-97 (2008).
Lowy et al., *Cell*, 22: 817-823 (1980).
Luckow et al. "Efficient generation of infectious recombinant baculoviruses by site-specific transposon-mediated insertion of foreign genes into a baculovirus genome propagated in *Escherichia coli.*" *Journal of virology* 67.8 (1993): 4566-4579.
Luckow "Baculovirus systems for the expression of human gene products." *Current opinion in biotechnology* 4.5 (1993): 564-572.
Mchedlidze et al., *Immunity*, 39: 357-371 (2013).
Melén et al. "Analyses of shared genetic factors between asthma and obesity in children." *Journal of Allergy and Clinical Immunology* 126.3 (2010): 631-637.
Moffatt et al. "A large-scale, consortium-based genomewide association study of asthma." *New England Journal of Medicine* 363.13 (2010): 1211-1221.
Moulin et al. "Interleukin (IL)-33 induces the release of pro-inflammatory mediators by mast cells," *Cytokine* 40.3 (2007): 216-225.
Mulligan et al., *Proc. Natl. Acad. Sci. USA*, 78: 2072-2076 (1981).
No et al., *Proc. Natl. Acad. Sci.*, 93: 3346-3351 (1996).
Nygren, *Histochem. and Cytochem.*, 30: 407-412 (1982).
O'Hare et al., *Proc. Natl. Acad. Sci. USA*, 78: 1527-1531 (1981).
Osbourn et al., *Nat. Biotechnol.*, 16: 778 (1998).
Pain et al., "Preparation of protein A-peroxidase monoconjugate using a heterobifunctional reagent, and its use in enzyme immunoassays." *Journal of immunological methods* 40.2 (1981): 219-230.
Préfontaine et al. "Increased expression of IL-33 in severe asthma: evidence of expression by airway smooth muscle cells," *The Journal of Immunology* 183.8 (2009): 5094-5103.
Remington, *Remington: The science and practice of pharmacy*. Eds. David B. Troy, and Paul Beringer. vol. 1. Lippincott Williams & Wilkins, 2006.
Rudikoff et al., "Single amino acid substitution altering antigen-binding specificity." *Proceedings of the National Academy of Sciences* 79.6 (Mar. 1982): 1979-1983.
Sambrook et al., *Molecular Cloning, a Laboratory Manual, 3rd edition*, Cold Spring Harbor Press, Cold Spring Harbor, N.Y. (2001).
Santerre et al., "Expression of prokaryotic genes for hygromycin B and G418 resistance as dominant-selection markers in mouse L cells." *Gene* 30.1 (1984): 147-156.
Savinko et al., "IL-33 and ST2 in atopic dermatitis: expression profiles and modulation by triggering factors," *Journal of Investigative Dermatology* 132.5 (2012): 1392-1400.
Schmitz et al., "IL-33, an interleukin-1-like cytokine that signals via the IL-1 receptor-related protein ST2 and induces T helper type 2-associated cytokines." *Immunity* 23.5 (2005): 479-490.
Schulz et al., *Principles of Protein Structure*, Springer-Verlag, New York (1979).
Shimizu et al., "Functional SNPs in the distal promoter of the ST2 gene are associated with atopic dermatitis." *Human molecular genetics* 14.19 (2005): 2919-2927.
Söding, "Protein homology detection by HMM-HMM comparison." *Bioinformatics* 21.7 (2005): 951-960.
Szybalskaet al., *Proc. Natl. Acad. Sci. USA*, 48: 2026-2034 (1962).
Tare et al., *Exp. Cell Res.*, 316(15): 2527-37 (2010).
Tominaga, A putative protein of a growth specific cDNA from BALB/c-3T3 cells is highly similar to the extracellular portion of mouse interleukin 1 receptor, FEBS Lett., 258 (1989), pp. 301-304.
Torgerson et al., "Meta-analysis of genome-wide association studies of asthma in ethnically diverse North American populations." *Nature genetics* 43.9 (2011): 887-892.
Urlaub et al., *Proc. Natl. Acad. Sci. USA*, 97: 4216-4220 (1980).
Wigler et al., *Cell*, 11: 223-232 (1977).
Wigler et al., *Proc. Natl. Acad. Sci. USA*, 77: 3567-3570 (1980).
Yagami et al., "IL-33 mediates inflammatory responses in human lung tissue cells." *The Journal of Immunology* 185.10 (2010): 5743-5750.
A.A. Yarilin, "Basic Immunology", M.: Medicine, 1999, pp. 169-174).
Yuan et al., "Construction of Human Nonimmune Library and Selection of scFvs Against IL-33," Applied Biochemistry and Biotechnology, May 6, 2012, pp. 498-509, vol. 167.
Zola, *Monoclonal Antibodies: A Manual of Techniques*, CRC Press, Inc. (1987).
United States Patent and Trademark Office, International Search Report and Written Opinion for International Application No. PCT/US2015/010785 (dated Jul. 8, 2015).
United States Patent and Trademark Office, International Preliminary Report on Patentability for International Application No. PCT/US2015/010785 (dated Jul. 12, 2016).
European Search Report for European Application No. 15735107.3 (dated Jul. 17, 2017).
Extended European Search Report for European Application No. 15735107.3 (dated Nov. 3, 2017).
Aagaard et al., "RNAi therapeutics: Principles, prospects and challenges," *Advanced Drug Delivery Reviews*, 59: 75-86 (2007).
Ai-Sajee et al., "Expression of IL-33 and TSLP and Their Receptors in Asthmatic Airways after Inhaled Allergen Challenge," *Am. J. Resp. Critical Care Med.*, 198(6):805-807 (2018).
Bork, "Powers and Pitfalls in Sequence Analysis: The 70% Hurdle," Genome Res., 10: 398-400 (2000).
Bowie et al., "Deciphering the Message in Protein Sequences: Tolerance to Amino Acid Substitutions," *Science*, 247(4948): 1306-1310 (1990).
Brown et al., "Tolerance to Single, but Not Multiple, Amino Acid Replacements in Antibody VH CDR2," *J. Immunol.*, 156: 3285-3291 (1996).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology*, 111: 2129-2138 1990.
Clark et al., "Discovery and Development of Janus Kinase (JAK) Inhibitors for Inflammatory Diseases," *J. Med. Chem.*, 57: 5023-5038 (2014).
Chu et al: "IL-33, but not thymic stromal lymphopoietin or IL-25, is central to mite and peanut allergic sensitization", *J. Allergy Clin. Immunol.*, 187-200 (Jan. 1, 2013).
Dondelinger et al., "Understanding the Significance and Implications of Antibody Numbering and Antigen-Binding Surface/Residue Definition," *Frontiers in Immunology*, 9(2278): 1-15 (2018).
Guido et al., "Virtual Screening and Its Integration with Modern Drug Design Technologies," *Current Medical Chemistry*, 15: 37-46 (2008).
Khaitov et al., "The Role of Interleukin-33 in Pathogenesis of Bronchial Asthma. New Experimental Data," *Biochemistry*, 83(1): 13-25 (2018).
Kim et al., "Anti-IL-33 antibody has a therapeutic effect in a murine model of allergic rhinitis" Allergy 67: 13-190 (2012).
Lazar et al., Transforming Growth Factor α: Mutation of Aspartic Acid 47 and Leucine 48 Results in Different Biological Activities, *Mol. Cell. Biol.*, 8(3): 1247-1252 (1988).
Londei et al., A Phase 1 Study of ANB020, an anti-IL-33 monoclonal Antibody in Healthy Volunteers. *J. Allergy Clin. Immunol.* 139:2 AB73 (2017).
McKeague et al., "Challenges and Opportunities for Small Molecule Aptamer Development," *Journal of Nucleic Acids*, 20 pages (2012).

(56) References Cited

OTHER PUBLICATIONS

Mitchell et al., "Emerging monoclonal antibodies as targeted innovative therapeutic approaches to asthma," *Clin. Pharm. Therapeut.* 99(1): 38-48 (2016).
Mitchell et al., IL-33 and Its Receptor ST2 after Inhaled Allergen Challenge in Allergic Asthmatics; *Intl. Archives Allergy Immunol.* 476(2): 133-142 (2018).
Nabe, "Interleukin (IL)-33: New Therapeutic Target for Atopic Diseases", *J. Pharmacol. Sci.*, 126:2 85-91 (2014).
Ogg, "Proof-of-Concept Phase-2a Clinical Trial of ANB020 {Anti-IL-33 Antibody) in the Treatment of Moderate-to-Severe Adult Atopic Dermatitis". (2018). Retrieved from the Internet: URL:https://www2.anaptysbio.com/wp-content/uploads/ANB020-Graham-Ogg-EAACI-052918.pdf.
Pagliarulo, "AnaptysBio shares collapse after 'worst case scenario' for key drug," BiopharmaDive (2019).Retrieved from the Internet: URL:https://www.biopharmadive.com/news/anaptysbio-shares-collapse-etokimab-fails-phase-2/566954/ [retrieved on Nov. 22, 2019].
Peng et al., "Anti-IL-33 Antibody Has a Therapeutic Effect in an Atopic Dermatitis Murine Model Induced by 2,4-Dinitrochlorobenzene", *Inflammation* 41:1, 154-163 (2017).
Sampson et al., "Standardizing double-blind, placebo-controlled oral food challenges: American Academy of Allergy, Asthma & Immunology—European Academy of Allergy and Clinical Immunology PRACTALL consensus report," *J. Allergy Clin. Immunol.* 130(6): 1260-1274 (Dec. 2012).
Sullivan: "Anti-IL-33 antibody stakes a first-in-class claim on moderate to severe atopic dermatitis" *Dermatology News* (2018) Retrieved from the Internet: URL:https://www.mdedge.com/edermatologynews/article/159239/atopic-dermatitis/anti-il-33-antibody-stakes-first-class-claim.
Vajdos et al., "Comprehensive Functional Maps of the Antigen-binding Site of an Anti-ErbB2 Antibody Obtained with Shotgun Scanning Mutagenesis," *J. Mol. Biol.*, 320: 415-428 (2002).
Warzocha et al., "Antisense Strategy: Biological Utility and Prospects in the Treatment of Hematological Malignancies," *Leukemia and Lymphoma*, 24: 267-281 (1997).
Eurasian Patent Office, Office Action in Eurasian Application No. 201891628, (dated Dec. 10, 2019).
European Patent Office, International Search Report and the Written Opinion in International Application No. PCT/US2018/054989 (dated Jan. 23, 2019).
European Patent Office, Extended European Search Report in European Application No. 177391653, (dated Nov. 6, 2019).
European Patent Office, International Search Report and the Written Opinion in International Application No. PCT/US2019/052464 (dated Dec. 6, 2019).
United States Patent and Trademark Office, International Search Report and the Written Opinion in International Application No. PCT/US2017/0138818 (dated May 19, 2017).
United States Patent and Trademark Office, International Search Report and the Written Opinion in International Application No. PCT/US2019/23927 (dated Aug. 7, 2019).

METHOD OF TREATING INFLAMMATORY DISORDER WITH ANTIBODIES DIRECTED AGAINST INTERLEUKIN-33 (IL-33)

CROSS-REFERENCE TO RELATED APPLICATIONS

This patent application is a divisional of U.S. Pat. No. 10,059,764, issued on Aug. 28, 2018, which is the U.S. national phase of International Patent Application No. PCT/US2015/010785, filed on Jan. 9, 2015, which claims the benefit of U.S. Patent Application No. 61/925,946, filed on Jan. 10, 2014, each of which are incorporated by reference in their entireties herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 283,368 Byte ASCII (Text) file named "739957 ST25.txt," created on Jul. 20, 2018.

BACKGROUND OF THE INVENTION

Interleukin 33 (IL-33), also known as nuclear factor (NF) in high endothelial venules (NF-HEV), is a cytokine belonging to the IL-1 superfamily. IL-33 induces helper T cells, mast cells, eosinophils and basophils to produce type 2 cytokines. IL-33 mediates its biological effects by interacting with the receptors ST2 (also known as IL1RL1) and IL-1 Receptor Accessory Protein (IL1RAP) to activate intracellular molecules in the NF-κB and MAP kinase signaling pathways that drive production of type 2 cytokines (e.g., IL-4, IL-5, and IL-13) from polarized helper T cells (Th2) and Group-2 innate lymphoid cells (ILC2) in the skin, lungs, and gastrointestinal tract. IL-33 acts directly on mast cells to trigger their activation, and stimulates eosinophils and basophils to degranulate, causing tissue damage. The induction of type 2 cytokines by IL-33 in vivo is believed to induce the severe pathological changes observed in mucosal organs following administration of IL-33 (see, e.g., Schmitz et al., *Immunity*, 23(5): 479-490 (2005); and Chackerian et al., *J. Immunol.*, 179 (4): 2551-2555 (2007))

Both the in vivo expression profile of IL-33 and its cellular targets suggest a role for IL-33 in Th2-driven pathologies. For example, IL-33 expression has been detected in inflamed tissue from patients with moderate-to-severe asthma, atopic dermatitis, allergic rhinitis, food allergies, rheumatoid arthritis, multiple sclerosis, and Crohn's disease. In addition, functional single nucleotide polymorphisms (SNPs) in the distal promoter region of ST2 (IL-33R) have shown a significant association with atopic dermatitis (see, e.g., Shimizu et al., *Hum. Mol. Genet.*, 14(19): 2919-2927 (2005)). Genome-wide association studies (GWAS) have also shown a strong link with SNPs in IL-33 and ST2 (IL-33R) genes for asthma in multiple studies of ethnically diverse groups (see, e.g., Gudbjartsson et al., *Nat. Genet.*, 41(3): 342-347 (2009); Melén et al., *J Allergy Clin. Immunol.*, 126(3): 631-637 (2010); Moffatt et al., *New Engl J. Med.*, 363(13):1211-1221 (2010); and Torgerson et al., Nat. Genet., 43(9): 887-92 (2011)). IL-33 (possibly in combination with IL-25 and TSLP) also activates innate lymphoid cells (ILC2 cells) leading to Th2 cytokine secretion, anti-parasitic responses, and tissue immunopathology.

Studies also suggest that IL-33 plays a direct role in some cancers expressing the IL-33 receptor such as, for example, epithelial cancers (i.e., carcinomas) by acting as a survival or growth factor for cancer cells. Such responsiveness to IL-33 might contribute to escape of certain cancer cell types from current standard of care (e.g., chronic myelogenous leukemia (CML), breast cancers, and gastrointestinal cancers). Furthermore, IL-33 may play an indirect role in cancer progression by reducing the protective activity of the immune system in controlling tumor cells. Other recent studies suggest that IL-33 plays a role in the pathology of fibrosis, such as, for example, skin fibrosis, liver fibrosis, systemic sclerosis, and lung fibrosis. In addition, Mchedlidze et al., *Immunity*, 39: 357-371 (2013), demonstrates that hepatic expression of interleukin-33 (IL-33) is both required and sufficient for severe hepatic fibrosis in vivo.

Therefore, there is a need for inhibitors of IL-33 (e.g., antibodies) that bind IL-33 with high affinity and effectively neutralize IL-33 activity. The invention provides an IL-33 binding agent that binds to and inhibits IL-33.

BRIEF SUMMARY OF THE INVENTION

The invention provides an isolated immunoglobulin heavy chain polypeptide which comprises (a) an amino acid sequence of any one of SEQ ID NO: 1, SEQ ID NO: 2, and SEQ ID NOs: 5-50, or (b) an amino acid sequence that is at least 90% identical to any one of SEQ ID NO: 1, SEQ ID NO: 2, SEQ ID NOs: 5-50, SEQ ID NOs: 67-140, SEQ ID NO: 176, SEQ ID NO: 177, SEQ ID NOs: 178-188, and SEQ ID NOs: 206-217.

The invention provides an isolated immunoglobulin light chain polypeptide which comprises (a) an amino acid sequence of any one of SEQ ID NO: 3, SEQ ID NO: 4, and SEQ ID NOs: 51-66, or (b) an amino acid sequence that is at least 90% identical to any one of SEQ ID NO: 3, SEQ ID NO: 4, SEQ ID NOs: 51-66, SEQ ID NOs: 141-175, SEQ ID NOs: 189-205, and SEQ ID NOs: 218-231.

In addition, the invention provides isolated or purified nucleic acid sequences encoding the foregoing immunoglobulin polypeptides, vectors comprising such nucleic acid sequences, isolated IL-33-binding agents comprising the foregoing immunoglobulin polypeptides, nucleic acid sequences encoding such IL-33-binding agents, vectors comprising such nucleic acid sequences, isolated cells comprising such vectors, compositions comprising such IL-33-binding agents or such vectors with a pharmaceutically acceptable carrier, and methods of treating a disease or disorder in mammals that is responsive to IL-33 inhibition or neutralization by administering effective amounts of such compositions to mammals.

BRIEF DESCRIPTION OF THE SEVERAL VIEW OF THE DRAWINGs

Figure 1A:
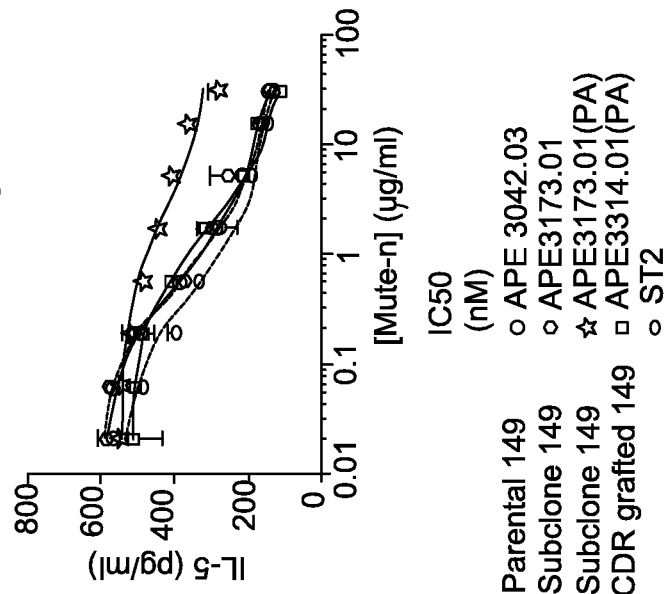
FIG. 1A is a graph which depicts experimental data illustrating the determination of $EC_{50}$ for IL-33 stimulation of IL-5 secretion from KU812 cells.
Figure 1B:
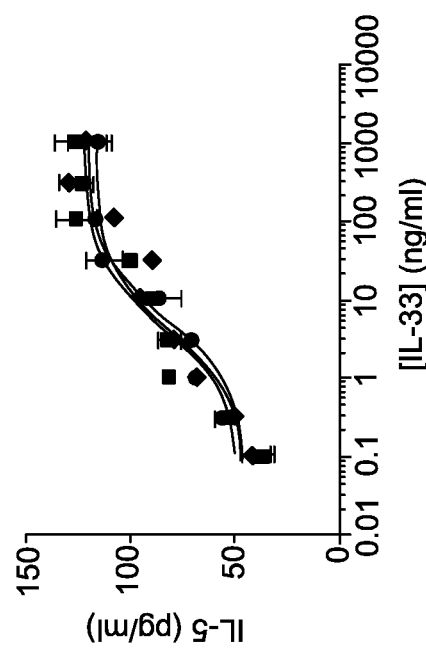
FIG. 1B is a graph which depicts experimental data illustrating that the inventive IL-33 binding agent inhibits IL-33-mediated release of IL-5 from KU812 cells.
Figure 2A:
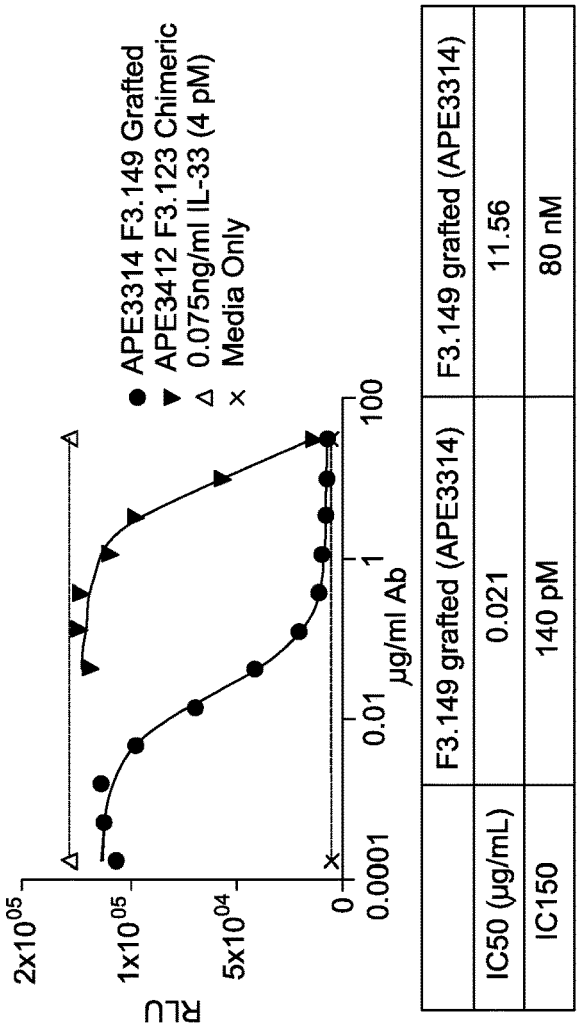
FIG. 2A is a graph which depicts experimental data illustrating that IL-33-induces expression of luciferase from the IL-8 promoter in HEK293-ST2 cells.
Figure 2B:
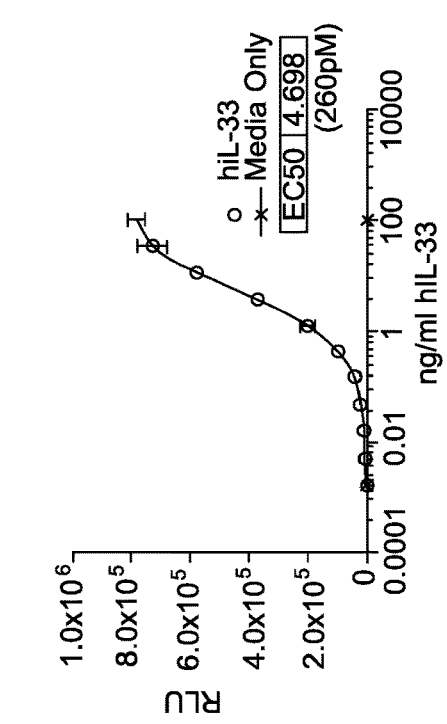
FIG. 2B is a graph which depicts experimental data illustrating that the inventive IL-33 binding agent inhibits IL-33-induced expression of luciferase from the IL-8 promoter in HEK293-ST2 cells.
Figure 3:
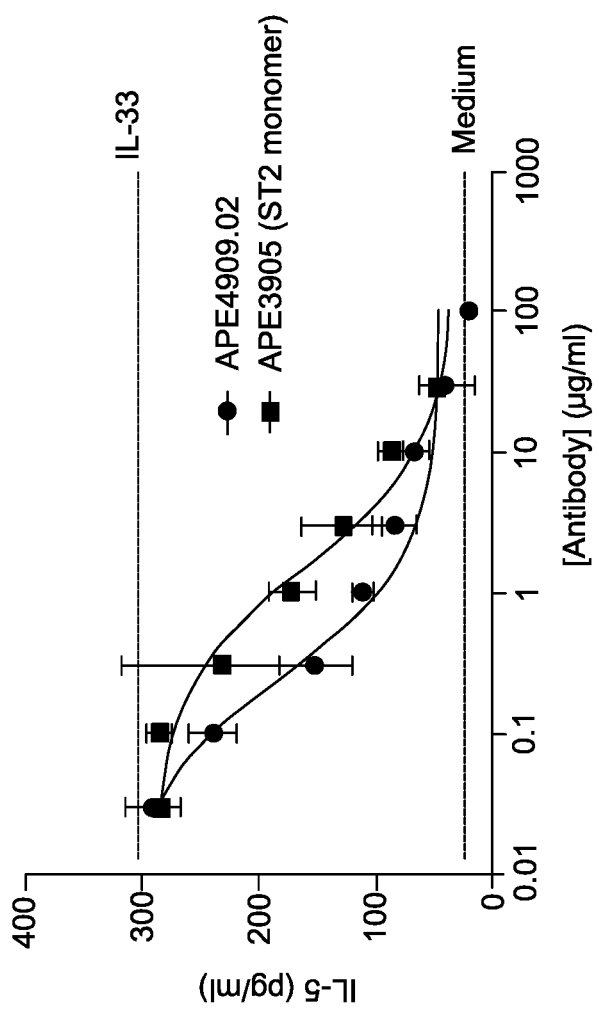

FIG. 3 is a graph which depicts experimental data illustrating that the inventive IL-33-binding agent inhibits IL-33-mediated release of IL-5 in primary human basophils. For APE4909, IC50=2.2±1.1 nM (N=3); for ST2 monomer, IC50=20 nM (N=1). The dashed lines marked "IL-33" and "medium" represent the concentration of IL-5 secreted in the absence of antibody and in the absence of IL-33, respectively. The 0.02 suffix appended to APE4909 refers to the lot of protein tested in these experiments.

Figure 4:
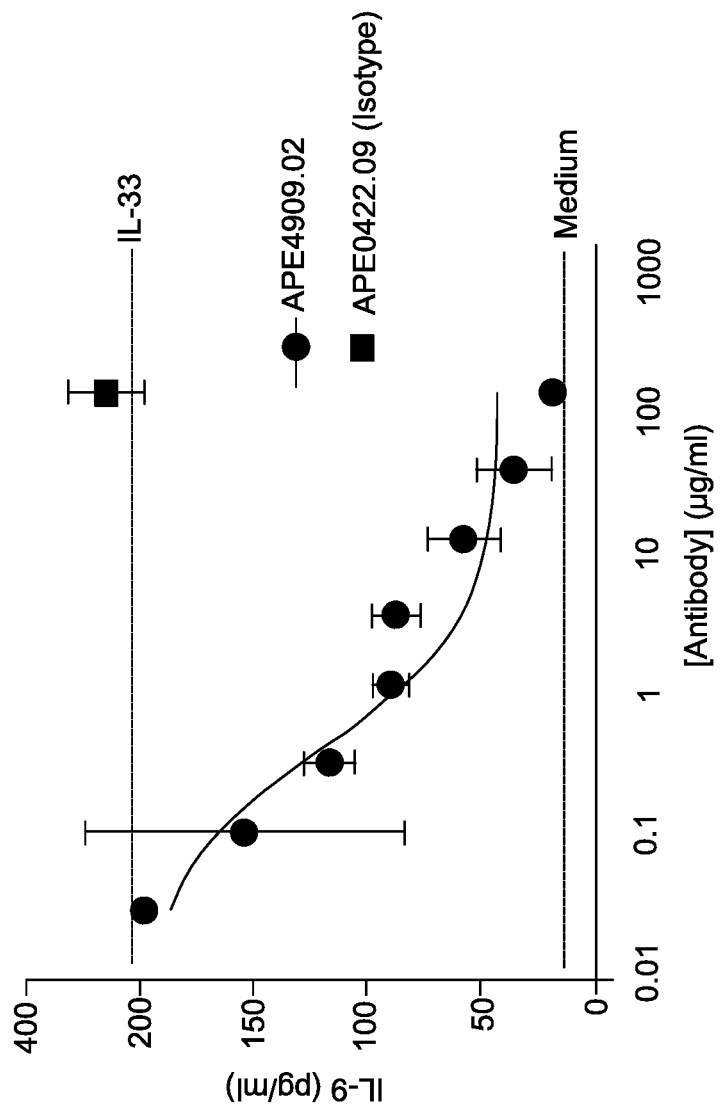

FIG. 4 is a graph which depicts experimental data illustrating that the inventive IL-33-binding agent inhibits IL-33-mediated release of IL-9 from primary human basophils. The $IC_{50}$ for APE4909 was measured at 3 nM. The dashed lines marked "IL-33" and "medium" represent the concentration of IL-9 secreted in the absence of antibody and in the absence of IL-33, respectively. The antibody APE0422 represents an isotype control antibody.

Figure 5:
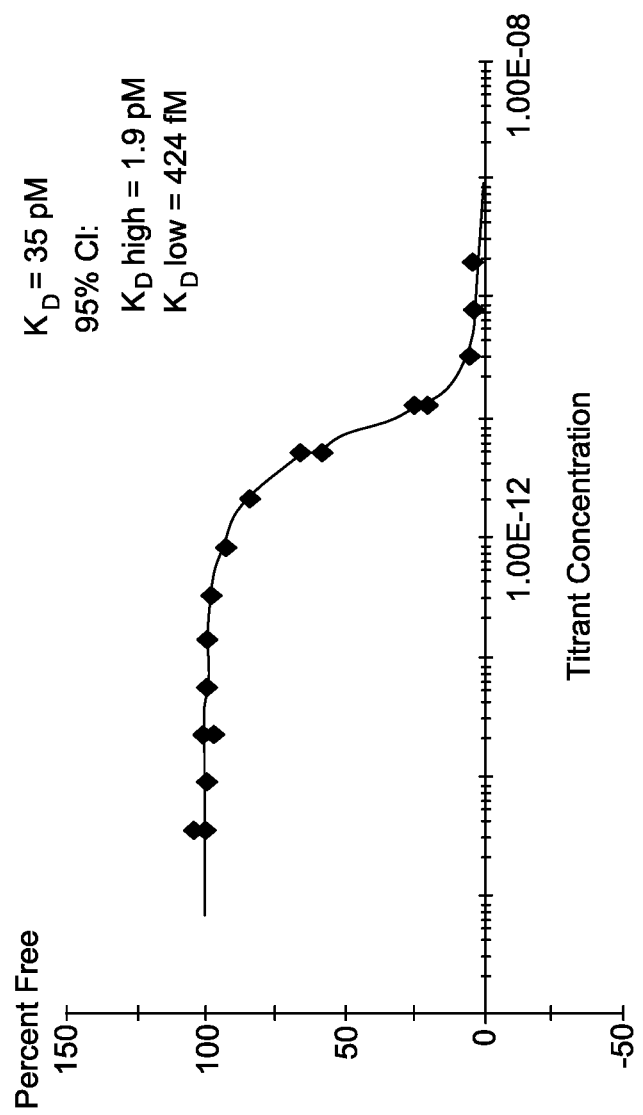

FIG. 5 is a graph which depicts experimental data illustrating affinity of the inventive APE4909 antibody for human IL-33 as measured by KINEXA™. Results indicate KD=1.0 pM (N=2) with 95% confidence interval (CI) of 1.9 pM-420 fM.

Figure 6:
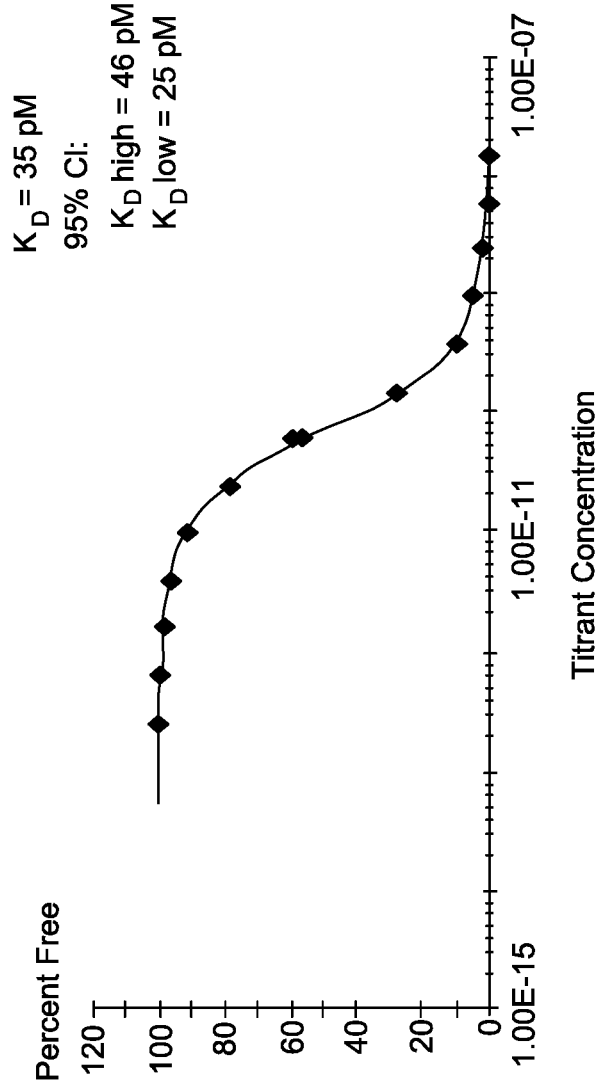

FIG. 6 is a graph which depicts experimental data illustrating affinity of the inventive APE4909 antibody for cynomolgus IL-33 as measured by KINEXA™.

Figure 7:
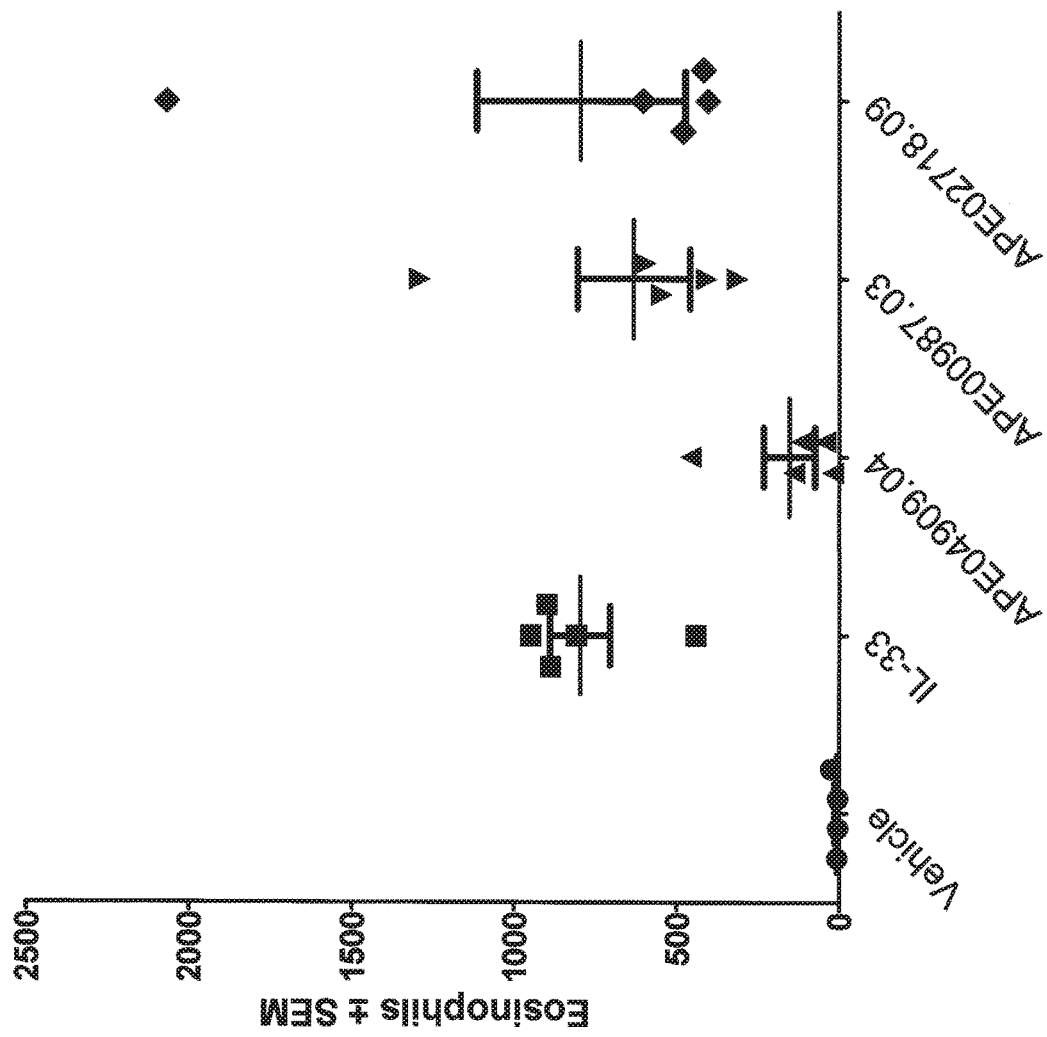

FIG. 7 is a graph which depicts experimental data illustrating the ability of the inventive APE4909 antibody to inhibit human IL-33-driven eosinophil expansion in the peripheral blood compartment.

DETAILED DESCRIPTION OF THE INVENTION

The invention provides an isolated immunoglobulin heavy chain polypeptide and/or an isolated immunoglobulin light chain polypeptide, or a fragment (e.g., antigen-binding fragment) thereof. The term "immunoglobulin" or "antibody," as used herein, refers to a protein that is found in blood or other bodily fluids of vertebrates, which is used by the immune system to identify and neutralize foreign objects, such as bacteria and viruses. The polypeptide is "isolated" in that it is removed from its natural environment. In a preferred embodiment, an immunoglobulin or antibody is a protein that comprises at least one complementarity determining region (CDR). The CDRs form the "hypervariable region" of an antibody, which is responsible for antigen binding (discussed further below). A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_H1$, $C_H2$, and $C_H3$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), *Immunobiology*, 5th Ed., Garland Publishing, New York, N.Y. (2001)).

The framework regions are connected by three complementarity determining regions (CDRs). As discussed above, the three CDRs, known as CDR1, CDR2, and CDR3, form the "hypervariable region" of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

The isolated immunoglobulin heavy chain polypeptide and the isolated immunoglobulin light chain polypeptide of the invention desirably bind to IL-33. As discussed above, interleukin-33 (IL-33) (also known as nuclear factor (NF) in high endothelial venules (NF-HEV)) is a cytokine of the IL-1 family, which also includes the inflammatory cytokines IL-1α, IL-1β, and IL-18. IL-33 has been shown to signal via the ST2 receptor and the IL1RAP receptor. IL-33 is expressed broadly in various tissues, including stomach, lung, spinal cord, brain, and skin, as well as in cells, including smooth muscle cells and epithelial cells lining bronchus and small airways. IL-33 expression is induced by IL-1β and tumor necrosis factor-α (TNF-α) in lung and dermal fibroblasts and, to a lesser extent, by macrophage activation. IL-33 treatment has been shown to induce T-helper (Th) type 2 responses in mice as indicated by an increase in Th2 cytokine production and serum immunoglobulin. Systemic treatment of mice with IL-33 results in pathologic changes in the lung and the digestive tract (see, e.g., Choi et al., *Blood*, 114(14): 3117-3126 (2009); and Yagami et al., *J. Immunology*, 185(10): 5743-5750 (2010)).

IL-33 is produced as a 30-kDa precursor protein that is cleaved in vitro by caspase-1, releasing the mature 18-kDa form (see, e.g., Schmitz et al., *Immunity*, 23(5): 479-490 (2005)). Upon binding to the ST2 receptor, IL-33 promotes the activation of nuclear factor (NF)-κB and mitogen-activated protein kinase (MAPK), leading to increased transcription of Th2 cytokines (Schmitz et al., supra).

Antibodies which bind to IL-33, and components thereof, are known in the art (see, e.g., U.S. Patent Application Publications 2009/0041718 A1 and 2012/0263709 A1). Anti-IL-33 antibodies also are commercially available from sources such as, for example, Abcam (Cambridge, Mass.).

The invention provides an immunoglobulin heavy chain polypeptide that comprises an amino acid sequence of any one of SEQ ID NO: 1, SEQ ID NO: 2, SEQ ID NOs: 5-50, SEQ ID NOs: 67-140, SEQ ID NO: 176, SEQ ID NO: 177, SEQ ID NOs: 178-188, and SEQ ID NOs: 206-217, or an amino acid sequence that is at least 90% identical to any one of SEQ ID NO: 1, SEQ ID NO: 2, SEQ ID NOs: 5-50, SEQ ID NOs: 67-140, SEQ ID NO: 176, SEQ ID NO: 177, SEQ ID NOs: 178-188, and SEQ ID NOs: 206-217. In one embodiment of the invention, the isolated immunoglobulin heavy chain polypeptide comprises, consists of, or consists essentially of an amino acid sequence of any one of SEQ ID NO: 1, SEQ ID NO: 2, SEQ ID NOs: 5-50, SEQ ID NOs: 67-140, SEQ ID NO: 176, SEQ ID NO: 177, SEQ ID NOs: 178-188, and SEQ ID NOs: 206-217. When the inventive immunoglobulin heavy chain polypeptide consists essentially of an amino acid sequence of any one of SEQ ID NO: 1, SEQ ID NO: 2, SEQ ID NOs: 5-50, SEQ ID NOs: 67-140, SEQ ID NO: 176, SEQ ID NO: 177, SEQ ID NOs: 178-188, and SEQ ID NOs: 206-217, additional components can be included in the polypeptide that do not materially affect the polypeptide (e.g., protein moieties such as biotin that facilitate purification or isolation). When the inventive immunoglobulin heavy chain polypeptide consists of an amino acid sequence of any one of SEQ ID NO: 1, SEQ ID NO: 2, SEQ ID NOs: 5-50, SEQ ID NOs: 67-140, SEQ ID NO: 176, SEQ ID NO: 177, SEQ ID NOs: 178-188, and SEQ ID NOs: 206-217, the polypeptide does not comprise any additional components (i.e., components that are not endogenous to the inventive immunoglobulin heavy chain polypeptide).

The invention provides an isolated immunoglobulin heavy chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NO: 1, SEQ ID NO: 2, SEQ ID NOs: 5-50, SEQ ID NOs: 67-140, SEQ ID NO: 176, SEQ ID NO: 177, SEQ ID NOs: 178-188, or SEQ ID NOs: 206-217. Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probabilistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

The invention provides an immunoglobulin light chain polypeptide that comprises an amino acid sequence of any one of SEQ ID NO: 3, SEQ ID NO: 4, SEQ ID NOs: 51-66, SEQ ID NOs: 141-175, SEQ ID NOs: 189-205, and SEQ ID NOs: 218-231, or an amino acid sequence that is at least 90% identical to any one of SEQ ID NO: 3, SEQ ID NO: 4, SEQ ID NOs: 51-66, SEQ ID NOs: 141-175, SEQ ID NOs: 189-205, and SEQ ID NOs: 218-231. In one embodiment of the invention, the isolated immunoglobulin light chain polypeptide comprises, consists of, or consists essentially of an amino acid sequence of any one of SEQ ID NO: 3, SEQ ID NO: 4, SEQ ID NOs: 51-66, SEQ ID NOs: 141-175, SEQ ID NOs: 189-205, and SEQ ID NOs: 218-231. When the inventive immunoglobulin light chain polypeptide consists essentially of an amino acid sequence of any one of SEQ ID NO: 3, SEQ ID NO: 4, SEQ ID NOs: 51-66, SEQ ID NOs: 141-175, SEQ ID NOs: 189-205, and SEQ ID NOs: 218-231, additional components can be included in the polypeptide that do not materially affect the polypeptide (e.g., protein moieties such as biotin that facilitate purification or isolation). When the inventive immunoglobulin light chain polypeptide consists of an amino acid sequence of any one of SEQ ID NO: 3, SEQ ID NO: 4, SEQ ID NOs: 51-66, SEQ ID NOs: 141-175, SEQ ID NOs: 189-205, and SEQ ID NOs: 218-231, the polypeptide does not comprise any additional components (i.e., components that are not endogenous to the inventive immunoglobulin light chain polypeptide).

The invention provides an isolated immunoglobulin light chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NO: 3, SEQ ID NO: 4, SEQ ID NOs: 51-66, SEQ ID NOs: 141-175, SEQ ID NOs: 189-205, or SEQ ID NOs: 218-231. Nucleic acid or amino acid sequence "identity," as described herein, can be determined using the methods described herein.

One or more amino acids of the aforementioned immunoglobulin heavy chain polypeptides and/or light chain polypeptides can be replaced or substituted with a different amino acid. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In addition, one or more amino acids can be inserted into the aforementioned immunoglobulin heavy chain polypeptides and/or light chain polypeptides. Any number of any suitable amino acids can be inserted into the amino acid sequence of the immunoglobulin heavy chain polypeptide and/or light chain polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy chain polypeptide and/or light chain polypeptide. Preferably, 1-10 amino acids (e.g., 1, 2, 3, 4, 5, 6, 7, 8, 9, or 10 amino acids) are inserted into the amino acid sequence of the immunoglobulin heavy chain polypeptide and/or light chain polypeptide. In this respect, the amino acid(s) can be inserted into any one of the aforementioned immunoglobulin heavy chain polypeptides and/or light chain polypeptides in any suitable location. Preferably, the amino acid(s) are inserted into a CDR (e.g., CDR1, CDR2, or CDR3) of the immunoglobulin heavy chain polypeptide and/or light chain polypeptide.

The inventive isolated immunoglobulin heavy chain polypeptide and light chain polypeptides are not limited to polypeptides comprising the specific amino acid sequences described herein. Indeed, the immunoglobulin heavy chain polypeptide or light chain polypeptide can be any heavy chain polypeptide or light chain polypeptide that competes with the inventive immunoglobulin heavy chain polypeptide or light chain polypeptide for binding to IL-33. In this respect, for example, the immunoglobulin heavy chain polypeptide or light chain polypeptide can be any heavy chain polypeptide or light chain polypeptide that binds to the same epitope of IL-33 recognized by the heavy and light chain polypeptides described herein. Antibody competition can be assayed using routine peptide competition assays which utilize ELISA, Western blot, or immunohistochemistry methods (see, e.g., U.S. Pat. Nos. 4,828,981 and 8,568,992; and Braitbard et al., *Proteome Sci.*, 4: 12 (2006)).

The invention provides an isolated interleukin-33 (IL-33)-binding agent comprising, consisting essentially of, or consisting of one or more of the inventive isolated amino acid sequences described herein. By "interleukin-33 (IL-33)-binding agent" is meant a molecule, preferably a proteinaceous molecule, that binds specifically to IL-33. Preferably, the IL-33-binding agent is an antibody or a fragment (e.g., immunogenic fragment) thereof. The isolated IL-33-binding agent of the invention comprises, consists essentially of, or consists of the inventive isolated immunoglobulin heavy chain polypeptide and/or the inventive isolated immunoglobulin light chain polypeptide. In one embodiment, the isolated IL-33-binding agent comprises, consists essentially of, or consists of the inventive immunoglobulin heavy chain polypeptide or the inventive immunoglobulin light chain polypeptide. In another embodiment, the isolated IL-33-binding agent comprises, consists essentially of, or consists of the inventive immunoglobulin heavy chain polypeptide and the inventive immunoglobulin light chain polypeptide.

Any amino acid residue of the inventive immunoglobulin heavy chain polypeptide and/or the inventive immunoglobulin light chain polypeptide can be replaced, in any combination, with a different amino acid residue, or can be deleted or inserted, so long as the biological activity of the IL-33-binding agent is enhanced or improved as a result of the amino acid replacements, insertions, and/or deletions. The "biological activity" of an IL-33-binding agent refers to, for example, binding affinity for a particular IL-33 epitope, neutralization or inhibition of IL-33 binding to its receptor(s), neutralization or inhibition of IL-33 activity in vivo (e.g., IC$_{50}$), pharmacokinetics, and cross-reactivity (e.g., with non-human homologs or orthologs of the IL-33 protein, or with other proteins or tissues). Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

The terms "inhibit" or "neutralize," as used herein with respect to the activity of a IL-33-binding agent, refer to the ability to substantially antagonize, prohibit, prevent, restrain, slow, disrupt, alter, eliminate, stop, or reverse the progression or severity of, for example, the biological activity of IL-33, or a disease or condition associated with IL-33. The isolated IL-33-binding agent of the invention preferably inhibits or neutralizes the activity of IL-33 by at least about 20%, about 30%, about 40%, about 50%, about 60%, about 70%, about 80%, about 90%, about 95%, about 100%, or a range defined by any two of the foregoing values.

The isolated IL-33-binding agent of the invention can be a whole antibody, as described herein, or an antibody fragment. The terms "fragment of an antibody," "antibody fragment," and "functional fragment of an antibody" are used interchangeably herein to mean one or more fragments of an antibody that retain the ability to specifically bind to an antigen (see, generally, Holliger et al., *Nat. Biotech.*, 23(9): 1126-1129 (2005)). The isolated IL-33 binding agent can contain any IL-33-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $CH_1$ domains, (ii) a F(ab')$_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an F(ab')$_2$ fragment using mild reducing conditions, (v) a disulfide-stabilized Fv fragment (dsFv), and (vi) a domain antibody (dAb), which is an antibody single variable region domain (VH or VL) polypeptide that specifically binds antigen.

In embodiments where the isolated IL-33-binding agent comprises a fragment of the immunoglobulin heavy chain or light chain polypeptide, the fragment can be of any size so long as the fragment binds to, and preferably inhibits the activity of, IL-33. In this respect, a fragment of the immunoglobulin heavy chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids. Similarly, a fragment of the immunoglobulin light chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids.

When the IL-33-binding agent is an antibody or antibody fragment, the antibody or antibody fragment desirably comprises a heavy chain constant region ($F_e$) of any suitable class. Preferably, the antibody or antibody fragment comprises a heavy chain constant region that is based upon wild-type IgG1, IgG2, or IgG4 antibodies, or variants thereof.

The IL-33-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al., Science, 242: 423-426 (1988); Huston et al., Proc. Mid Acad. Sci. USA, 85: 5879-5883 (1988); and Osbourn et al., Nat. Biotechnol., 16: 778 (1998)) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024 A1.

The isolated IL-33-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The isolated IL-33-binding agent also can be an antibody conjugate. In this respect, the isolated IL-33-binding agent can be a conjugate of (1) an antibody, an alternative scaffold, or fragments thereof, and (2) a protein or non-protein moiety comprising the IL-33-binding agent. For example, the IL-33-binding agent can be all or part of an antibody conjugated to a peptide, a fluorescent molecule, or a chemotherapeutic agent.

The isolated IL-33-binding agent can be, or can be obtained from, a human antibody, a non-human antibody, or a chimeric antibody. By "chimeric" is meant an antibody or fragment thereof comprising both human and non-human regions. Preferably, the isolated IL-33-binding agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. In one embodiment of the invention, CDRH3 of the inventive IL-33-binding agent is obtained or derived from a mouse monoclonal antibody, while the remaining variable regions and constant region of the inventive IL-33-binding agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, Eur. J. Immunol., 5: 511-519 (1976); Harlow and Lane (eds.), Antibodies: A Laboratory Manual, CSH Press (1988); and Janeway et al. (eds.), Immunobiology, 5th Ed., Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, Nat. Biotechnol., 23(9): 1117-25 (2005), and Lonberg, Handb. Exp. Pharmacol., 181: 69-97 (2008)). A humanized antibody can be generated using any suitable method known in the art (see, e.g., An, Z. (ed.), Therapeutic Monoclonal Antibodies: From Bench to Clinic, John Wiley & Sons, Inc., Hoboken, N.J. (2009)), including, e.g., grafting of non-human CDRs onto a human antibody scaffold (see, e.g., Kashmiri et al., Methods, 36(1): 25-34 (2005); and Hou et al., J. Biochem., 144(1): 115-120 (2008)). In one embodiment, a humanized antibody can be produced using the methods described in, e.g., U.S. Patent Application Publication 2011/0287485 A1.

In one embodiment, a CDR (e.g., CDR1, CDR2, or CDR3) or a variable region of the immunoglobulin heavy chain polypeptide and/or the immunoglobulin light chain polypeptide described herein can be transplanted (i.e., grafted) into another molecule, such as an antibody or non-antibody polypeptide, using either protein chemistry or recombinant DNA technology. In this regard, the invention provides an isolated IL-33-binding agent comprising at least one CDR of an immunoglobulin heavy chain and/or light chain polypeptide as described herein. The isolated IL-33-binding agent can comprise one, two, or three CDRs of an immunoglobulin heavy chain and/or light chain variable region as described herein. For example, with respect to immunoglobulin heavy chain polypeptides comprising any one of SEQ ID NO: 1, SEQ ID NO: 2, or SEQ ID NOs: 5-50, the CDR1 is located between amino acid residues 26 and 35, inclusive; the CDR2 is located between amino acid residues 50 and 59, inclusive (SEQ ID NO: 1 and SEQ ID NO: 2) or between amino acid residues 50 and 66, inclusive (SEQ ID NOs: 5-50); and the CDR3 is located between amino acid residues 99 and 102, inclusive (SEQ ID NO: 1 and SEQ ID NO: 2) or between amino acid residues 99 and 111, inclusive (SEQ ID NOs 5-50). With respect to immunoglobulin light chain polypeptides comprising any one of SEQ ID NO: 3, SEQ ID NO: 4, and SEQ ID NO: 51-66, for example, the CDR1 is located between amino acid residues 24 and 39, inclusive (SEQ ID NO: 3 and SEQ ID NO: 4) or between amino acid residues 24 and 34, inclusive (SEQ ID NOs: 51-66); the CDR2 is located between amino acid residues 55 and 61, inclusive (SEQ ID NO: 3 and SEQ ID NO: 4) or between amino acid residues 50 and 56, inclusive (SEQ ID NOs: 51-66); the CDR3 is located between amino acid residues 94 and 102, inclusive (SEQ ID NO: 3 and SEQ ID NO: 4) or between amino acid residues 89 and 97, inclusive (SEQ ID NOs: 51-66).

In a preferred embodiment, the IL-33-binding agent binds an epitope of IL-33 which blocks the binding of IL-33 to receptors ST2 (also known as IL1RL1) and/or IL-1 Receptor Accessory Protein (IL1RAP) and inhibits IL-33 mediated signaling. The invention also provides an isolated or purified epitope of IL-33 which blocks the binding of IL-33 to receptors ST2 and IL1RAP in an indirect or allosteric manner.

The invention also provides one or more isolated or purified nucleic acid sequences that encode the inventive immunoglobulin heavy chain polypeptide, the inventive immunoglobulin light chain polypeptide, and the inventive IL-33-binding agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The invention further provides a vector comprising one or more nucleic acid sequences encoding the inventive immunoglobulin heavy chain polypeptide, the inventive immunoglobulin light chain polypeptide, and/or the inventive IL-33-binding agent. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the inventive immunoglobulin heavy polypeptide, the inventive immunoglobulin light chain polypeptide, and/or the inventive IL-33-binding agent, the vector preferably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ system (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al., *J. Mol. Biol.*, 150: 1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad. Sci. USA*, 48: 2026-2034 (1962); Lowy et al., *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Life Technologies (Carlsbad, Calif.), UCOE from Millipore (Billerica, Mass.), and pCI or pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

Nucleic acid sequences encoding the inventive amino acid sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding the inventive amino acid sequences can be introduced into a host cell that is capable of expressing the polypeptides encoded thereby, including any suitable prokaryotic or eukaryotic cell. As such, the invention provides an isolated cell comprising the inventive vector. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas*, *Streptomyces*, *Salmonella*, and *Erwinia*. Particularly useful prokaryotic cells include the various strains of *Escherichia coli* (e.g., K12, HB101 (ATCC No. 33694), DH5α, DH10, MC1061 (ATCC No. 53338), and CC102).

Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia*, Rhino-sporidium, *Saccharomyces*, and *Schizosaccharomyces*. Preferred yeast cells include, for example, *Saccharomyces* cerivisae and *Pichia pastoris*.

Suitable insect cells are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and HI5 (Invitrogen, Carlsbad, Calif.).

Preferably, mammalian cells are utilized in the invention. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

Most preferably, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al., *Proc. Natl. Acad. Sci. USA*, 85: 1581-1585 (1988)), Raji cells (CCL-86), and derivatives thereof.

A nucleic acid sequence encoding the inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)). Phage or viral vectors can be introduced into host cells, after growth of infectious particles in suitable packaging cells, many of which are commercially available.

The invention provides a composition comprising an effective amount of the inventive immunoglobulin heavy chain polypeptide, the inventive immunoglobulin light chain polypeptide, the inventive IL-33-binding agent, the inventive nucleic acid sequence encoding any of the foregoing, or the inventive vector comprising the inventive nucleic acid sequence. Preferably, the composition is a pharmaceutically acceptable (e.g., physiologically acceptable) composition, which comprises a carrier, preferably a pharmaceutically acceptable (e.g., physiologically acceptable) carrier, and the inventive amino acid sequences, antigen-binding agent, or vector. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy*, 21st Edition, Lippincott Williams & Wilkins, Philadelphia, Pa. (2001).

The invention further provides a method of treating a disease or disorder in a mammal that is responsive to IL-33 inhibition or neutralization. The method comprises administering the aforementioned composition to a mammal having a disease or disorder that is responsive to IL-33 inhibition or neutralization, whereupon the disease disorder is treated in the mammal. A disease or disorder that is "responsive to IL-33 inhibition" or "responsive to IL-33 neutralization," refers to any disease or disorder in which a decrease in IL-33 levels or activity has a therapeutic benefit in mammals, preferably humans, or the improper expression (e.g., overexpression) or increased activity of IL-33 causes or contributes to the pathological effects of the disease or disorder. Diseases or disorders that are responsive to IL-33 inhibition or neutralization include, for example, inflammatory disorders, autoimmune diseases, certain cancers (e.g., epithelial cancers (carcinomas), chronic myelogenous leukemia (CML), breast cancers, and gastrointestinal cancers), and any atopic disorder. Inflammatory disorders include, for example, allergic inflammation of the skin, lungs, and gastrointestinal tract, atopic dermatitis (also known as atopic eczema), asthma (allergic and non-allergic), fibrosis (e.g., idiopathic pulmonary fibrosis, scleroderma, kidney fibrosis, and scarring), chronic obstructive pulmonary disease (COPD), allergic rhinitis, food allergies (e.g., allergies to peanuts, eggs, dairy, shellfish, tree nuts, etc.), seasonal allergies, and other allergies. Autoimmune diseases include, for example, Crohn's disease, rheumatoid arthritis, psoriasis, ankylosing spondylitis, lupus erythematosus, and scleroderma. The term "atopic," as used herein, refers to a hereditary predisposition toward developing certain hypersensitivity reactions (e.g., eczema (atopic dermatitis), hay fever (allergic rhinitis), and allergy-induced asthma (allergic asthma)), which is typically mediated by excessive IgE production.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the IL-33-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the IL-33-binding agent to elicit a desired response in the individual. For example, a therapeutically effective amount of an IL-33-binding agent of the invention is an amount which decreases IL-33 bioactivity in a human.

Alternatively, the pharmacologic and/or physiologic effect may be prophylactic, i.e., the effect completely or partially prevents a disease or symptom thereof. In this respect, the inventive method comprises administering a "prophylactically effective amount" of the IL-33-binding agent. A "prophylactically effective amount" refers to an amount effective, at dosages and for periods of time necessary, to achieve a desired prophylactic result (e.g., prevention of disease onset).

A typical dose can be, for example, in the range of 1 pg/kg to 20 mg/kg of animal or human body weight; however, doses below or above this exemplary range are within the scope of the invention. The daily parenteral dose can be about 0.00001 μg/kg to about 20 mg/kg of total body weight (e.g., about 0.001 μg/kg, about 0.1 μg/kg, about 1 μg/kg, about 5 μg/kg, about 10 μg/kg, about 100 μg/kg, about 500 μg/kg, about 1 mg/kg, about 5 mg/kg, about 10 mg/kg, or a range defined by any two of the foregoing values), preferably from about 0.1 μg/kg to about 10 mg/kg of total body weight (e.g., about 0.5 μg/kg, about 1 μg/kg, about 50 μg/kg, about 150 μg/kg, about 300 μg/kg, about 750 μg/kg, about 1.5 mg/kg, about 5 mg/kg, or a range defined by any two of the foregoing values), more preferably from about 1 μg/kg to 5 mg/kg of total body weight (e.g., about 3 μg/kg, about 15 μg/kg, about 75 μg/kg, about 300 μg/kg, about 900 μg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising an effective amount of the inventive immunoglobulin heavy chain polypeptide, the inventive immunoglobulin light chain polypeptide, the inventive IL-33-binding agent, the inventive nucleic acid sequence encoding any of the foregoing, or the inventive vector comprising the inventive nucleic acid sequence can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a cross-reactive human), the biological activity of the inventive IL-33-binding agent can be measured by any suitable method known in the art. For example, the biological activity can be assessed by determining the stability of a particular IL-33-binding agent. In one embodiment of the invention, the IL-33-binding agent (e.g., an antibody) has an in vivo half life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the IL-33-binding agent has an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the IL-33-binding agent has an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The biological activity of a particular IL-33-binding agent also can be assessed by determining its binding affinity to IL-33 or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 femtomolar (fM) to about 100 micromolar (μM) (e.g., from about 1 fM to about 1 picomolar (pM), from about 1 pM to about 1 nanomolar (nM), from about 1 nM to about 1 micromolar (μM), or from about 1 μM to about 100 μM). In one embodiment, the IL-33-binding agent can bind to an IL-33 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the IL-33-binding agent can bind to IL-33 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA (see, e.g., Janeway et al. (eds.), *Immunobiology*, 5th ed., Garland Publishing, New York, N.Y., 2001).

The IL-33-binding agent of the invention may be administered alone or in combination with other drugs (e.g., as an adjuvant). For example, the IL-33-binding agent can be administered in combination with other agents for the treatment or prevention of the diseases or disorders disclosed herein. In this respect, the IL-33-binding agent can be used in combination with at least one other anti-inflammatory agent including, for example, corticosteroids (e.g., prednisone and fluticasone) and non-steroidal anti-inflammatory drugs (NSAIDs) (e.g., aspirin, ibuprofen, and naproxen).

In addition to therapeutic uses, the IL-33-binding agent described herein can be used in diagnostic or research applications. In this respect, the IL-33-binding agent can be used in a method to diagnose a disease or disorder that is responsive to IL-33 inhibition or neutralization. In a similar manner, the IL-33-binding agent can be used in an assay to monitor IL-33 protein levels in a subject being tested for a disease or disorder that is responsive to IL-33 inhibition or neutralization. Research applications include, for example, methods that utilize the IL-33-binding agent and a label to detect an IL-33 protein in a sample, e.g., in a human body fluid or in a cell or tissue extract. The IL-33-binding agent can be used with or without modification, such as covalent or non-covalent labeling with a detectable moiety. For example, the detectable moiety can be a radioisotope (e.g., $^3H$, $^{14}C$, $^{32}P$, $^{35}S$, or $^{125}I$), a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., *Nature*, 194: 495-496 (1962); David et al., *Biochemistry*, 13: 1014-1021 (1974); Pain et al., *J. Immunol. Meth.*, 40: 219-230 (1981); and Nygren, *J. Histochem. and Cytochem.*, 30: 407-412 (1982)).

IL-33 protein levels can be measured using the inventive IL-33-binding agent by any suitable method known in the art. Such methods include, for example, radioimmunoassay (RIA), and FACS. Normal or standard expression values of IL-33 can be established using any suitable technique, e.g., by combining a sample comprising, or suspected of comprising, IL-33 with a IL-33-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of IL-33 polypeptide expressed in a sample is then compared with a standard value.

The IL-33-binding agent can be provided in a kit, i.e., a packaged combination of reagents in predetermined amounts with instructions for performing a diagnostic assay. If the IL-33-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the invention but, of course, should not be construed as in any way limiting its scope.

Example 1

This example describes assays used to determine the functional activity of the inventive immunoglobulin heavy and light chain polypeptides.
IL-33-Mediated Release of IL5 from KU812 Cells.

KU812 cells, a human basophil-like CML cell line (ATCC No. CRL-2099) (see, e.g., Tare et al., *Exp. Cell Res.*, 316(15): 2527-37 (2010); Lefrancais et al., *Proc. Natl. Acad. Sci. USA,* 109(5): 1673-1978 (2012)), respond to IL-33 stimulation by secreting IL-5. KU812 cells were suspended in RPM1+10% FBS culture medium, and 500,000 cells per well were plated into 96-well flat bottom plates. A 30 μg/mL stock for antibody of interest was serially diluted to generate 8 concentrations at half-log intervals. The diluted samples were added in rows to cells and incubated at 37° C. for 30 minutes. IL-33-his6-bio (C-terminally labeled with 6 His, and biotinylated with an average of 1 to 2 biotins per molecule) (3 ng) was then added to each well, and plates were incubated at 37° C. for 48 hours. Supernatants were then removed and held at 4° C. until testing by ELISA. Supernatants were tested using an IL-5 DuoSet ELISA kit (R&D Systems, Minneapolis, Minn.) and evaluated on a SPECTRAMAX™ microplate reader (Molecular Devices, LLC, Sunnyvale, Calif.) using SOFTMAX PRO™ Microplate Data Acquisition & Analysis Software (Molecular Devices, LLC, Sunnyvale, Calif.) to determine IL-5 production.
IL-33-Mediated Expression of Luciferase in HEK293-ST2 Cells An HEK/ST2-stable cell line was generated by first plating naïve HEK cells at 3×10$^3$ cells/T75 flask in DMEM/10% FBS and incubating overnight at 37° C. The following day, cells were transfected by mixing 500 μL Optimem (Life Technologies, Carlsbad, Calif.)+24 μL HD FUGENE™ (Promega, Madison, Wis.) and allowed to incubate at room temperature for five minutes. DNA encoding ST2-Fc (4 μg) was added to the FUGENE™ mixture and allowed to incubate at room temperature for 25 minutes. The DNA/FUGENE™ mixture was then distributed over the HEK cells and allowed to incubate overnight at 37° C., 5% CO$_2$. At 24 hours post transfection, cells were split and placed under hygromycin selection for a period of 3-4 weeks until stably selected.
IL-8 Luciferase Reporter Assay 4×10$^6$ HEK293/ST2-Fc cells were seeded in a T-75 flask overnight at 37° C., 5% CO$_2$. The following morning, the DNA construct AB4111 which encodes the human IL-8 promoter driving expression of a luciferase reporter gene, was transfected into the cells by mixing 500 μL Optimem+24 μL HD FUGENE™ and allowed to incubate at room temperature for five minutes. The IL-8 promoter responds to the signal transduction cascade initiated by stimulation of the ST2-IL-1RAcP receptor complex by IL-33 occupancy. AB4111 (2 μs) was added to the FUGENE™ mixture and allowed to incubate at room temperature for 25 minutes. The DNA/FUGENE™ mixture was then distributed over the HEK/ST2 cells and allowed to incubate for 8 hours. Cells were harvested with ACCUTASE™ and seeded into a 96-well, flat bottom plate, with 2.0×10$^4$ cells per well in 0.1 mL DMEM/10% FBS. Plates were incubated for 15-18 hours at 37° C., 5% CO$_2$. The next morning, plates were gently inverted and tapped on paper towels to remove media. 50 μL/well of fresh DMEM/10% FBS was added to each well. Cells were stimulated with pre-complexed IL-33/ST2-Fc or IL-33/Ab for 20 minutes at room temperature and then added to the cells and allowed to incubate for an additional 5 hours at 37° C. After 5 hours, luciferase activity was determined using the Steady Glo-Luciferase Assay System (Promega, Madison, Wis.) by adding luciferase reagent at 1:1 vol/vol to each well. Wells were mixed and 150 μL/well was transferred to black-walled, clear-bottom plates and read on the ENVISION™ Plate Reader (PerkinElmer, Waltham, Mass.) using the Luminescence program (60-sec delay). Data was analyzed using a 4 parameter curve fit with GraphPad Prism 5 software (GraphPad, San Diego, Calif.).
Surface Plasmon Resonance (SPR) Methods Binding kinetics and affinities of anti-IL33 antibodies were determined by SPR on a BIACORE™ T200 instrument (GE Healthcare). Each of four flow cells on a Series S CM5 chip was immobilized with ~10,000 RU anti-human IgG (Fc). Antibodies (~1 μg/mL) were captured for 60 seconds at a flow rate of 10 μL/min. Monomeric IL-33 was diluted in running buffer (HBS-EP+, pH 7.6) starting at approximately 100-fold higher concentration than each antibody's KD. Each IL-33 concentration was passed over all flow cells for 180 seconds at 30 μL/min, then allowed to dissociate for 1800 seconds. Surfaces were regenerated with 3 M MgCl$_2$ for 60 seconds. Association and dissociation kinetic constants ($k_{on}$ and $k_{off}$) and steady-state affinity (KD) were derived from the resulting sensorgrams using BIACORE T200 Evaluation Software version 1.0.

The results of the above assays with respect to several of the IL-33-binding agents described herein are shown in FIGS. 1A, 1B, 2A, and 2B.

Example 2

This example describes experiments demonstrating the functional activity of an inventive IL-33-binding agent.

An immunoglobulin heavy chain polypeptide comprising the amino acid sequence of SEQ ID NO: 136 was paired with an immunoglobulin light chain polypeptide comprising the amino acid sequence of SEQ ID NO: 171. The resulting antibody was referred to as APE4909. The ability of APE4909 to inhibit IL-33-mediated release of IL-5 and IL-9 in primary human basophils was assessed as described below.

Leukocyte Reduction System (LRS) units processed from donor whole blood were obtained from the San Diego Blood Bank. Peripheral blood mononuclear cells (PBMCs) were prepped by standard methods using Ficoll density centrifugation separation. Approximately 10$^9$ PBMCs were typically obtained from an LRS unit. Basophils were isolated from PBMCs using a human basophil isolation kit II (Miltenyi Biotec cat #130-092-662, San Diego, Calif.). The total yield of basophils was approximately 10$^6$.

Basophils were diluted to a density of 2×10$^6$/mL in RPMI 1640 medium containing 10% fetal bovine serum, penicillin/streptomycin (P/S), and 25 ng/mL of recombinant human IL-3 (R&D Systems, Minneapolis, Minn.). 100 μL of diluted cells per well were plated in standard flat-bottom 96-well tissue culture plates for a final cell density of 2×10$^5$ per well. Outside wells were filled with 200 μL PBS/well to minimize the effects of non-uniform evaporation. Cells were cultured overnight in 5% CO$_2$ in a 37° C. incubator.

The following day, APE4909 and a monomeric human ST2 protein (hST2—referred to as APE3906) were added at concentrations ranging from 30 to 0 μg/mL serially diluted at half-log intervals in RPMI+10% FBS+P/S containing 50 ng/mL IL-33. Approximately 18 hours later, plates were centrifuged at 300×g for 3 minutes. Supernatants were removed, transferred to a clean plate, and stored at −80° C. pending analysis.

IL-5 and/or IL-9 levels in the cell supernatants were assessed by ELISA using a DUOSET™ ELISA kit (R&D Systems, Minneapolis, Minn.) following the manufacturer's suggested protocol. The APE4909 antibody inhibited IL-33 mediated release of IL-5 and IL-9 in primary human basophils, as shown in FIGS. 3 and 4.

The results of this example demonstrate that the inventive IL-33-binding agent can inhibit IL-33 activity.

Example 3

This example demonstrates the affinity of an inventive IL-33 binding agent for IL-33.

The ability of the APE4909 antibody described in Example 2 to interact with IL-33 was analyzed biophysically using a KINEXA™ 3200 biosensor platform from Sapidyne Instruments (Boise, Id.). Binding experiments for human and cynomolgus IL-33 (cynoIL-33) were conducted as described below and were run twice independently. Conditions for the first experiment are shown non-parenthetically, while conditions for the second experiment are provided parenthetically.

APE4909/Human IL-33

Solid phase was prepared using azlactone-coated beads coated using a 50 μg/mL solution of histidine-tagged human IL-33. Binding experiments were performed in 1×PBS pH 7.4, 0.1% BSA. The APE4909 antibody at 10 pM (or 20 pM) final concentration was incubated with IL-33 at 200 pM to 3.4 fM (or 400 pM to 6.7 fM) final concentrations for 3 (or 4) days at 4° C. 5 mL (or 10 mL) of each mixture was applied to the beads coated with IL-33 at a rate of 0.25 mL/min for 1200 seconds (or 2400 seconds). Free antibody was detected with an ALEXAFLUOR™ 647-(Life Technologies, Carlsbad, Calif.) labeled donkey anti-human antibody. All data fit using standard KINEXA™ software.

APE4909/Cyno IL-33 (cIL-33)

Experiments were performed as described above for human IL-33, except that the APE4909 antibody at 20 pM and 100 pM final concentration was incubated with cIL-33 at 3 nM to 315 fM final concentrations for 24 hours at 4° C. Each mixture was applied to the beads coated with cIL-33 at a rate of 0.25 mL/min for 500 seconds (for 20 pM) or 2120 seconds (for 100 pM). Free antibody was detected with an ALEXAFLUOR™ 647-(Life Technologies, Carlsbad, Calif.) labeled donkey anti-human antibody. The two curves were combined using N-curve analysis, and all data fit using KINEXA™ software. To verify, the experiment was repeated at 200 pM APE4909 antibody concentration using similarly prepared solid phase, buffers, and detection reagent. The APE4909 antibody was incubated with cIL-33 at 15 nM to 250 fM final concentrations for 24 hours at 4° C. and applied to the beads coated with cIL-33 at a rate of 0.25 mL/min for 180 seconds. This data fit using standard KINEXA™ software.

APE4909 affinities for human IL-33 and cynoIL-33 are shown FIG. 5 and FIG. 6, respectively. The results of this example demonstrate that the inventive IL-33-binding agent binds to both human IL-33 and non-human primate IL-33 with high affinity.

Example 4

This example demonstrates that certain inventive IL-33-binding agents compete with the ST2 receptor for binding to human IL-33.

IL-33 binding was monitored using a BIACORE™ T200 system (GE Healthcare, Little Chalfont, Buckinghamshire, UK). Binding of IL-33 to various IL-33 antibodies disclosed herein or the human ST2 receptor was addressed by capturing an antibody and surveying the binding response of a fixed concentration of IL-33 in combination with increasing amounts of ST2. Anti-human IgG (Fc-specific, ~10,000 RU) was immobilized on a BIACORE™ CM5 chip using EDC-activated amine coupling chemistry. The inventive IL-33 antibodies or human ST2 fused to a human IgG1 Fc region (2.0 μg/mL, 1 minute contact time at a flow rate of 10 μL/min) were then captured at 25° C. (~300 RU) onto this surface. Next, an analyte solution (pre-incubated for greater than 30 minutes) containing monomeric soluble human untagged IL-33 (1 nM) and untagged human ST2 (10, 3.3, 1.1 or 0.37 nM) was flowed over captured ligands for 2 minutes at a rate of 30 μL/min, and dissociation was monitored for an additional 2 minutes. The sensor chip surface was regenerated between each cycle using 3M $MgCl_2$ (60 seconds at 30 μL/min).

A second set of experiments was performed as described above, but with the following changes: (1) the sensor chip was immobilized with anti-mouse IgG (Fc-specific, ~7500 RU); (2) human ST2 fused to murine IgG2aFc (1.0 μg/mL) was captured on the chip with a contact time of 4 minutes; and (3) the pre-incubated analyte solution contained monomeric soluble human untagged IL-33 (10 nM) and either an inventive IL-33 antibody or monomeric untagged human ST2 (100 nM, 25 nM, 6.3 nM or 1.6 nM). Analyte solution continued to incubate for approximately 30 minutes while the machine performed startup cycles. Capture and analyte binding was performed in HBS-EP+ running buffer (10 mM HEPES, pH 7.6, 150 mM NaCl, 3 mM EDTA, 0.05% Surfactant P-20; Teknova).

ST2 binding to the same epitope of IL-33 as an inventive antibody was associated with a loss of binding response, as the pre-incubation of ST2 with IL-33 would preclude access of the antibody to the epitope. ST2 binding to a different epitope of IL-33 permits IL-33 to bind the captured inventive antibody, which was observed as an increase in binding response since binding response is directly proportional to the mass of the analyte/complex. The results of these experiments are set forth in Table 1.

TABLE 1

| Inventive Antibody | Response | Conclusion |
| --- | --- | --- |
| APE00986 | no response in the absence of ST2 | does not bind IL-33 |
| APE02718 | response decreases as [ST2] increases | ST2 binds same/overlapping epitope |
| APE03833 | response decreases as [ST2] increases | ST2 binds same/overlapping epitope |
| APE04269 | response decreases as [ST2] increases | ST2 binds same/overlapping epitope |
| APE05492 | response increases as [ST2] increases | ST2 binds different epitope |

The results of this example demonstrate that certain inventive IL-33-binding agents bind to an IL-33 epitope that is similar or identical to the epitope bound by the ST2 receptor.

Example 5

This example demonstrates that an inventive IL-33-binding agent inhibits human IL-33-driven expansion of peripheral eosinophils.

IL-33 induces increased expression and release of IL-5 from CD4+ TH2 cell populations, innate lymphoid type-2 cells (ILC2 cells), and basophils. IL-5 is a cytokine that plays a key role in the differentiation, expansion, and survival of eosinophils, a population of cells that is known to mediate certain aspects of atopic disease indications, such as asthma and rhinitis. In a preliminary study, human IL-33 was injected intraperitoneally into wild-type Balb/c mice for six consecutive days at a dose of 5 µg per animal. Subsequent FACS analysis at the conclusion of this initial 6-day study indicated that human IL-33-treated mice had elevated numbers of eosinophils in their peripheral blood (as defined by high side-scatter analysis and CCR3 Siglec-F and CD16/CD32 expression) as compared to vehicle (PBS)-treated mice.

As a follow-up to the above study, wild-type Balb/c mice were again injected with 5 µg human IL-33 daily for 6-days total (days 1-6), and the anti-human IL-33 APE04909 antibody (described above) was administered on days –2 and +2 of the study at a dose of 10 mg/kg each day. Similar groups of mice treated with human IL-33 at a dose of 5 µg daily were administered either a control human IgG1 isotype mAb (designated APE00987) or human ST2-hFc fusion protein (designated APE027180), which represents a human IgG1 Fc-fusion dimeric version of the soluble IL-33 receptor (ST2). Both of these control proteins were also administered at 10 mg/kg doses on days –2 and +2 of the study only, as described for the APE04909 antibody.

As shown in FIG. 7, the anti-IL-33 APE04909 antibody substantially inhibited human IL-33-driven eosinophil expansion in the peripheral blood compartment. In comparison, the human ST2-hFc protein failed to significantly reduce blood eosinophil numbers in human IL-33-treated mice and did not show a reduced level of eosinophil numbers above that detected in mice treated with a control IgG mAb (APE00987).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating an inflammatory disorder using an interleukin-33 (IL-33) binding protein comprising an immunoglobulin heavy chain variable region comprising the CDR1, CDR2, and CDR3 of SEQ ID NO: 136, and an immunoglobulin light chain variable region comprising the CDR1, CDR2, and CDR3 of SEQ ID NO: 171.

2. The method of claim 1, wherein the inflammatory disorder is asthma.

3. The method of claim 1, wherein the inflammatory disorder is allergic rhinitis.

4. The method of claim 1, wherein the IL-33 binding protein is an antibody, an antibody conjugate, or an antigen-binding fragment thereof.

5. The method of claim 1, wherein the IL-33 binding protein is a F(ab')2, Fab', Fab, Fv, scFv, dsFv, dAb, or a single chain binding polypeptide.

6. The method of claim 1, wherein the half-life of the IL-33 binding protein is between 30 minutes and 45 days.

7. The method of claim 1, wherein the IL-33 binding protein binds to IL-33 with a $K_D$ less than or equal to 1 nanomolar.

8. The method of claim 1, wherein the IL-33 binding protein is an IgG1 antibody.

\* \* \* \* \*

SEQUENCE LISTING

```
<160> NUMBER OF SEQ ID NOS: 231

<210> SEQ ID NO 1
<211> LENGTH: 113
<212> TYPE: PRT
<213> ORGANISM: Artificial Sequence
<220> FEATURE:
<223> OTHER INFORMATION: synthetic sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asp Ile Arg Leu Lys Ser Asn Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80
```

-continued

```
Leu Tyr Leu Gln Met Asn Ser Leu Arg Ala Glu Asp Thr Ala Val Tyr
                85                  90                  95

Tyr Cys Val Arg Asp Gly Pro Tyr Trp Gly Gln Gly Thr Leu Val Thr
            100                 105                 110

Val

<210> SEQ ID NO 2
<211> LENGTH: 125
<212> TYPE: PRT
<213> ORGANISM: Artificial Sequence
<220> FEATURE:
<223> OTHER INFORMATION: synthetic sequence

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Gly Pro Tyr Trp Gly Gln Gly Thr Leu Val Thr Val Ser
            100                 105                 110

Ala Ala Ser Thr Lys Gly Pro Ser Val Phe Pro Leu Ala
        115                 120                 125

<210> SEQ ID NO 3
<211> LENGTH: 113
<212> TYPE: PRT
<213> ORGANISM: Artificial Sequence
<220> FEATURE:
<223> OTHER INFORMATION: synthetic sequence

<400> SEQUENCE: 3

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Gly Thr Lys Leu Glu Ile Lys
            100                 105                 110

Arg

<210> SEQ ID NO 4
<211> LENGTH: 113
```

-continued

```
<212> TYPE: PRT
<213> ORGANISM: Artificial Sequence
<220> FEATURE:
<223> OTHER INFORMATION: synthetic sequence

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Gly Thr Lys Leu Glu Ile Lys
            100                 105                 110

Arg

<210> SEQ ID NO 5
<211> LENGTH: 120
<212> TYPE: PRT
<213> ORGANISM: Artificial Sequence
<220> FEATURE:
<223> OTHER INFORMATION: synthetic sequence

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Val Thr Ser Pro Pro Thr Leu Leu Trp
            100                 105                 110

Gly Gln Gly Thr Leu Val Thr Val
            115                 120

<210> SEQ ID NO 6
<211> LENGTH: 120
<212> TYPE: PRT
<213> ORGANISM: Artificial Sequence
<220> FEATURE:
<223> OTHER INFORMATION: synthetic sequence

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30
```

Trp Met His Trp Val Arg Gln Ala Pro Gly Gln Gly Leu Glu Trp Met
          35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
                100                 105                 110

Gly Gln Gly Thr Leu Val Thr Val
                115                 120

<210> SEQ ID NO 7
<211> LENGTH: 120
<212> TYPE: PRT
<213> ORGANISM: Artificial Sequence
<220> FEATURE:
<223> OTHER INFORMATION: synthetic sequence

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Ser Tyr
                20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
                100                 105                 110

Gly Gln Gly Thr Leu Val Thr Val
            115                 120

<210> SEQ ID NO 8
<211> LENGTH: 120
<212> TYPE: PRT
<213> ORGANISM: Artificial Sequence
<220> FEATURE:
<223> OTHER INFORMATION: synthetic sequence

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                    85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

<210> SEQ ID NO 9
<211> LENGTH: 120
<212> TYPE: PRT
<213> ORGANISM: Artificial Sequence
<220> FEATURE:
<223> OTHER INFORMATION: synthetic sequence

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe His Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

<210> SEQ ID NO 10
<211> LENGTH: 120
<212> TYPE: PRT
<213> ORGANISM: Artificial Sequence
<220> FEATURE:
<223> OTHER INFORMATION: synthetic sequence

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

<210> SEQ ID NO 11
<211> LENGTH: 120
```

<212> TYPE: PRT
<213> ORGANISM: Artificial Sequence
<220> FEATURE:
<223> OTHER INFORMATION: synthetic sequence

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120
```

<210> SEQ ID NO 12
<211> LENGTH: 120
<212> TYPE: PRT
<213> ORGANISM: Artificial Sequence
<220> FEATURE:
<223> OTHER INFORMATION: synthetic sequence

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120
```

<210> SEQ ID NO 13
<211> LENGTH: 120
<212> TYPE: PRT
<213> ORGANISM: Artificial Sequence
<220> FEATURE:
<223> OTHER INFORMATION: synthetic sequence

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
```

-continued

```
                    20                  25                  30
Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120
```

<210> SEQ ID NO 14
<211> LENGTH: 120
<212> TYPE: PRT
<213> ORGANISM: Artificial Sequence
<220> FEATURE:
<223> OTHER INFORMATION: synthetic sequence

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120
```

<210> SEQ ID NO 15
<211> LENGTH: 120
<212> TYPE: PRT
<213> ORGANISM: Artificial Sequence
<220> FEATURE:
<223> OTHER INFORMATION: synthetic sequence

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 16
<211> LENGTH: 120
<212> TYPE: PRT
<213> ORGANISM: Artificial Sequence
<220> FEATURE:
<223> OTHER INFORMATION: synthetic sequence

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 17
<211> LENGTH: 120
<212> TYPE: PRT
<213> ORGANISM: Artificial Sequence
<220> FEATURE:
<223> OTHER INFORMATION: synthetic sequence

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln His Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 18
```

```
<211> LENGTH: 120
<212> TYPE: PRT
<213> ORGANISM: Artificial Sequence
<220> FEATURE:
<223> OTHER INFORMATION: synthetic sequence

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Thr Phe Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

<210> SEQ ID NO 19
<211> LENGTH: 120
<212> TYPE: PRT
<213> ORGANISM: Artificial Sequence
<220> FEATURE:
<223> OTHER INFORMATION: synthetic sequence

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Thr Leu Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

<210> SEQ ID NO 20
<211> LENGTH: 120
<212> TYPE: PRT
<213> ORGANISM: Artificial Sequence
<220> FEATURE:
<223> OTHER INFORMATION: synthetic sequence

<400> SEQUENCE: 20

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Asn Tyr Pro Arg Asn Ser Asp Thr Asp Tyr Asn Gln Lys Phe
    50                  55                  60

Lys Ala Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
            85                  90                  95

Ala Arg Pro Leu Tyr Tyr Tyr Val Thr Ser Pro Pro Thr Leu Leu Trp
        100                 105                 110

Gly Gln Gly Thr Leu Val Thr Val
        115                 120

<210> SEQ ID NO 21
<211> LENGTH: 120
<212> TYPE: PRT
<213> ORGANISM: Artificial Sequence
<220> FEATURE:
<223> OTHER INFORMATION: synthetic sequence

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Val Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Pro Leu Tyr Tyr Tyr Val Thr Ser Pro Pro Thr Leu Leu Trp
        100                 105                 110

Gly Gln Gly Thr Leu Val Thr Val
        115                 120

<210> SEQ ID NO 22
<211> LENGTH: 120
<212> TYPE: PRT
<213> ORGANISM: Artificial Sequence
<220> FEATURE:
<223> OTHER INFORMATION: synthetic sequence

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Asn Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80
```

Met Glu Leu Ser Ser Leu Arg Ser Glu Asp Thr Ala Val Tyr Tyr Cys
                85                  90                  95

Ala Arg Pro Leu Tyr Tyr Val Thr Ser Pro Thr Leu Leu Trp
            100                 105                 110

Gly Gln Gly Thr Leu Val Thr Val
            115                 120

<210> SEQ ID NO 23
<211> LENGTH: 120
<212> TYPE: PRT
<213> ORGANISM: Artificial Sequence
<220> FEATURE:
<223> OTHER INFORMATION: synthetic sequence

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Thr Ile Thr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Val Thr Ser Pro Thr Leu Leu Trp
            100                 105                 110

Gly Gln Gly Thr Leu Val Thr Val
            115                 120

<210> SEQ ID NO 24
<211> LENGTH: 120
<212> TYPE: PRT
<213> ORGANISM: Artificial Sequence
<220> FEATURE:
<223> OTHER INFORMATION: synthetic sequence

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Ile Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Val Thr Ser Pro Thr Leu Leu Trp
            100                 105                 110

Gly Gln Gly Thr Leu Val Thr Val
            115                 120

```
<210> SEQ ID NO 25
<211> LENGTH: 120
<212> TYPE: PRT
<213> ORGANISM: Artificial Sequence
<220> FEATURE:
<223> OTHER INFORMATION: synthetic sequence

<400> SEQUENCE: 25
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Asn Phe
    50                  55                  60

Lys Ala Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

```
<210> SEQ ID NO 26
<211> LENGTH: 120
<212> TYPE: PRT
<213> ORGANISM: Artificial Sequence
<220> FEATURE:
<223> OTHER INFORMATION: synthetic sequence

<400> SEQUENCE: 26
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Arg Phe
    50                  55                  60

Lys Ala Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

```
<210> SEQ ID NO 27
<211> LENGTH: 120
<212> TYPE: PRT
<213> ORGANISM: Artificial Sequence
<220> FEATURE:
<223> OTHER INFORMATION: synthetic sequence

<400> SEQUENCE: 27
```

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Val Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Val Thr Ser Pro Pro Thr Leu Leu Trp
                100                 105                 110

Gly Gln Gly Thr Leu Val Thr Val
            115                 120

<210> SEQ ID NO 28
<211> LENGTH: 120
<212> TYPE: PRT
<213> ORGANISM: Artificial Sequence
<220> FEATURE:
<223> OTHER INFORMATION: synthetic sequence

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Ser Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Val Thr Ser Pro Pro Thr Leu Leu Trp
                100                 105                 110

Gly Gln Gly Thr Leu Val Thr Val
            115                 120

<210> SEQ ID NO 29
<211> LENGTH: 120
<212> TYPE: PRT
<213> ORGANISM: Artificial Sequence
<220> FEATURE:
<223> OTHER INFORMATION: synthetic sequence

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Asn Thr Val Tyr
```

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 30
<211> LENGTH: 120
<212> TYPE: PRT
<213> ORGANISM: Artificial Sequence
<220> FEATURE:
<223> OTHER INFORMATION: synthetic sequence

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 31
<211> LENGTH: 120
<212> TYPE: PRT
<213> ORGANISM: Artificial Sequence
<220> FEATURE:
<223> OTHER INFORMATION: synthetic sequence

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Ser Thr Val Tyr
65                  70                  75                  80

Met Asp Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

```
<210> SEQ ID NO 32
<211> LENGTH: 120
<212> TYPE: PRT
<213> ORGANISM: Artificial Sequence
<220> FEATURE:
<223> OTHER INFORMATION: synthetic sequence

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Arg Ser Leu Arg Ser Glu Asp Thr Ala Val Tyr Tyr Cys
                85                  90                  95

Ala Arg Pro Leu Tyr Tyr Val Thr Ser Pro Thr Leu Leu Trp
                100                 105                 110

Gly Gln Gly Thr Leu Val Thr Val
            115                 120

<210> SEQ ID NO 33
<211> LENGTH: 120
<212> TYPE: PRT
<213> ORGANISM: Artificial Sequence
<220> FEATURE:
<223> OTHER INFORMATION: synthetic sequence

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Pro Leu Tyr Tyr Val Thr Ser Pro Thr Leu Leu Trp
                100                 105                 110

Gly Gln Gly Thr Leu Val Thr Val
            115                 120

<210> SEQ ID NO 34
<211> LENGTH: 120
<212> TYPE: PRT
<213> ORGANISM: Artificial Sequence
<220> FEATURE:
<223> OTHER INFORMATION: synthetic sequence

<400> SEQUENCE: 34

Gln Val Gln Leu Val Gln Ser Gly Ala Glu Val Lys Lys Pro Gly Ala
```

-continued

```
1               5                   10                  15
Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120
```

<210> SEQ ID NO 35
<211> LENGTH: 120
<212> TYPE: PRT
<213> ORGANISM: Artificial Sequence
<220> FEATURE:
<223> OTHER INFORMATION: synthetic sequence

<400> SEQUENCE: 35

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
            85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120
```

<210> SEQ ID NO 36
<211> LENGTH: 120
<212> TYPE: PRT
<213> ORGANISM: Artificial Sequence
<220> FEATURE:
<223> OTHER INFORMATION: synthetic sequence

<400> SEQUENCE: 36

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60
```

```
Lys Ala Arg Val Thr Met Thr Arg Asp Thr Ser Thr Ser Thr Val Tyr
 65                  70                  75                  80

Met Glu Leu Ser Ser Leu Arg Ser Glu Asp Thr Ala Ile Tyr Tyr Cys
                 85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 37
<211> LENGTH: 120
<212> TYPE: PRT
<213> ORGANISM: Artificial Sequence
<220> FEATURE:
<223> OTHER INFORMATION: synthetic sequence

<400> SEQUENCE: 37

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Ser Tyr
                 20                  25                  30

Trp Met His Trp Val Arg Gln Ala Pro Gly Gln Gly Leu Glu Trp Met
             35                  40                  45

Gly Thr Ile Tyr Pro Arg Asn Ser Asp Thr Asp Tyr Asn Gln Lys Phe
         50                  55                  60

Lys Ala Arg Val Thr Met Thr Arg Asp Thr Ser Thr Ser Ile Val Tyr
 65                  70                  75                  80

Met Glu Leu Ser Ser Leu Arg Ser Glu Asp Thr Ala Val Tyr Tyr Cys
                 85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 38
<211> LENGTH: 120
<212> TYPE: PRT
<213> ORGANISM: Artificial Sequence
<220> FEATURE:
<223> OTHER INFORMATION: synthetic sequence

<400> SEQUENCE: 38

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Ser Tyr
                 20                  25                  30

Phe Met His Trp Val Arg Gln Ala Pro Gly Gln Gly Leu Glu Trp Met
             35                  40                  45

Gly Thr Ile Tyr Pro Arg Asn Ser Asp Thr Asp Tyr Asn Gln Lys Phe
         50                  55                  60

Lys Ala Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120
```

<210> SEQ ID NO 39
<211> LENGTH: 120
<212> TYPE: PRT
<213> ORGANISM: Artificial Sequence
<220> FEATURE:
<223> OTHER INFORMATION: synthetic sequence

<400> SEQUENCE: 39

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Thr Ile Asp Pro Arg Asn Ser Asp Thr Asp Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
                100                 105                 110

Gly Gln Gly Thr Leu Val Thr Val
            115                 120
```

<210> SEQ ID NO 40
<211> LENGTH: 120
<212> TYPE: PRT
<213> ORGANISM: Artificial Sequence
<220> FEATURE:
<223> OTHER INFORMATION: synthetic sequence

<400> SEQUENCE: 40

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Arg Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
                100                 105                 110

Gly Gln Gly Thr Leu Val Thr Val
            115                 120
```

<210> SEQ ID NO 41
<211> LENGTH: 120
<212> TYPE: PRT
<213> ORGANISM: Artificial Sequence
<220> FEATURE:
<223> OTHER INFORMATION: synthetic sequence

<400> SEQUENCE: 41

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 42
<211> LENGTH: 120
<212> TYPE: PRT
<213> ORGANISM: Artificial Sequence
<220> FEATURE:
<223> OTHER INFORMATION: synthetic sequence

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 43
<211> LENGTH: 120
<212> TYPE: PRT
<213> ORGANISM: Artificial Sequence
<220> FEATURE:
<223> OTHER INFORMATION: synthetic sequence

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

```
Lys Ala Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 44
<211> LENGTH: 120
<212> TYPE: PRT
<213> ORGANISM: Artificial Sequence
<220> FEATURE:
<223> OTHER INFORMATION: synthetic sequence

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Leu His Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
            115                 120

<210> SEQ ID NO 45
<211> LENGTH: 120
<212> TYPE: PRT
<213> ORGANISM: Artificial Sequence
<220> FEATURE:
<223> OTHER INFORMATION: synthetic sequence

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Thr Ile Tyr Pro Arg Asn Ser Asp Thr Asp Tyr Asn Gln Lys Phe
    50                  55                  60

Lys Ala Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
```

<210> SEQ ID NO 46
<211> LENGTH: 120
<212> TYPE: PRT
<213> ORGANISM: Artificial Sequence
<220> FEATURE:
<223> OTHER INFORMATION: synthetic sequence

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp Phe Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

<210> SEQ ID NO 47
<211> LENGTH: 120
<212> TYPE: PRT
<213> ORGANISM: Artificial Sequence
<220> FEATURE:
<223> OTHER INFORMATION: synthetic sequence

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Thr Ile Tyr Pro Arg Asn Ser Asp Thr Asp His Asn Gln Lys Phe
    50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
            100                 105                 110

Gly Gln Gly Thr Leu Val Thr Val
        115                 120

<210> SEQ ID NO 48
<211> LENGTH: 120
<212> TYPE: PRT
<213> ORGANISM: Artificial Sequence
<220> FEATURE:
<223> OTHER INFORMATION: synthetic sequence

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
                100                 105                 110

Gly Gln Gly Thr Leu Val Thr Val
            115                 120

<210> SEQ ID NO 49
<211> LENGTH: 120
<212> TYPE: PRT
<213> ORGANISM: Artificial Sequence
<220> FEATURE:
<223> OTHER INFORMATION: synthetic sequence

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Gln Ala Pro Gly Gln Gly Leu Glu Trp Met
            35                  40                  45

Gly Thr Ile Tyr Pro Arg Asn Ser Asp Thr Asp Tyr Asn Gln Lys Phe
        50                  55                  60

Lys Ala Arg Val Thr Met Thr Arg Asp Thr Ser Thr Ser Ile Val Tyr
65                  70                  75                  80

Met Glu Leu Ser Ser Leu Arg Ser Glu Asp Thr Ala Val Tyr Tyr Cys
                85                  90                  95

Ala Arg Pro Leu Tyr Tyr Tyr Val Thr Ser Pro Pro Thr Leu Leu Trp
                100                 105                 110

Gly Gln Gly Thr Leu Val Thr Val
            115                 120

<210> SEQ ID NO 50
<211> LENGTH: 122
<212> TYPE: PRT
<213> ORGANISM: Artificial Sequence
<220> FEATURE:
<223> OTHER INFORMATION: synthetic sequence

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe

```
                    50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Pro Leu Tyr Tyr Val Thr Ser Pro Thr Leu Leu Trp
            100                 105                 110

Gly Gln Gly Thr Leu Val Thr Val Ser Ser
        115                 120
```

```
<210> SEQ ID NO 51
<211> LENGTH: 108
<212> TYPE: PRT
<213> ORGANISM: Artificial Sequence
<220> FEATURE:
<223> OTHER INFORMATION: synthetic sequence

<400> SEQUENCE: 51

Asp Ile Gln Leu Thr Gln Ser Pro Ser Phe Leu Ser Ala Ser Val Gly
  1               5                  10                  15

Asp Arg Val Thr Ile Thr Cys Lys Ala Ser Gln Asp Val Gly Thr Ala
             20                  25                  30

Val Ala Trp Tyr Gln Gln Lys Pro Gly Lys Ala Pro Lys Leu Leu Ile
         35                  40                  45

Tyr Trp Ala Ser Thr Arg His Thr Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Cys Asn Ser Tyr Pro Phe
                 85                  90                  95

Thr Phe Gly Ser Gly Thr Lys Leu Glu Ile Lys Arg
            100                 105
```

```
<210> SEQ ID NO 52
<211> LENGTH: 108
<212> TYPE: PRT
<213> ORGANISM: Artificial Sequence
<220> FEATURE:
<223> OTHER INFORMATION: synthetic sequence

<400> SEQUENCE: 52

Asp Ile Gln Leu Thr Gln Ser Pro Ser Phe Leu Ser Ala Ser Val Gly
  1               5                  10                  15

Asp Arg Val Thr Ile Thr Cys Lys Ala Ser Gln Asp Val Gly Thr Ala
             20                  25                  30

Val Ala Trp Tyr Gln Gln Lys Pro Gly Lys Ala Pro Lys Leu Leu Ile
         35                  40                  45

Tyr Trp Ala Ser Thr Arg His Thr Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Val Asn Ser Tyr Pro Phe
                 85                  90                  95

Thr Phe Gly Ser Gly Thr Lys Leu Glu Ile Lys Arg
            100                 105
```

```
<210> SEQ ID NO 53
<211> LENGTH: 108
```

<212> TYPE: PRT
<213> ORGANISM: Artificial Sequence
<220> FEATURE:
<223> OTHER INFORMATION: synthetic sequence

<400> SEQUENCE: 53

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ile Asn Ser Tyr Pro Phe
                85                  90                  95

Thr Phe Gly Ser Gly Thr Lys Leu Glu Ile Lys Arg
            100                 105

<210> SEQ ID NO 54
<211> LENGTH: 108
<212> TYPE: PRT
<213> ORGANISM: Artificial Sequence
<220> FEATURE:
<223> OTHER INFORMATION: synthetic sequence

<400> SEQUENCE: 54

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Ser Gly Thr Lys Leu Glu Ile Lys Arg
            100                 105

<210> SEQ ID NO 55
<211> LENGTH: 108
<212> TYPE: PRT
<213> ORGANISM: Artificial Sequence
<220> FEATURE:
<223> OTHER INFORMATION: synthetic sequence

<400> SEQUENCE: 55

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly

-continued

```
                50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Ala Asn Ser Tyr Pro Phe
                 85                  90                  95

Thr Phe Gly Ser Gly Thr Lys Leu Glu Ile Lys Arg
            100                 105

<210> SEQ ID NO 56
<211> LENGTH: 108
<212> TYPE: PRT
<213> ORGANISM: Artificial Sequence
<220> FEATURE:
<223> OTHER INFORMATION: synthetic sequence

<400> SEQUENCE: 56

Asp Ile Gln Leu Thr Gln Ser Pro Ser Phe Leu Ser Ala Ser Val Gly
  1               5                  10                  15

Asp Arg Val Thr Ile Thr Cys Lys Ala Ser Gln Asp Val Gly Thr Ala
                 20                  25                  30

Val Ala Trp Tyr Gln Gln Lys Pro Gly Lys Ala Pro Lys Leu Leu Ile
             35                  40                  45

Tyr Trp Ala Ser Thr Arg His Thr Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Ser Asn Ser Tyr Pro Phe
                 85                  90                  95

Thr Phe Gly Ser Gly Thr Lys Leu Glu Ile Lys Arg
            100                 105

<210> SEQ ID NO 57
<211> LENGTH: 108
<212> TYPE: PRT
<213> ORGANISM: Artificial Sequence
<220> FEATURE:
<223> OTHER INFORMATION: synthetic sequence

<400> SEQUENCE: 57

Asp Ile Gln Leu Thr Gln Ser Pro Ser Phe Leu Ser Ala Ser Val Gly
  1               5                  10                  15

Asp Arg Val Thr Ile Thr Cys Lys Ala Ser Gln Asp Val Gly Thr Ala
                 20                  25                  30

Val Ala Trp Tyr Gln Gln Lys Pro Gly Lys Ala Pro Lys Leu Leu Ile
             35                  40                  45

Tyr Trp Ala Ser Thr Arg His Thr Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Ala Ser Thr Tyr Pro Phe
                 85                  90                  95

Thr Phe Gly Ser Gly Thr Lys Leu Glu Ile Lys Arg
            100                 105

<210> SEQ ID NO 58
<211> LENGTH: 108
<212> TYPE: PRT
<213> ORGANISM: Artificial Sequence
<220> FEATURE:
```

<223> OTHER INFORMATION: synthetic sequence

<400> SEQUENCE: 58

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Ser Ala Tyr Pro Phe
                85                  90                  95

Thr Phe Gly Ser Gly Thr Lys Leu Glu Ile Lys Arg
            100                 105

<210> SEQ ID NO 59
<211> LENGTH: 108
<212> TYPE: PRT
<213> ORGANISM: Artificial Sequence
<220> FEATURE:
<223> OTHER INFORMATION: synthetic sequence

<400> SEQUENCE: 59

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Arg Thr Tyr Pro Phe
                85                  90                  95

Thr Phe Gly Ser Gly Thr Lys Leu Glu Ile Lys Arg
            100                 105

<210> SEQ ID NO 60
<211> LENGTH: 108
<212> TYPE: PRT
<213> ORGANISM: Artificial Sequence
<220> FEATURE:
<223> OTHER INFORMATION: synthetic sequence

<400> SEQUENCE: 60

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro

Glu Asp Phe Ala Thr Tyr Tyr Cys Gln Gln Ala Arg Ala Tyr Pro Phe
                85                  90                  95

Thr Phe Gly Ser Gly Thr Lys Leu Glu Ile Lys Arg
            100                 105

<210> SEQ ID NO 61
<211> LENGTH: 108
<212> TYPE: PRT
<213> ORGANISM: Artificial Sequence
<220> FEATURE:
<223> OTHER INFORMATION: synthetic sequence

<400> SEQUENCE: 61

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Lys Thr Tyr Pro Phe
                85                  90                  95

Thr Phe Gly Ser Gly Thr Lys Leu Glu Ile Lys Arg
            100                 105

<210> SEQ ID NO 62
<211> LENGTH: 108
<212> TYPE: PRT
<213> ORGANISM: Artificial Sequence
<220> FEATURE:
<223> OTHER INFORMATION: synthetic sequence

<400> SEQUENCE: 62

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Ala Ala Tyr Pro Phe
                85                  90                  95

Thr Phe Gly Ser Gly Thr Lys Leu Glu Ile Lys Arg
            100                 105

<210> SEQ ID NO 63
<211> LENGTH: 108
<212> TYPE: PRT
<213> ORGANISM: Artificial Sequence
<220> FEATURE:
<223> OTHER INFORMATION: synthetic sequence

<400> SEQUENCE: 63

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Ala Gln Thr Tyr Pro Phe
                85                  90                  95

Thr Phe Gly Ser Gly Thr Lys Leu Glu Ile Lys Arg
            100                 105

<210> SEQ ID NO 64
<211> LENGTH: 108
<212> TYPE: PRT
<213> ORGANISM: Artificial Sequence
<220> FEATURE:
<223> OTHER INFORMATION: synthetic sequence

<400> SEQUENCE: 64

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Ala Gln Ala Tyr Pro Phe
                85                  90                  95

Thr Phe Gly Ser Gly Thr Lys Leu Glu Ile Lys Arg
            100                 105

<210> SEQ ID NO 65
<211> LENGTH: 108
<212> TYPE: PRT
<213> ORGANISM: Artificial Sequence
<220> FEATURE:
<223> OTHER INFORMATION: synthetic sequence

<400> SEQUENCE: 65

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Ala Tyr Ser Tyr Pro Phe

```
                    85                  90                  95

Thr Phe Gly Ser Gly Thr Lys Leu Glu Ile Lys Arg
                100                 105

<210> SEQ ID NO 66
<211> LENGTH: 108
<212> TYPE: PRT
<213> ORGANISM: Artificial Sequence
<220> FEATURE:
<223> OTHER INFORMATION: synthetic sequence

<400> SEQUENCE: 66

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Cys Asn Ser Tyr Pro Phe
                85                  90                  95

Thr Phe Gly Ser Gly Thr Lys Leu Glu Ile Lys Arg
                100                 105

<210> SEQ ID NO 67
<211> LENGTH: 139
<212> TYPE: PRT
<213> ORGANISM: Artificial Sequence
<220> FEATURE:
<223> OTHER INFORMATION: synthetic sequence

<400> SEQUENCE: 67

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Val Thr Ser Pro Pro Thr Leu Leu
                115                 120                 125

Trp Gly Gln Gly Thr Leu Val Thr Val Ser Ser
    130                 135

<210> SEQ ID NO 68
<211> LENGTH: 139
<212> TYPE: PRT
<213> ORGANISM: Artificial Sequence
<220> FEATURE:
```

<223> OTHER INFORMATION: synthetic sequence

<400> SEQUENCE: 68

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Thr Leu Leu
        115                 120                 125

Trp Gly Gln Gly Thr Leu Val Thr Val Ser Ser
    130                 135

<210> SEQ ID NO 69
<211> LENGTH: 139
<212> TYPE: PRT
<213> ORGANISM: Artificial Sequence
<220> FEATURE:
<223> OTHER INFORMATION: synthetic sequence

<400> SEQUENCE: 69

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Tyr Met His Trp Val Arg Gln Ala Pro Gly Gln Gly Leu Glu Trp
    50                  55                  60

Met Gly Ile Ile Asn Pro Ser Gly Gly Ser Thr Ser Tyr Ala Gln Lys
65                  70                  75                  80

Phe Gln Gly Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Thr Leu Leu
        115                 120                 125

Trp Gly Gln Gly Thr Leu Val Thr Val Ser Ser
    130                 135

<210> SEQ ID NO 70
<211> LENGTH: 139
<212> TYPE: PRT
<213> ORGANISM: Artificial Sequence
<220> FEATURE:
<223> OTHER INFORMATION: synthetic sequence

<400> SEQUENCE: 70

Met Arg Ala Trp Ile Phe Phe Leu Leu Cys Leu Ala Gly Arg Ala Leu

```
            1               5                   10                  15
Ala Gln Val Gln Leu Val Gln Ser Gly Ala Glu Val Lys Lys Pro Gly
                    20                  25                  30

Ala Ser Val Lys Val Ser Cys Lys Ala Ser Gly Tyr Thr Phe Thr Ser
                35                  40                  45

Tyr Trp Met His Trp Val Arg Gln Ala Pro Gly Gln Gly Leu Glu Trp
            50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Ala
                    85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Val Thr Ser Pro Pro Thr Leu Leu
                115                 120                 125

Trp Gly Gln Gly Thr Leu Val Thr Val Ser Ser
        130                 135
```

<210> SEQ ID NO 71
<211> LENGTH: 139
<212> TYPE: PRT
<213> ORGANISM: Artificial Sequence
<220> FEATURE:
<223> OTHER INFORMATION: synthetic sequence

<400> SEQUENCE: 71

```
Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
                    20                  25                  30

Ala Ser Val Lys Val Ser Cys Lys Ala Ser Gly Tyr Thr Phe Thr Ser
                35                  40                  45

Tyr Trp Met His Trp Val Arg Gln Ala Pro Gly Gln Gly Leu Glu Trp
            50                  55                  60

Met Gly Thr Ile Asp Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                    85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Val Thr Ser Pro Pro Thr Leu Leu
                115                 120                 125

Trp Gly Gln Gly Thr Leu Val Thr Val Ser Ser
        130                 135
```

<210> SEQ ID NO 72
<211> LENGTH: 139
<212> TYPE: PRT
<213> ORGANISM: Artificial Sequence
<220> FEATURE:
<223> OTHER INFORMATION: synthetic sequence

<400> SEQUENCE: 72

```
Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
                    20                  25                  30
```

Ala Ser Val Lys Val Ser Cys Lys Ala Ser Gly Tyr Thr Phe Thr Ser
            35                  40                  45

Tyr Trp Met His Trp Val Arg Gln Ala Pro Gly Gln Gly Leu Glu Trp
 50                  55                  60

Met Gly Thr Ile Thr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                 85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 73
<211> LENGTH: 139
<212> TYPE: PRT
<213> ORGANISM: Artificial Sequence
<220> FEATURE:
<223> OTHER INFORMATION: synthetic sequence

<400> SEQUENCE: 73

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
            35                  40                  45

Tyr Trp Met His Trp Val Arg Gln Ala Pro Gly Gln Gly Leu Glu Trp
 50                  55                  60

Met Gly Thr Ile Asn Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                 85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 74
<211> LENGTH: 139
<212> TYPE: PRT
<213> ORGANISM: Artificial Sequence
<220> FEATURE:
<223> OTHER INFORMATION: synthetic sequence

<400> SEQUENCE: 74

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
            35                  40                  45

Tyr Trp Met His Trp Val Arg Gln Ala Pro Gly Gln Gly Leu Glu Trp
 50                  55                  60

```
Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                 85                  90                  95

Tyr Met Asp Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
        130                 135
```

<210> SEQ ID NO 75
<211> LENGTH: 139
<212> TYPE: PRT
<213> ORGANISM: Artificial Sequence
<220> FEATURE:
<223> OTHER INFORMATION: synthetic sequence

<400> SEQUENCE: 75

```
Met Arg Ala Trp Ile Phe Phe Leu Leu Cys Leu Ala Gly Arg Ala Leu
  1               5                  10                  15

Ala Gln Val Gln Leu Val Gln Ser Gly Ala Glu Val Lys Lys Pro Gly
                 20                  25                  30

Ala Ser Val Lys Val Ser Cys Lys Ala Ser Gly Tyr Thr Phe Thr Ser
             35                  40                  45

Tyr Trp Met His Trp Val Arg Gln Ala Pro Gly Gln Gly Leu Glu Trp
         50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                 85                  90                  95

Tyr Met Glu Leu Ser Ser Leu Arg Ser Asp Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
        130                 135
```

<210> SEQ ID NO 76
<211> LENGTH: 139
<212> TYPE: PRT
<213> ORGANISM: Artificial Sequence
<220> FEATURE:
<223> OTHER INFORMATION: synthetic sequence

<400> SEQUENCE: 76

```
Met Arg Ala Trp Ile Phe Phe Leu Leu Cys Leu Ala Gly Arg Ala Leu
  1               5                  10                  15

Ala Gln Val Gln Leu Val Gln Ser Gly Ala Glu Val Lys Lys Pro Gly
                 20                  25                  30

Ala Ser Val Lys Val Ser Cys Lys Ala Ser Gly Tyr Thr Phe Thr Ser
             35                  40                  45

Tyr Phe Met His Trp Val Arg Gln Ala Pro Gly Gln Gly Leu Glu Trp
         50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
```

```
                    85                  90                  95
Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 77
<211> LENGTH: 139
<212> TYPE: PRT
<213> ORGANISM: Artificial Sequence
<220> FEATURE:
<223> OTHER INFORMATION: synthetic sequence

<400> SEQUENCE: 77

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Gly
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 78
<211> LENGTH: 139
<212> TYPE: PRT
<213> ORGANISM: Artificial Sequence
<220> FEATURE:
<223> OTHER INFORMATION: synthetic sequence

<400> SEQUENCE: 78

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ala
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110
```

Cys Ala Arg Pro Leu Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 79
<211> LENGTH: 139
<212> TYPE: PRT
<213> ORGANISM: Artificial Sequence
<220> FEATURE:
<223> OTHER INFORMATION: synthetic sequence

<400> SEQUENCE: 79

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Asn
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 80
<211> LENGTH: 139
<212> TYPE: PRT
<213> ORGANISM: Artificial Sequence
<220> FEATURE:
<223> OTHER INFORMATION: synthetic sequence

<400> SEQUENCE: 80

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Thr
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 81
<211> LENGTH: 139
<212> TYPE: PRT
<213> ORGANISM: Artificial Sequence
<220> FEATURE:
<223> OTHER INFORMATION: synthetic sequence

<400> SEQUENCE: 81

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

His Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 82
<211> LENGTH: 139
<212> TYPE: PRT
<213> ORGANISM: Artificial Sequence
<220> FEATURE:
<223> OTHER INFORMATION: synthetic sequence

<400> SEQUENCE: 82

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln His Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 83
<211> LENGTH: 139
<212> TYPE: PRT

<213> ORGANISM: Artificial Sequence
<220> FEATURE:
<223> OTHER INFORMATION: synthetic sequence

<400> SEQUENCE: 83

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Ile Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
130                 135

<210> SEQ ID NO 84
<211> LENGTH: 139
<212> TYPE: PRT
<213> ORGANISM: Artificial Sequence
<220> FEATURE:
<223> OTHER INFORMATION: synthetic sequence

<400> SEQUENCE: 84

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Asn Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
130                 135

<210> SEQ ID NO 85
<211> LENGTH: 139
<212> TYPE: PRT
<213> ORGANISM: Artificial Sequence
<220> FEATURE:
<223> OTHER INFORMATION: synthetic sequence

<400> SEQUENCE: 85

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Thr Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
        130                 135

<210> SEQ ID NO 86
<211> LENGTH: 139
<212> TYPE: PRT
<213> ORGANISM: Artificial Sequence
<220> FEATURE:
<223> OTHER INFORMATION: synthetic sequence

<400> SEQUENCE: 86

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Arg Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
        130                 135

<210> SEQ ID NO 87
<211> LENGTH: 139
<212> TYPE: PRT
<213> ORGANISM: Artificial Sequence
<220> FEATURE:
<223> OTHER INFORMATION: synthetic sequence

<400> SEQUENCE: 87

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly

```
                20                  25                  30

Ala Ser Val Lys Val Ser Cys Lys Ala Ser Gly Tyr Thr Phe Ser Ser
            35                  40                  45

Tyr Trp Met His Trp Val Arg Gln Ala Pro Gly Gln Gly Leu Glu Trp
        50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
               100                 105                 110

Cys Ala Arg Pro Leu Tyr Tyr Val Thr Ser Pro Thr Leu Leu
               115                 120                 125

Trp Gly Gln Gly Thr Leu Val Thr Val Ser Ser
       130                 135

<210> SEQ ID NO 88
<211> LENGTH: 139
<212> TYPE: PRT
<213> ORGANISM: Artificial Sequence
<220> FEATURE:
<223> OTHER INFORMATION: synthetic sequence

<400> SEQUENCE: 88

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
                20                  25                  30

Ala Ser Val Lys Val Ser Cys Lys Ala Ser Gly Tyr Thr Phe His Ser
            35                  40                  45

Tyr Trp Met His Trp Val Arg Gln Ala Pro Gly Gln Gly Leu Glu Trp
        50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
               100                 105                 110

Cys Ala Arg Pro Leu Tyr Tyr Val Thr Ser Pro Thr Leu Leu
               115                 120                 125

Trp Gly Gln Gly Thr Leu Val Thr Val Ser Ser
       130                 135

<210> SEQ ID NO 89
<211> LENGTH: 139
<212> TYPE: PRT
<213> ORGANISM: Artificial Sequence
<220> FEATURE:
<223> OTHER INFORMATION: synthetic sequence

<400> SEQUENCE: 89

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
                20                  25                  30

Ala Ser Val Lys Val Ser Cys Lys Ala Ser Gly Tyr Thr Phe Thr Ser
            35                  40                  45
```

Tyr Trp Met His Trp Val Arg Gln Ala Pro Gly Gln Gly Leu Glu Trp
            50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Ser Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 90
<211> LENGTH: 139
<212> TYPE: PRT
<213> ORGANISM: Artificial Sequence
<220> FEATURE:
<223> OTHER INFORMATION: synthetic sequence

<400> SEQUENCE: 90

Met Arg Ala Trp Ile Phe Phe Leu Leu Cys Leu Ala Gly Arg Ala Leu
  1               5                  10                  15

Ala Gln Val Gln Leu Val Gln Ser Gly Ala Glu Val Lys Lys Pro Gly
             20                  25                  30

Ala Ser Val Lys Val Ser Cys Lys Ala Ser Gly Tyr Thr Phe Thr Ser
            35                  40                  45

Tyr Trp Met His Trp Val Arg Gln Ala Pro Gly Gln Gly Leu Glu Trp
            50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                85                  90                  95

Tyr Met Glu Leu Ser Ser Leu Thr Ser Glu Asp Thr Ala Val Tyr Tyr
            100                 105                 110

Cys Ala Arg Pro Leu Tyr Tyr Val Thr Ser Pro Pro Thr Leu Leu
            115                 120                 125

Trp Gly Gln Gly Thr Leu Val Thr Val Ser Ser
            130                 135

<210> SEQ ID NO 91
<211> LENGTH: 139
<212> TYPE: PRT
<213> ORGANISM: Artificial Sequence
<220> FEATURE:
<223> OTHER INFORMATION: synthetic sequence

<400> SEQUENCE: 91

Met Arg Ala Trp Ile Phe Phe Leu Leu Cys Leu Ala Gly Arg Ala Leu
  1               5                  10                  15

Ala Gln Val Gln Leu Val Gln Ser Gly Ala Glu Val Lys Lys Pro Gly
             20                  25                  30

Ala Ser Val Lys Val Ser Cys Lys Ala Ser Gly Tyr Thr Phe Thr Ser
            35                  40                  45

Tyr Trp Met His Trp Val Arg Gln Ala Pro Gly Gln Gly Leu Glu Trp
            50                  55                  60

Met Gly Thr Ile Tyr Pro Arg Asn Ser Asp Thr Asp Tyr Asn Gln Lys
 65                  70                  75                  80

```
Phe Lys Ala Arg Val Thr Val Thr Arg Asp Thr Ser Thr Ser Thr Val
                85                  90                  95

Tyr Met Glu Leu Ser Ser Leu Arg Ser Glu Asp Thr Ala Val Tyr Tyr
               100                 105                 110

Cys Ala Arg Pro Leu Tyr Tyr Tyr Val Thr Pro Pro Thr Leu Leu
            115                 120                 125

Trp Gly Gln Gly Thr Leu Val Thr Val Ser Ser
    130                 135

<210> SEQ ID NO 92
<211> LENGTH: 139
<212> TYPE: PRT
<213> ORGANISM: Artificial Sequence
<220> FEATURE:
<223> OTHER INFORMATION: synthetic sequence

<400> SEQUENCE: 92

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
                20                  25                  30

Ala Ser Val Lys Val Ser Cys Lys Ala Ser Gly Tyr Asn Phe Thr Ser
            35                  40                  45

Tyr Trp Met His Trp Val Arg Gln Ala Pro Gly Gln Gly Leu Glu Trp
        50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
               100                 105                 110

Cys Ala Arg Pro Leu Tyr Tyr Tyr Val Thr Pro Pro Thr Leu Leu
            115                 120                 125

Trp Gly Gln Gly Thr Leu Val Thr Val Ser Ser
    130                 135

<210> SEQ ID NO 93
<211> LENGTH: 139
<212> TYPE: PRT
<213> ORGANISM: Artificial Sequence
<220> FEATURE:
<223> OTHER INFORMATION: synthetic sequence

<400> SEQUENCE: 93

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
                20                  25                  30

Ala Ser Val Lys Val Ser Cys Lys Ala Ser Gly Tyr Ile Phe Thr Ser
            35                  40                  45

Tyr Trp Met His Trp Val Arg Gln Ala Pro Gly Gln Gly Leu Glu Trp
        50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
```

```
                100                 105                 110
Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 94
<211> LENGTH: 139
<212> TYPE: PRT
<213> ORGANISM: Artificial Sequence
<220> FEATURE:
<223> OTHER INFORMATION: synthetic sequence

<400> SEQUENCE: 94

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Ser Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 95
<211> LENGTH: 139
<212> TYPE: PRT
<213> ORGANISM: Artificial Sequence
<220> FEATURE:
<223> OTHER INFORMATION: synthetic sequence

<400> SEQUENCE: 95

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Phe Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125
```

Trp Gly Gln Gly Thr Leu Val Thr Val Ser Ser
        130                 135

<210> SEQ ID NO 96
<211> LENGTH: 139
<212> TYPE: PRT
<213> ORGANISM: Artificial Sequence
<220> FEATURE:
<223> OTHER INFORMATION: synthetic sequence

<400> SEQUENCE: 96

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Asn Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
        130                 135

<210> SEQ ID NO 97
<211> LENGTH: 139
<212> TYPE: PRT
<213> ORGANISM: Artificial Sequence
<220> FEATURE:
<223> OTHER INFORMATION: synthetic sequence

<400> SEQUENCE: 97

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Leu Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
        130                 135

<210> SEQ ID NO 98

<211> LENGTH: 139
<212> TYPE: PRT
<213> ORGANISM: Artificial Sequence
<220> FEATURE:
<223> OTHER INFORMATION: synthetic sequence

<400> SEQUENCE: 98

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Val Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 99
<211> LENGTH: 139
<212> TYPE: PRT
<213> ORGANISM: Artificial Sequence
<220> FEATURE:
<223> OTHER INFORMATION: synthetic sequence

<400> SEQUENCE: 99

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Phe Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 100
<211> LENGTH: 139
<212> TYPE: PRT
<213> ORGANISM: Artificial Sequence
<220> FEATURE:
<223> OTHER INFORMATION: synthetic sequence

<400> SEQUENCE: 100

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Ile Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 101
<211> LENGTH: 139
<212> TYPE: PRT
<213> ORGANISM: Artificial Sequence
<220> FEATURE:
<223> OTHER INFORMATION: synthetic sequence

<400> SEQUENCE: 101

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Arg
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 102
<211> LENGTH: 139
<212> TYPE: PRT
<213> ORGANISM: Artificial Sequence
<220> FEATURE:
<223> OTHER INFORMATION: synthetic sequence

<400> SEQUENCE: 102

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Asn
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Tyr Val Thr Ser Pro Pro Thr Leu Leu
            115                 120                 125

Trp Gly Gln Gly Thr Leu Val Thr Val Ser Ser
        130                 135

<210> SEQ ID NO 103
<211> LENGTH: 139
<212> TYPE: PRT
<213> ORGANISM: Artificial Sequence
<220> FEATURE:
<223> OTHER INFORMATION: synthetic sequence

<400> SEQUENCE: 103

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Arg Ser Leu Arg Ser Glu Asp Thr Ala Val Tyr Tyr
                100                 105                 110

Cys Ala Arg Pro Leu Tyr Tyr Tyr Val Thr Ser Pro Pro Thr Leu Leu
            115                 120                 125

Trp Gly Gln Gly Thr Leu Val Thr Val Ser Ser
        130                 135

<210> SEQ ID NO 104
<211> LENGTH: 139
<212> TYPE: PRT
<213> ORGANISM: Artificial Sequence
<220> FEATURE:
<223> OTHER INFORMATION: synthetic sequence

<400> SEQUENCE: 104

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

```
                35                  40                  45
Tyr Trp Met His Trp Val Arg Gln Ala Pro Gly Gln Gly Leu Glu Trp
 50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Thr
                 85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Tyr Val Thr Ser Pro Pro Thr Leu Leu
                115                 120                 125

Trp Gly Gln Gly Thr Leu Val Thr Val Ser Ser
                130                 135

<210> SEQ ID NO 105
<211> LENGTH: 139
<212> TYPE: PRT
<213> ORGANISM: Artificial Sequence
<220> FEATURE:
<223> OTHER INFORMATION: synthetic sequence

<400> SEQUENCE: 105

Met Arg Ala Trp Ile Phe Phe Leu Leu Cys Leu Ala Gly Arg Ala Leu
 1               5                  10                  15

Ala Gln Val Gln Leu Val Glu Ser Gly Ala Glu Val Lys Lys Pro Gly
                 20                  25                  30

Ala Ser Val Lys Val Ser Cys Lys Ala Ser Gly Tyr Thr Phe Thr Ser
                 35                  40                  45

Tyr Trp Met His Trp Val Arg Gln Ala Pro Gly Gln Gly Leu Glu Trp
 50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                 85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Tyr Val Thr Ser Pro Pro Thr Leu Leu
                115                 120                 125

Trp Gly Gln Gly Thr Leu Val Thr Val Ser Ser
                130                 135

<210> SEQ ID NO 106
<211> LENGTH: 139
<212> TYPE: PRT
<213> ORGANISM: Artificial Sequence
<220> FEATURE:
<223> OTHER INFORMATION: synthetic sequence

<400> SEQUENCE: 106

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
                 20                  25                  30

Ala Ser Val Lys Val Ser Cys Lys Ala Ser Gly Tyr Thr Phe Thr Asp
                 35                  40                  45

Tyr Trp Met His Trp Val Arg Gln Ala Pro Gly Gln Gly Leu Glu Trp
 50                  55                  60
```

```
Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Ser Thr Val
                 85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
            115                 120                 125

Trp Gly Gln Gly Thr Leu Val Thr Val Ser Ser
        130                 135

<210> SEQ ID NO 107
<211> LENGTH: 139
<212> TYPE: PRT
<213> ORGANISM: Artificial Sequence
<220> FEATURE:
<223> OTHER INFORMATION: synthetic sequence

<400> SEQUENCE: 107

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
         35                  40                  45

Tyr Trp Ile His Trp Val Arg Gln Ala Pro Gly Gln Gly Leu Glu Trp
     50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Ser Thr Val
                 85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
            115                 120                 125

Trp Gly Gln Gly Thr Leu Val Thr Val Ser Ser
        130                 135

<210> SEQ ID NO 108
<211> LENGTH: 139
<212> TYPE: PRT
<213> ORGANISM: Artificial Sequence
<220> FEATURE:
<223> OTHER INFORMATION: synthetic sequence

<400> SEQUENCE: 108

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
         35                  40                  45

Tyr Trp Leu His Trp Val Arg Gln Ala Pro Gly Gln Gly Leu Glu Trp
     50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Ser Thr Val
                 85                  90                  95
```

Tyr Met Glu Leu Ser Ser Leu Arg Ser Glu Asp Thr Ala Val Tyr Tyr
                100                 105                 110

Cys Ala Arg Pro Leu Tyr Tyr Val Thr Ser Pro Pro Thr Leu Leu
            115                 120                 125

Trp Gly Gln Gly Thr Leu Val Thr Val Ser Ser
        130                 135

<210> SEQ ID NO 109
<211> LENGTH: 139
<212> TYPE: PRT
<213> ORGANISM: Artificial Sequence
<220> FEATURE:
<223> OTHER INFORMATION: synthetic sequence

<400> SEQUENCE: 109

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met Asn Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Val Thr Ser Pro Pro Thr Leu Leu
            115                 120                 125

Trp Gly Gln Gly Thr Leu Val Thr Val Ser Ser
        130                 135

<210> SEQ ID NO 110
<211> LENGTH: 139
<212> TYPE: PRT
<213> ORGANISM: Artificial Sequence
<220> FEATURE:
<223> OTHER INFORMATION: synthetic sequence

<400> SEQUENCE: 110

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp His Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Val Thr Ser Pro Pro Thr Leu Leu

<210> SEQ ID NO 111
<211> LENGTH: 139
<212> TYPE: PRT
<213> ORGANISM: Artificial Sequence
<220> FEATURE:
<223> OTHER INFORMATION: synthetic sequence

<400> SEQUENCE: 111

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Phe Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 112
<211> LENGTH: 139
<212> TYPE: PRT
<213> ORGANISM: Artificial Sequence
<220> FEATURE:
<223> OTHER INFORMATION: synthetic sequence

<400> SEQUENCE: 112

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Ile Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 113
<211> LENGTH: 139
<212> TYPE: PRT
<213> ORGANISM: Artificial Sequence
<220> FEATURE:
<223> OTHER INFORMATION: synthetic sequence

<400> SEQUENCE: 113

```
Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

His Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Ile Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135
```

<210> SEQ ID NO 114
<211> LENGTH: 139
<212> TYPE: PRT
<213> ORGANISM: Artificial Sequence
<220> FEATURE:
<223> OTHER INFORMATION: synthetic sequence

<400> SEQUENCE: 114

```
Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Ile Thr Ser Pro Pro Thr Leu Leu
        115                 120                 125

Trp Gly Gln Gly Thr Leu Val Thr Val Ser Ser
    130                 135
```

<210> SEQ ID NO 115
<211> LENGTH: 139
<212> TYPE: PRT
<213> ORGANISM: Artificial Sequence
<220> FEATURE:
<223> OTHER INFORMATION: synthetic sequence

<400> SEQUENCE: 115

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Leu Thr Ser Pro Pro Thr Leu Leu
        115                 120                 125

Trp Gly Gln Gly Thr Leu Val Thr Val Ser Ser
    130                 135

<210> SEQ ID NO 116
<211> LENGTH: 139
<212> TYPE: PRT
<213> ORGANISM: Artificial Sequence
<220> FEATURE:
<223> OTHER INFORMATION: synthetic sequence

<400> SEQUENCE: 116

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Leu Thr Ser Pro Pro Thr Leu Leu
        115                 120                 125

Trp Gly Gln Gly Thr Leu Val Thr Val Ser Ser
    130                 135

<210> SEQ ID NO 117
<211> LENGTH: 139
<212> TYPE: PRT
<213> ORGANISM: Artificial Sequence
<220> FEATURE:
<223> OTHER INFORMATION: synthetic sequence

<400> SEQUENCE: 117

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Asp Thr Ser Pro Pro Thr Leu Leu
            115                 120                 125

Trp Gly Gln Gly Thr Leu Val Thr Val Ser Ser
        130                 135

<210> SEQ ID NO 118
<211> LENGTH: 139
<212> TYPE: PRT
<213> ORGANISM: Artificial Sequence
<220> FEATURE:
<223> OTHER INFORMATION: synthetic sequence

<400> SEQUENCE: 118

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Phe Thr Ser Pro Pro Thr Leu Leu
            115                 120                 125

Trp Gly Gln Gly Thr Leu Val Thr Val Ser Ser
        130                 135

<210> SEQ ID NO 119
<211> LENGTH: 139
<212> TYPE: PRT
<213> ORGANISM: Artificial Sequence
<220> FEATURE:
<223> OTHER INFORMATION: synthetic sequence

<400> SEQUENCE: 119

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

```
Ala Ser Val Lys Val Ser Cys Lys Ala Ser Gly Tyr Thr Phe Thr Ser
            35                  40                  45

Tyr Trp Met His Trp Val Arg Gln Ala Pro Gly Gln Gly Leu Glu Trp
 50                      55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Ala Thr Ser Pro Pro Thr Leu Leu
                115                 120                 125

Trp Gly Gln Gly Thr Leu Val Thr Val Ser Ser
        130                 135

<210> SEQ ID NO 120
<211> LENGTH: 139
<212> TYPE: PRT
<213> ORGANISM: Artificial Sequence
<220> FEATURE:
<223> OTHER INFORMATION: synthetic sequence

<400> SEQUENCE: 120

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
                20                  25                  30

Ala Ser Val Lys Val Ser Cys Lys Ala Ser Gly Tyr Thr Phe Thr Ser
            35                  40                  45

Tyr Trp Met His Trp Val Arg Gln Ala Pro Gly Gln Gly Leu Glu Trp
 50                      55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Gly Thr Ser Pro Pro Thr Leu Leu
                115                 120                 125

Trp Gly Gln Gly Thr Leu Val Thr Val Ser Ser
        130                 135

<210> SEQ ID NO 121
<211> LENGTH: 139
<212> TYPE: PRT
<213> ORGANISM: Artificial Sequence
<220> FEATURE:
<223> OTHER INFORMATION: synthetic sequence

<400> SEQUENCE: 121

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
                20                  25                  30

Ala Ser Val Lys Val Ser Cys Lys Ala Ser Gly Tyr Thr Phe Thr Ser
            35                  40                  45

Tyr Trp Met His Trp Val Arg Gln Ala Pro Gly Gln Gly Leu Glu Trp
```

```
                    50                  55                  60
Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                     85                  90                  95

Tyr Met Glu Leu Ser Ser Leu Arg Ser Glu Asp Thr Ala Val Tyr Tyr
                    100                 105                 110

Cys Ala Arg Pro Leu Tyr Tyr Tyr Val Thr Ser Pro Pro Thr Leu Phe
                115                 120                 125

Trp Gly Gln Gly Thr Leu Val Thr Val Ser Ser
            130                 135

<210> SEQ ID NO 122
<211> LENGTH: 139
<212> TYPE: PRT
<213> ORGANISM: Artificial Sequence
<220> FEATURE:
<223> OTHER INFORMATION: synthetic sequence

<400> SEQUENCE: 122

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
                 20                  25                  30

Ala Ser Val Lys Val Ser Cys Lys Ala Ser Gly Tyr Thr Phe Thr Ser
             35                  40                  45

Tyr Trp Met His Trp Val Arg Gln Ala Pro Gly Gln Gly Leu Glu Trp
         50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                     85                  90                  95

Tyr Met Glu Leu Ser Ser Leu Arg Ser Glu Asp Thr Ala Val Tyr Tyr
                    100                 105                 110

Cys Ala Arg Pro Leu Tyr Tyr Tyr Val Thr Ser Pro Pro Thr Leu Val
                115                 120                 125

Trp Gly Gln Gly Thr Leu Val Thr Val Ser Ser
            130                 135

<210> SEQ ID NO 123
<211> LENGTH: 139
<212> TYPE: PRT
<213> ORGANISM: Artificial Sequence
<220> FEATURE:
<223> OTHER INFORMATION: synthetic sequence

<400> SEQUENCE: 123

Met Arg Ala Trp Ile Phe Phe Leu Leu Cys Leu Ala Gly Arg Ala Leu
 1               5                  10                  15

Ala Gln Val Gln Leu Val Gln Ser Gly Ala Glu Val Lys Lys Pro Gly
                 20                  25                  30

Ala Ser Val Lys Val Ser Cys Lys Ala Ser Gly Tyr Thr Phe Thr Ser
             35                  40                  45

Tyr Trp Met His Trp Val Arg Gln Ala Pro Gly Gln Gly Leu Glu Trp
         50                  55                  60

Met Gly Thr Ile Tyr Pro Arg Asn Ser Asp Thr Asp Tyr Asn Gln Lys
 65                  70                  75                  80
```

```
Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Pro
        115                 120                 125

Trp Gly Gln Gly Thr Leu Val Thr Val Ser Ser
    130                 135

<210> SEQ ID NO 124
<211> LENGTH: 139
<212> TYPE: PRT
<213> ORGANISM: Artificial Sequence
<220> FEATURE:
<223> OTHER INFORMATION: synthetic sequence

<400> SEQUENCE: 124

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Leu Thr Ser Pro Pro Thr Leu Phe
        115                 120                 125

Trp Gly Gln Gly Thr Leu Val Thr Val Ser Ser
    130                 135

<210> SEQ ID NO 125
<211> LENGTH: 139
<212> TYPE: PRT
<213> ORGANISM: Artificial Sequence
<220> FEATURE:
<223> OTHER INFORMATION: synthetic sequence

<400> SEQUENCE: 125

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asn Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110
```

```
Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
        130                 135
```

<210> SEQ ID NO 126
<211> LENGTH: 139
<212> TYPE: PRT
<213> ORGANISM: Artificial Sequence
<220> FEATURE:
<223> OTHER INFORMATION: synthetic sequence

<400> SEQUENCE: 126

```
Met Arg Ala Trp Ile Phe Phe Leu Leu Cys Leu Ala Gly Arg Ala Leu
1               5                   10                  15

Ala Gln Val Gln Leu Met Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
        130                 135
```

<210> SEQ ID NO 127
<211> LENGTH: 139
<212> TYPE: PRT
<213> ORGANISM: Artificial Sequence
<220> FEATURE:
<223> OTHER INFORMATION: synthetic sequence

<400> SEQUENCE: 127

```
Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Phe
        115                 120                 125

Trp Gly Gln Gly Thr Leu Val Thr Val Ser Ser
```

<210> SEQ ID NO 128
<211> LENGTH: 139
<212> TYPE: PRT
<213> ORGANISM: Artificial Sequence
<220> FEATURE:
<223> OTHER INFORMATION: synthetic sequence

<400> SEQUENCE: 128

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Ile Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 129
<211> LENGTH: 139
<212> TYPE: PRT
<213> ORGANISM: Artificial Sequence
<220> FEATURE:
<223> OTHER INFORMATION: synthetic sequence

<400> SEQUENCE: 129

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Ile Ser Pro Pro Thr Leu Leu
        115                 120                 125

Trp Gly Gln Gly Thr Leu Val Thr Val Ser Ser
    130                 135

<210> SEQ ID NO 130
<211> LENGTH: 139

<212> TYPE: PRT
<213> ORGANISM: Artificial Sequence
<220> FEATURE:
<223> OTHER INFORMATION: synthetic sequence

<400> SEQUENCE: 130

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 131
<211> LENGTH: 139
<212> TYPE: PRT
<213> ORGANISM: Artificial Sequence
<220> FEATURE:
<223> OTHER INFORMATION: synthetic sequence

<400> SEQUENCE: 131

Met Arg Ala Trp Ile Phe Phe Leu Leu Cys Leu Ala Gly Arg Ala Leu
1               5                   10                  15

Ala Gln Val Gln Leu Met Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asn Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Leu Thr Ser Pro Pro Thr Leu Phe
        115                 120                 125

Trp Gly Gln Gly Thr Leu Val Thr Val Ser Ser
    130                 135

<210> SEQ ID NO 132
<211> LENGTH: 139
<212> TYPE: PRT
<213> ORGANISM: Artificial Sequence
<220> FEATURE:
<223> OTHER INFORMATION: synthetic sequence -continued

```
<400> SEQUENCE: 132

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Met Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Phe
        115                 120                 125

Trp Gly Gln Gly Thr Leu Val Thr Val Ser Ser
    130                 135

<210> SEQ ID NO 133
<211> LENGTH: 139
<212> TYPE: PRT
<213> ORGANISM: Artificial Sequence
<220> FEATURE:
<223> OTHER INFORMATION: synthetic sequence

<400> SEQUENCE: 133

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Met Arg Gln Ala Pro Gly Gln Gly Leu Glu Trp
    50                  55                  60

Met Gly Thr Ile Tyr Pro Arg Asn Ser Asp Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Leu
        115                 120                 125

Trp Gly Gln Gly Thr Leu Val Thr Val Ser Ser
    130                 135

<210> SEQ ID NO 134
<211> LENGTH: 139
<212> TYPE: PRT
<213> ORGANISM: Artificial Sequence
<220> FEATURE:
<223> OTHER INFORMATION: synthetic sequence

<400> SEQUENCE: 134

Met Arg Ala Trp Ile Phe Phe Leu Leu Cys Leu Ala Gly Arg Ala Leu
1               5                   10                  15
```

Ala Gln Val Gln Leu Met Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
 50                  55                  60

Met Gly Thr Ile Tyr Pro Arg Asn Ser Asn Thr Asp Tyr Asn Gln Lys
 65                  70                  75                  80

Phe Lys Ala Arg Val Thr Met Thr Arg Asp Thr Ser Ser Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Leu Thr Ser Pro Pro Thr Leu Leu
            115                 120                 125

Trp Gly Gln Gly Thr Leu Val Thr Val Ser Ser
            130                 135

<210> SEQ ID NO 135
<211> LENGTH: 139
<212> TYPE: PRT
<213> ORGANISM: Artificial Sequence
<220> FEATURE:
<223> OTHER INFORMATION: synthetic sequence

<400> SEQUENCE: 135

Met Arg Ala Trp Ile Phe Phe Leu Leu Cys Leu Ala Gly Arg Ala Leu
1               5                   10                  15

Ala Gln Val Gln Leu Met Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
 50                  55                  60

Met Gly Thr Ile Tyr Pro Arg Asn Ser Asn Thr Asp Tyr Asn Gln Lys
 65                  70                  75                  80

Phe Lys Ala Arg Val Thr Met Thr Arg Asp Thr Ser Ser Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Val Thr Ser Pro Pro Thr Leu Phe
            115                 120                 125

Trp Gly Gln Gly Thr Leu Val Thr Val Ser Ser
            130                 135

<210> SEQ ID NO 136
<211> LENGTH: 139
<212> TYPE: PRT
<213> ORGANISM: Artificial Sequence
<220> FEATURE:
<223> OTHER INFORMATION: synthetic sequence

<400> SEQUENCE: 136

Met Arg Ala Trp Ile Phe Phe Leu Leu Cys Leu Ala Gly Arg Ala Leu
1               5                   10                  15

Ala Gln Val Gln Leu Met Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

```
Tyr Trp Met His Trp Val Arg Gln Ala Pro Gly Gln Gly Leu Glu Trp
         50                  55                  60

Met Gly Thr Ile Tyr Pro Arg Asn Ser Asn Thr Asp Tyr Asn Gln Lys
 65                  70                  75                  80

Phe Lys Ala Arg Val Thr Met Thr Arg Asp Thr Ser Thr Ser Thr Val
                 85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Tyr Leu Thr Ser Pro Pro Thr Leu Phe
            115                 120                 125

Trp Gly Gln Gly Thr Leu Val Thr Val Ser Ser
        130                 135

<210> SEQ ID NO 137
<211> LENGTH: 139
<212> TYPE: PRT
<213> ORGANISM: Artificial Sequence
<220> FEATURE:
<223> OTHER INFORMATION: synthetic sequence

<400> SEQUENCE: 137

Met Arg Ala Trp Ile Phe Phe Leu Leu Cys Leu Ala Gly Arg Ala Leu
  1               5                  10                  15

Ala Gln Val Gln Leu Met Gln Ser Gly Ala Glu Val Lys Lys Pro Gly
             20                  25                  30

Ala Ser Val Lys Val Ser Cys Lys Ala Ser Gly Tyr Thr Phe Thr Ser
         35                  40                  45

Tyr Trp Met His Trp Met Arg Gln Ala Pro Gly Gln Gly Leu Glu Trp
         50                  55                  60

Met Gly Thr Ile Tyr Pro Arg Asn Ser Asn Thr Asp Tyr Asn Gln Lys
 65                  70                  75                  80

Phe Lys Ala Arg Val Thr Met Thr Arg Asp Thr Ser Thr Ser Thr Val
                 85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Tyr Leu Thr Ser Pro Pro Thr Leu Phe
            115                 120                 125

Trp Gly Gln Gly Thr Leu Val Thr Val Ser Ser
        130                 135

<210> SEQ ID NO 138
<211> LENGTH: 139
<212> TYPE: PRT
<213> ORGANISM: Artificial Sequence
<220> FEATURE:
<223> OTHER INFORMATION: synthetic sequence

<400> SEQUENCE: 138

Met Arg Ala Trp Ile Phe Phe Leu Leu Cys Leu Ala Gly Arg Ala Leu
  1               5                  10                  15

Ala Gln Val Gln Leu Met Gln Ser Gly Ala Glu Val Lys Lys Pro Gly
             20                  25                  30

Ala Ser Val Lys Val Ser Cys Lys Ala Ser Gly Tyr Thr Phe Thr Ser
         35                  40                  45

Tyr Trp Met His Trp Met Arg Gln Ala Pro Gly Gln Gly Leu Glu Trp
         50                  55                  60

Met Gly Thr Ile Tyr Pro Arg Asn Ser Asn Thr Asp Tyr Asn Gln Lys
```

```
                65                  70                  75                  80
Phe Lys Ala Arg Val Thr Met Thr Arg Asp Thr Ser Thr Ser Thr Val
                    85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Leu Thr Ser Pro Pro Thr Leu Leu
                115                 120                 125

Trp Gly Gln Gly Thr Leu Val Thr Val Ser Ser
        130                 135

<210> SEQ ID NO 139
<211> LENGTH: 139
<212> TYPE: PRT
<213> ORGANISM: Artificial Sequence
<220> FEATURE:
<223> OTHER INFORMATION: synthetic sequence

<400> SEQUENCE: 139

Met Arg Ala Trp Ile Phe Phe Leu Leu Cys Leu Ala Gly Arg Ala Leu
1               5                   10                  15

Ala Gln Val Gln Leu Met Gln Ser Gly Ala Glu Val Lys Lys Pro Gly
                20                  25                  30

Ala Ser Val Lys Val Ser Cys Lys Ala Ser Gly Tyr Thr Phe Thr Ser
            35                  40                  45

Tyr Trp Met His Trp Met Arg Gln Ala Pro Gly Gln Gly Leu Glu Trp
        50                  55                  60

Met Gly Thr Ile Tyr Pro Arg Asn Ser Asn Thr Asp Tyr Asn Gln Lys
65                  70                  75                  80

Phe Lys Ala Arg Val Thr Met Thr Arg Asp Thr Ser Thr Ser Thr Val
                    85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Val Thr Ser Pro Pro Thr Leu Phe
                115                 120                 125

Trp Gly Gln Gly Thr Leu Val Thr Val Ser Ser
        130                 135

<210> SEQ ID NO 140
<211> LENGTH: 139
<212> TYPE: PRT
<213> ORGANISM: Artificial Sequence
<220> FEATURE:
<223> OTHER INFORMATION: synthetic sequence

<400> SEQUENCE: 140

Met Arg Ala Trp Ile Phe Phe Leu Leu Cys Leu Ala Gly Arg Ala Leu
1               5                   10                  15

Ala Gln Val Gln Leu Met Gln Ser Gly Ala Glu Val Lys Lys Pro Gly
                20                  25                  30

Ala Ser Val Lys Val Ser Cys Lys Ala Ser Gly Tyr Thr Phe Thr Ser
            35                  40                  45

Tyr Trp Met His Trp Met Arg Gln Ala Pro Gly Gln Gly Leu Glu Trp
        50                  55                  60

Met Gly Thr Ile Tyr Pro Arg Asn Ser Asn Thr Asp Tyr Asn Gln Lys
65                  70                  75                  80

Phe Lys Ala Arg Val Thr Met Thr Arg Asp Thr Ser Thr Ser Thr Val
                    85                  90                  95
```

```
Tyr Met Glu Leu Ser Ser Leu Arg Ser Glu Asp Thr Ala Val Tyr Tyr
                100                 105                 110

Cys Ala Arg Pro Leu Tyr Tyr Leu Thr Ser Pro Pro Thr Leu Phe
        115                 120                 125

Trp Gly Gln Gly Thr Leu Val Thr Val Ser Ser
    130                 135

<210> SEQ ID NO 141
<211> LENGTH: 125
<212> TYPE: PRT
<213> ORGANISM: Artificial Sequence
<220> FEATURE:
<223> OTHER INFORMATION: synthetic sequence

<400> SEQUENCE: 141

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Cys Asn Ser Tyr Pro
            100                 105                 110

Phe Thr Phe Gly Ser Gly Thr Lys Leu Glu Ile Lys Arg
        115                 120                 125

<210> SEQ ID NO 142
<211> LENGTH: 125
<212> TYPE: PRT
<213> ORGANISM: Artificial Sequence
<220> FEATURE:
<223> OTHER INFORMATION: synthetic sequence

<400> SEQUENCE: 142

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
        115                 120                 125

<210> SEQ ID NO 143
```

<211> LENGTH: 125
<212> TYPE: PRT
<213> ORGANISM: Artificial Sequence
<220> FEATURE:
<223> OTHER INFORMATION: synthetic sequence

<400> SEQUENCE: 143

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Asn Ser Tyr Pro
            100                 105                 110

Phe Thr Phe Gly Ser Gly Thr Lys Leu Glu Ile Lys Arg
        115                 120                 125

<210> SEQ ID NO 144
<211> LENGTH: 125
<212> TYPE: PRT
<213> ORGANISM: Artificial Sequence
<220> FEATURE:
<223> OTHER INFORMATION: synthetic sequence

<400> SEQUENCE: 144

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Asn Ser Tyr Pro
            100                 105                 110

Phe Thr Phe Gly Ser Gly Thr Lys Leu Glu Ile Lys Arg
        115                 120                 125

<210> SEQ ID NO 145
<211> LENGTH: 125
<212> TYPE: PRT
<213> ORGANISM: Artificial Sequence
<220> FEATURE:
<223> OTHER INFORMATION: synthetic sequence

<400> SEQUENCE: 145

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Val Asn Ser Tyr Pro
            100                 105                 110

Phe Thr Phe Gly Ser Gly Thr Lys Leu Glu Ile Lys Arg
        115                 120                 125

<210> SEQ ID NO 146
<211> LENGTH: 125
<212> TYPE: PRT
<213> ORGANISM: Artificial Sequence
<220> FEATURE:
<223> OTHER INFORMATION: synthetic sequence

<400> SEQUENCE: 146

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ile Asn Ser Tyr Pro
            100                 105                 110

Phe Thr Phe Gly Ser Gly Thr Lys Leu Glu Ile Lys Arg
        115                 120                 125

<210> SEQ ID NO 147
<211> LENGTH: 125
<212> TYPE: PRT
<213> ORGANISM: Artificial Sequence
<220> FEATURE:
<223> OTHER INFORMATION: synthetic sequence

<400> SEQUENCE: 147

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Leu Asn Ser Tyr Pro
            100                 105                 110

Phe Thr Phe Gly Ser Gly Thr Lys Leu Glu Ile Lys Arg
        115                 120                 125

<210> SEQ ID NO 148
<211> LENGTH: 125
<212> TYPE: PRT
<213> ORGANISM: Artificial Sequence
<220> FEATURE:
<223> OTHER INFORMATION: synthetic sequence

<400> SEQUENCE: 148

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Asn Ser Tyr Pro
            100                 105                 110

Phe Thr Phe Gly Ser Gly Thr Lys Leu Glu Ile Lys Arg
        115                 120                 125

<210> SEQ ID NO 149
<211> LENGTH: 125
<212> TYPE: PRT
<213> ORGANISM: Artificial Sequence
<220> FEATURE:
<223> OTHER INFORMATION: synthetic sequence

<400> SEQUENCE: 149

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ser Asn Ser Tyr Pro
            100                 105                 110

Phe Thr Phe Gly Ser Gly Thr Lys Leu Glu Ile Lys Arg
        115                 120                 125

-continued

```
<210> SEQ ID NO 150
<211> LENGTH: 125
<212> TYPE: PRT
<213> ORGANISM: Artificial Sequence
<220> FEATURE:
<223> OTHER INFORMATION: synthetic sequence

<400> SEQUENCE: 150

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Ser Thr Tyr Pro
            100                 105                 110

Phe Thr Phe Gly Ser Gly Thr Lys Leu Glu Ile Lys Arg
        115                 120                 125

<210> SEQ ID NO 151
<211> LENGTH: 125
<212> TYPE: PRT
<213> ORGANISM: Artificial Sequence
<220> FEATURE:
<223> OTHER INFORMATION: synthetic sequence

<400> SEQUENCE: 151

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Ser Ala Tyr Pro
            100                 105                 110

Phe Thr Phe Gly Ser Gly Thr Lys Leu Glu Ile Lys Arg
        115                 120                 125

<210> SEQ ID NO 152
<211> LENGTH: 125
<212> TYPE: PRT
<213> ORGANISM: Artificial Sequence
<220> FEATURE:
<223> OTHER INFORMATION: synthetic sequence

<400> SEQUENCE: 152

Met Arg Ala Trp Ile Phe Phe Leu Leu Cys Leu Ala Gly Arg Ala Leu
1               5                   10                  15
```

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Arg Thr Tyr Pro
            100                 105                 110

Phe Thr Phe Gly Ser Gly Thr Lys Leu Glu Ile Lys Arg
        115                 120                 125

<210> SEQ ID NO 153
<211> LENGTH: 125
<212> TYPE: PRT
<213> ORGANISM: Artificial Sequence
<220> FEATURE:
<223> OTHER INFORMATION: synthetic sequence

<400> SEQUENCE: 153

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Arg Ala Tyr Pro
            100                 105                 110

Phe Thr Phe Gly Ser Gly Thr Lys Leu Glu Ile Lys Arg
        115                 120                 125

<210> SEQ ID NO 154
<211> LENGTH: 125
<212> TYPE: PRT
<213> ORGANISM: Artificial Sequence
<220> FEATURE:
<223> OTHER INFORMATION: synthetic sequence

<400> SEQUENCE: 154

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser

```
                65                  70                  75                  80
Gly Ser Gly Ser Gly Thr Glu Phe Thr Leu Thr Ile Ser Ser Leu Gln
                    85                  90                  95

Pro Glu Asp Phe Ala Thr Tyr Tyr Cys Gln Gln Ala Lys Thr Tyr Pro
                100                 105                 110

Phe Thr Phe Gly Ser Gly Thr Lys Leu Glu Ile Lys Arg
                115                 120                 125

<210> SEQ ID NO 155
<211> LENGTH: 125
<212> TYPE: PRT
<213> ORGANISM: Artificial Sequence
<220> FEATURE:
<223> OTHER INFORMATION: synthetic sequence

<400> SEQUENCE: 155

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
                20                  25                  30

Gly Asp Arg Val Thr Ile Thr Cys Lys Ala Ser Gln Asp Val Gly Thr
                35                  40                  45

Ala Val Ala Trp Tyr Gln Gln Lys Pro Gly Lys Ala Pro Lys Leu Leu
        50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                    85                  90                  95

Pro Glu Asp Phe Ala Thr Tyr Tyr Cys Gln Gln Ala Lys Ala Tyr Pro
                100                 105                 110

Phe Thr Phe Gly Ser Gly Thr Lys Leu Glu Ile Lys Arg
                115                 120                 125

<210> SEQ ID NO 156
<211> LENGTH: 125
<212> TYPE: PRT
<213> ORGANISM: Artificial Sequence
<220> FEATURE:
<223> OTHER INFORMATION: synthetic sequence

<400> SEQUENCE: 156

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
                20                  25                  30

Gly Asp Arg Val Thr Ile Thr Cys Lys Ala Ser Gln Asp Val Gly Thr
                35                  40                  45

Ala Val Ala Trp Tyr Gln Gln Lys Pro Gly Lys Ala Pro Lys Leu Leu
        50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                    85                  90                  95

Pro Glu Asp Phe Ala Thr Tyr Tyr Cys Gln Gln Ala Gln Thr Tyr Pro
                100                 105                 110

Phe Thr Phe Gly Ser Gly Thr Lys Leu Glu Ile Lys Arg
                115                 120                 125
```

<210> SEQ ID NO 157
<211> LENGTH: 125
<212> TYPE: PRT
<213> ORGANISM: Artificial Sequence
<220> FEATURE:
<223> OTHER INFORMATION: synthetic sequence

<400> SEQUENCE: 157

```
Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Gln Ala Tyr Pro
            100                 105                 110

Phe Thr Phe Gly Ser Gly Thr Lys Leu Glu Ile Lys Arg
        115                 120                 125
```

<210> SEQ ID NO 158
<211> LENGTH: 125
<212> TYPE: PRT
<213> ORGANISM: Artificial Sequence
<220> FEATURE:
<223> OTHER INFORMATION: synthetic sequence

<400> SEQUENCE: 158

```
Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Tyr Ser Tyr Pro
            100                 105                 110

Phe Thr Phe Gly Ser Gly Thr Lys Leu Glu Ile Lys Arg
        115                 120                 125
```

<210> SEQ ID NO 159
<211> LENGTH: 125
<212> TYPE: PRT
<213> ORGANISM: Artificial Sequence
<220> FEATURE:
<223> OTHER INFORMATION: synthetic sequence

<400> SEQUENCE: 159

```
Met Arg Ala Trp Ile Phe Phe Leu Leu Cys Leu Ala Gly Arg Ala Leu
```

```
                1               5                   10                  15
Ala Asp Ile Gln Leu Thr Gln Ser Pro Ser Phe Leu Ser Ala Ser Val
                20                  25                  30

Gly Asp Arg Val Thr Ile Thr Cys Lys Ala Ser Gln Asp Val Gly Thr
                35                  40                  45

Ala Val Ala Trp Tyr Gln Gln Lys Pro Gly Lys Ala Pro Lys Leu Leu
                50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Asn Thr Tyr Pro
                100                 105                 110

Phe Thr Phe Gly Ser Gly Thr Lys Leu Glu Ile Lys Arg
                115                 120                 125
```

<210> SEQ ID NO 160
<211> LENGTH: 125
<212> TYPE: PRT
<213> ORGANISM: Artificial Sequence
<220> FEATURE:
<223> OTHER INFORMATION: synthetic sequence

<400> SEQUENCE: 160

```
Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
                20                  25                  30

Gly Asp Arg Val Thr Ile Thr Cys Lys Ala Ser Gln Asp Val Gly Thr
                35                  40                  45

Ala Val Ala Trp Tyr Gln Gln Lys Pro Gly Lys Ala Pro Lys Leu Leu
                50                  55                  60

Ile Tyr Trp Ala Phe Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Gln Ser Tyr Pro
                100                 105                 110

Phe Thr Phe Gly Ser Gly Thr Lys Leu Glu Ile Lys Arg
                115                 120                 125
```

<210> SEQ ID NO 161
<211> LENGTH: 125
<212> TYPE: PRT
<213> ORGANISM: Artificial Sequence
<220> FEATURE:
<223> OTHER INFORMATION: synthetic sequence

<400> SEQUENCE: 161

```
Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
                20                  25                  30

Gly Asp Arg Val Thr Ile Thr Cys Lys Ala Ser Gln Asp Val Gly Thr
                35                  40                  45

Ala Val Ala Trp Tyr Gln Gln Lys Pro Gly Lys Ala Pro Lys Leu Leu
                50                  55                  60
```

```
Ile Tyr Trp Ala Ala Thr Arg His Thr Gly Val Pro Ser Arg Phe Ser
 65                  70                  75                  80

Gly Ser Gly Ser Gly Thr Glu Phe Thr Leu Thr Ile Ser Ser Leu Gln
                 85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
        115                 120                 125

<210> SEQ ID NO 162
<211> LENGTH: 125
<212> TYPE: PRT
<213> ORGANISM: Artificial Sequence
<220> FEATURE:
<223> OTHER INFORMATION: synthetic sequence

<400> SEQUENCE: 162

Met Arg Ala Trp Ile Phe Phe Leu Leu Cys Leu Ala Gly Arg Ala Leu
  1               5                  10                  15

Ala Asp Ile Gln Leu Thr Gln Ser Pro Ser Phe Leu Ser Ala Ser Val
             20                  25                  30

Gly Asp Arg Val Thr Ile Thr Cys Lys Ala Ser Gln Asp Val Gly Thr
         35                  40                  45

Ala Val Ala Trp Tyr Gln Gln Lys Pro Gly Lys Ala Pro Lys Leu Leu
     50                  55                  60

Ile Tyr Trp Ala Pro Thr Arg His Thr Gly Val Pro Ser Arg Phe Ser
 65                  70                  75                  80

Gly Ser Gly Ser Gly Thr Glu Phe Thr Leu Thr Ile Ser Ser Leu Gln
                 85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
        115                 120                 125

<210> SEQ ID NO 163
<211> LENGTH: 125
<212> TYPE: PRT
<213> ORGANISM: Artificial Sequence
<220> FEATURE:
<223> OTHER INFORMATION: synthetic sequence

<400> SEQUENCE: 163

Met Arg Ala Trp Ile Phe Phe Leu Leu Cys Leu Ala Gly Arg Ala Leu
  1               5                  10                  15

Ala Asp Ile Gln Leu Thr Gln Ser Pro Ser Phe Leu Ser Ala Ser Val
             20                  25                  30

Gly Asp Arg Val Thr Ile Thr Cys Lys Ala Ser Gln Asp Val Gly Thr
         35                  40                  45

Ala Val Ala Trp Tyr Gln Gln Lys Pro Gly Lys Ala Pro Lys Leu Leu
     50                  55                  60

Ile Tyr Trp Ala Thr Thr Arg His Thr Gly Val Pro Ser Arg Phe Ser
 65                  70                  75                  80

Gly Ser Gly Ser Gly Thr Glu Phe Thr Leu Thr Ile Ser Ser Leu Gln
                 85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
        115                 120                 125
```

<210> SEQ ID NO 164
<211> LENGTH: 125
<212> TYPE: PRT
<213> ORGANISM: Artificial Sequence
<220> FEATURE:
<223> OTHER INFORMATION: synthetic sequence

<400> SEQUENCE: 164

```
Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala His Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
        115                 120                 125
```

<210> SEQ ID NO 165
<211> LENGTH: 125
<212> TYPE: PRT
<213> ORGANISM: Artificial Sequence
<220> FEATURE:
<223> OTHER INFORMATION: synthetic sequence

<400> SEQUENCE: 165

```
Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Asn Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
        115                 120                 125
```

<210> SEQ ID NO 166
<211> LENGTH: 125
<212> TYPE: PRT
<213> ORGANISM: Artificial Sequence
<220> FEATURE:
<223> OTHER INFORMATION: synthetic sequence

<400> SEQUENCE: 166

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
50                  55                  60

Ile Tyr Trp Ala Tyr Arg His Thr Gly Val Pro Ser Arg Phe Ser
65                  70                  75                  80

Gly Ser Gly Ser Gly Thr Glu Phe Thr Leu Thr Ile Ser Ser Leu Gln
            85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
            115                 120                 125

<210> SEQ ID NO 167
<211> LENGTH: 125
<212> TYPE: PRT
<213> ORGANISM: Artificial Sequence
<220> FEATURE:
<223> OTHER INFORMATION: synthetic sequence

<400> SEQUENCE: 167

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Arg Thr
        35                  40                  45

Ala Val Ala Trp Tyr Gln Gln Lys Pro Gly Lys Ala Pro Lys Leu Leu
50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
            85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
            115                 120                 125

<210> SEQ ID NO 168
<211> LENGTH: 125
<212> TYPE: PRT
<213> ORGANISM: Artificial Sequence
<220> FEATURE:
<223> OTHER INFORMATION: synthetic sequence

<400> SEQUENCE: 168

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
50                  55                  60

```
Ile Tyr Val Ala Ser Thr Arg His Thr Gly Val Pro Ser Arg Phe Ser
 65                  70                  75                  80

Gly Ser Gly Ser Gly Thr Glu Phe Thr Leu Thr Ile Ser Ser Leu Gln
                 85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
        115                 120                 125

<210> SEQ ID NO 169
<211> LENGTH: 125
<212> TYPE: PRT
<213> ORGANISM: Artificial Sequence
<220> FEATURE:
<223> OTHER INFORMATION: synthetic sequence

<400> SEQUENCE: 169

Met Arg Ala Trp Ile Phe Phe Leu Leu Cys Leu Ala Gly Arg Ala Leu
 1               5                  10                  15

Ala Asp Ile Gln Leu Thr Gln Ser Pro Ser Phe Leu Ser Ala Ser Val
            20                  25                  30

Gly Asp Arg Val Thr Ile Thr Cys Arg Ala Ser Gln Gly Ile Arg Ser
         35                  40                  45

Tyr Leu Ala Trp Tyr Gln Gln Lys Pro Gly Lys Ala Pro Lys Leu Leu
     50                  55                  60

Ile Tyr Val Ala Ser Thr Leu Gln Ser Gly Val Pro Ser Arg Phe Ser
 65                  70                  75                  80

Gly Ser Gly Ser Gly Thr Glu Phe Thr Leu Thr Ile Ser Ser Leu Gln
                 85                  90                  95

Pro Glu Asp Phe Ala Thr Tyr Tyr Cys Gln Gln Cys Asn Ser Tyr Pro
            100                 105                 110

Phe Thr Phe Gly Ser Gly Thr Lys Leu Glu Ile Lys Arg
        115                 120                 125

<210> SEQ ID NO 170
<211> LENGTH: 125
<212> TYPE: PRT
<213> ORGANISM: Artificial Sequence
<220> FEATURE:
<223> OTHER INFORMATION: synthetic sequence

<400> SEQUENCE: 170

Met Arg Ala Trp Ile Phe Phe Leu Leu Cys Leu Ala Gly Arg Ala Leu
 1               5                  10                  15

Ala Asp Ile Gln Leu Thr Gln Ser Pro Ser Phe Leu Ser Ala Ser Val
            20                  25                  30

Gly Asp Arg Val Thr Ile Thr Cys Arg Ala Ser Gln Gly Ile Arg Ser
         35                  40                  45

Tyr Leu Ala Trp Tyr Gln Gln Lys Pro Gly Lys Ala Pro Lys Leu Leu
     50                  55                  60

Ile Tyr Val Ala Ser Thr Leu Gln Ser Gly Val Pro Ser Arg Phe Ser
 65                  70                  75                  80

Gly Ser Gly Ser Gly Thr Glu Phe Thr Leu Thr Ile Ser Ser Leu Gln
                 85                  90                  95

Pro Glu Asp Phe Ala Thr Tyr Tyr Cys Gln Gln Cys Asn Asn Tyr Pro
            100                 105                 110

Phe Thr Phe Gly Ser Gly Thr Lys Leu Glu Ile Lys Arg
```

-continued

```
              115                 120                 125
```

<210> SEQ ID NO 171
<211> LENGTH: 125
<212> TYPE: PRT
<213> ORGANISM: Artificial Sequence
<220> FEATURE:
<223> OTHER INFORMATION: synthetic sequence

<400> SEQUENCE: 171

```
Met Arg Ala Trp Ile Phe Phe Leu Leu Cys Leu Ala Gly Arg Ala Leu
1               5                  10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Lys Thr Tyr Pro
            100                 105                 110

Phe Thr Phe Gly Ser Gly Thr Lys Leu Glu Ile Lys Arg
        115                 120                 125
```

<210> SEQ ID NO 172
<211> LENGTH: 125
<212> TYPE: PRT
<213> ORGANISM: Artificial Sequence
<220> FEATURE:
<223> OTHER INFORMATION: synthetic sequence

<400> SEQUENCE: 172

```
Met Arg Ala Trp Ile Phe Phe Leu Leu Cys Leu Ala Gly Arg Ala Leu
1               5                  10                  15

Ala Asp Ile Gln Leu Thr Gln Ser Pro Ser Phe Leu Ser Ala Ser Val
            20                  25                  30

Gly Asp Arg Val Thr Ile Thr Cys Arg Ala Ser Gln Gly Ile Arg Ser
        35                  40                  45

Tyr Leu Ala Trp Tyr Gln Gln Lys Pro Gly Lys Ala Pro Lys Leu Leu
    50                  55                  60

Ile Tyr Val Ala Ser Thr Leu Gln Ser Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Asn Asn Tyr Pro
            100                 105                 110

Phe Thr Phe Gly Ser Gly Thr Lys Leu Glu Ile Lys Arg
        115                 120                 125
```

<210> SEQ ID NO 173
<211> LENGTH: 125
<212> TYPE: PRT
<213> ORGANISM: Artificial Sequence
<220> FEATURE:
<223> OTHER INFORMATION: synthetic sequence

<400> SEQUENCE: 173

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Arg Ala Ser Gln Gly Ile Arg Ser
        35                  40                  45

Tyr Leu Ala Trp Tyr Gln Gln Lys Pro Gly Lys Ala Pro Lys Leu Leu
    50                  55                  60

Ile Tyr Val Ala Ser Thr Leu Gln Ser Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Gln Ser Tyr Pro
            100                 105                 110

Phe Thr Phe Gly Ser Gly Thr Lys Leu Glu Ile Lys Arg
        115                 120                 125

<210> SEQ ID NO 174
<211> LENGTH: 125
<212> TYPE: PRT
<213> ORGANISM: Artificial Sequence
<220> FEATURE:
<223> OTHER INFORMATION: synthetic sequence

<400> SEQUENCE: 174

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Arg Ala Ser Gln Gly Ile Arg Ser
        35                  40                  45

Tyr Leu Ala Trp Tyr Gln Gln Lys Pro Gly Lys Ala Pro Lys Leu Leu
    50                  55                  60

Ile Tyr Val Ala Phe Thr Leu Gln Ser Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Cys Asn Ser Tyr Pro
            100                 105                 110

Phe Thr Phe Gly Ser Gly Thr Lys Leu Glu Ile Lys Arg
        115                 120                 125

<210> SEQ ID NO 175
<211> LENGTH: 125
<212> TYPE: PRT
<213> ORGANISM: Artificial Sequence
<220> FEATURE:
<223> OTHER INFORMATION: synthetic sequence

<400> SEQUENCE: 175

Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Arg Ala Ser Gln Gly Ile Arg Ser
        35                  40                  45

Tyr Leu Ala Trp Tyr Gln Gln Lys Pro Gly Lys Ala Pro Lys Leu Leu

```
                    50                  55                  60
Ile Tyr Val Ala Phe Thr Leu Gln Ser Gly Val Pro Ser Arg Phe Ser
 65                  70                  75                  80

Gly Ser Gly Ser Gly Thr Glu Phe Thr Leu Thr Ile Ser Ser Leu Gln
                     85                  90                  95

Pro Glu Asp Phe Ala Thr Tyr Tyr Cys Gln Gln Cys Asn Asn Tyr Pro
                100                 105                 110

Phe Thr Phe Gly Ser Gly Thr Lys Leu Glu Ile Lys Arg
            115                 120                 125

<210> SEQ ID NO 176
<211> LENGTH: 139
<212> TYPE: PRT
<213> ORGANISM: Artificial Sequence
<220> FEATURE:
<223> OTHER INFORMATION: synthetic sequence

<400> SEQUENCE: 176

Met Arg Ala Trp Ile Phe Phe Leu Leu Cys Leu Ala Gly Arg Ala Leu
  1               5                  10                  15

Ala Gln Val Gln Leu Val Gln Ser Gly Ala Glu Val Lys Lys Pro Gly
                 20                  25                  30

Ala Ser Val Lys Val Ser Cys Lys Ala Ser Gly Tyr Thr Phe Thr Ser
             35                  40                  45

Tyr Tyr Met His Trp Val Arg Gln Ala Pro Gly Gln Gly Leu Glu Trp
         50                  55                  60

Met Gly Thr Ile Tyr Pro Arg Asn Ser Asp Thr Asp Tyr Asn Gln Lys
 65                  70                  75                  80

Phe Lys Ala Arg Val Thr Met Thr Arg Asp Thr Ser Thr Ser Thr Val
                 85                  90                  95

Tyr Met Glu Leu Ser Ser Leu Arg Ser Glu Asp Thr Ala Val Tyr Tyr
                100                 105                 110

Cys Ala Arg Pro Leu Tyr Tyr Val Thr Ser Pro Pro Thr Leu Leu
             115                 120                 125

Trp Gly Gln Gly Thr Leu Val Thr Val Ser Ser
    130                 135

<210> SEQ ID NO 177
<211> LENGTH: 139
<212> TYPE: PRT
<213> ORGANISM: Artificial Sequence
<220> FEATURE:
<223> OTHER INFORMATION: synthetic sequence

<400> SEQUENCE: 177

Met Arg Ala Trp Ile Phe Phe Leu Leu Cys Leu Ala Gly Arg Ala Leu
  1               5                  10                  15

Ala Gln Val Gln Leu Val Gln Ser Gly Ala Glu Val Lys Lys Pro Gly
                 20                  25                  30

Ala Ser Val Lys Val Ser Cys Lys Ala Ser Gly Tyr Thr Phe Thr Ser
             35                  40                  45

Tyr Trp Met His Trp Val Arg Gln Ala Pro Gly Gln Gly Leu Glu Trp
         50                  55                  60

Met Gly Ile Ile Asn Pro Ser Gly Gly Ser Thr Ser Tyr Ala Gln Lys
 65                  70                  75                  80

Phe Gln Gly Arg Val Thr Met Thr Arg Asp Thr Ser Thr Ser Thr Val
                 85                  90                  95
```

```
Tyr Met Glu Leu Ser Ser Leu Arg Ser Glu Asp Thr Ala Val Tyr Tyr
            100                 105                 110

Cys Ala Arg Pro Leu Tyr Tyr Val Thr Pro Pro Thr Leu Leu
            115                 120                 125

Trp Gly Gln Gly Thr Leu Val Thr Val Ser Ser
        130                 135
```

<210> SEQ ID NO 178
<211> LENGTH: 144
<212> TYPE: PRT
<213> ORGANISM: Artificial Sequence
<220> FEATURE:
<223> OTHER INFORMATION: synthetic sequence

<400> SEQUENCE: 178

```
Met Arg Ala Trp Ile Phe Phe Leu Leu Cys Leu Ala Gly Arg Ala Leu
1               5                   10                  15

Ala Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Ser Asn
        35                  40                  45

Tyr Trp Met Asn Trp Val Arg Gln Ala Pro Gly Lys Gly Leu Glu Trp
    50                  55                  60

Val Ala Asp Ile Arg Leu Lys Ser Asn Asn Tyr Ala Thr His Tyr Ala
65                  70                  75                  80

Glu Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Arg Asp Gly Pro Tyr Trp Gly Gln Gly Thr Leu Val
        115                 120                 125

Thr Val Ser Ala Ala Ser Thr Lys Gly Pro Ser Val Phe Pro Leu Ala
    130                 135                 140
```

<210> SEQ ID NO 179
<211> LENGTH: 144
<212> TYPE: PRT
<213> ORGANISM: Artificial Sequence
<220> FEATURE:
<223> OTHER INFORMATION: synthetic sequence

<400> SEQUENCE: 179

```
Met Arg Ala Trp Ile Phe Phe Leu Leu Cys Leu Ala Gly Arg Ala Leu
1               5                   10                  15

Ala Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Ser Asn
        35                  40                  45

Tyr Trp Met Asn Trp Val Arg Gln Ala Pro Gly Lys Gly Leu Glu Trp
    50                  55                  60

Val Ala Asp Ile Arg Leu Lys Ser Asn Asn Tyr Ala Thr His Tyr Ala
65                  70                  75                  80

Glu Ser Val Lys Gly Arg Phe Thr Ile Ser Arg Asp Asp Ala Lys Ser
                85                  90                  95

Ser Leu Tyr Leu Gln Met Asn Asn Leu Arg Ala Glu Asp Thr Ala Val
            100                 105                 110

Tyr Tyr Cys Val Arg Asp Gly Pro Tyr Trp Gly Gln Gly Thr Leu Val
        115                 120                 125
```

```
Thr Val Ser Ala Ala Ser Thr Lys Gly Pro Ser Val Phe Pro Leu Ala
        130                 135                 140

<210> SEQ ID NO 180
<211> LENGTH: 144
<212> TYPE: PRT
<213> ORGANISM: Artificial Sequence
<220> FEATURE:
<223> OTHER INFORMATION: synthetic sequence

<400> SEQUENCE: 180

Met Arg Ala Trp Ile Phe Phe Leu Leu Cys Leu Ala Gly Arg Ala Leu
1               5                   10                  15

Ala Glu Val Gln Leu Val Glu Ser Gly Gly Leu Val Gln Pro Gly
            20                  25                  30

Gly Ser Leu Arg Leu Ser Cys Val Ala Ser Gly Phe Thr Phe Ser Asn
        35                  40                  45

Tyr Trp Met Asn Trp Val Arg Gln Ala Pro Gly Lys Gly Leu Glu Trp
    50                  55                  60

Val Ala Asp Ile Arg Leu Lys Ser Asn Asn Tyr Ala Thr His Tyr Ala
65                  70                  75                  80

Glu Ser Val Lys Gly Arg Phe Thr Ile Ser Arg Asp Asp Ala Lys Asn
                85                  90                  95

Ser Val Tyr Leu Gln Met Asn Ser Leu Arg Ala Glu Asp Thr Ala Val
            100                 105                 110

Tyr Tyr Cys Val Arg Asp Gly Pro Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

<210> SEQ ID NO 181
<211> LENGTH: 144
<212> TYPE: PRT
<213> ORGANISM: Artificial Sequence
<220> FEATURE:
<223> OTHER INFORMATION: synthetic sequence

<400> SEQUENCE: 181

Met Arg Ala Trp Ile Phe Phe Leu Leu Cys Leu Ala Gly Arg Ala Leu
1               5                   10                  15

Ala Glu Val Gln Leu Val Glu Ser Gly Gly Leu Val Gln Pro Gly
            20                  25                  30

Gly Ser Leu Arg Leu Ser Cys Val Ala Ser Gly Phe Thr Phe Ser Asn
        35                  40                  45

Tyr Trp Met Asn Trp Val Arg Gln Ala Pro Gly Lys Gly Leu Glu Trp
    50                  55                  60

Val Ala Asp Ile Arg Leu Lys Ser Asn Asn Tyr Ala Thr His Tyr Ala
65                  70                  75                  80

Glu Ser Val Lys Gly Arg Phe Thr Ile Ser Arg Asp Asp Ala Lys Ser
                85                  90                  95

Ser Val Tyr Leu Gln Met Asn Ser Leu Arg Ala Glu Asp Thr Ala Val
            100                 105                 110

Tyr Tyr Cys Val Arg Asp Gly Pro Tyr Trp Gly Gln Gly Thr Leu Val
        115                 120                 125

Thr Val Ser Ala Ala Ser Thr Lys Gly Pro Ser Val Phe Pro Leu Ala
    130                 135                 140
```

<210> SEQ ID NO 182
<211> LENGTH: 144
<212> TYPE: PRT
<213> ORGANISM: Artificial Sequence
<220> FEATURE:
<223> OTHER INFORMATION: synthetic sequence

<400> SEQUENCE: 182

```
Met Arg Ala Trp Ile Phe Phe Leu Leu Cys Leu Ala Gly Arg Ala Leu
1               5                   10                  15

Ala Glu Val Gln Leu Val Glu Ser Gly Gly Leu Val Gln Pro Gly
            20                  25                  30

Gly Ser Leu Arg Leu Ser Cys Val Ala Ser Gly Phe Thr Phe Ser Asn
        35                  40                  45

Tyr Trp Met Asn Trp Val Arg Gln Ala Pro Gly Lys Gly Leu Glu Trp
    50                  55                  60

Val Ala Asp Ile Arg Leu Lys Ser Asn Asn Tyr Ala Thr His Tyr Ala
65                  70                  75                  80

Glu Ser Val Lys Gly Arg Phe Thr Ile Ser Arg Asp Asp Ala Lys Asn
                85                  90                  95

Ser Val Tyr Leu Gln Met Asn Ser Leu Arg Ala Glu Asp Thr Ala Val
            100                 105                 110

Tyr Tyr Cys Val Arg Asp Ala Pro Tyr Trp Gly Gln Gly Thr Leu Val
        115                 120                 125

Thr Val Ser Ala Ala Ser Thr Lys Gly Pro Ser Val Phe Pro Leu Ala
    130                 135                 140
```

<210> SEQ ID NO 183
<211> LENGTH: 144
<212> TYPE: PRT
<213> ORGANISM: Artificial Sequence
<220> FEATURE:
<223> OTHER INFORMATION: synthetic sequence

<400> SEQUENCE: 183

```
Met Arg Ala Trp Ile Phe Phe Leu Leu Cys Leu Ala Gly Arg Ala Leu
1               5                   10                  15

Ala Glu Val Gln Leu Val Glu Ser Gly Gly Leu Val Gln Pro Gly
            20                  25                  30

Gly Ser Leu Arg Leu Ser Cys Val Ala Ser Gly Phe Thr Phe Ser Asn
        35                  40                  45

Tyr Trp Met Asn Trp Val Arg Gln Ala Pro Gly Lys Gly Leu Glu Trp
    50                  55                  60

Val Ala Asp Ile Arg Leu Lys Ser Asn Asn Tyr Ala Thr His Tyr Ala
65                  70                  75                  80

Glu Ser Val Lys Gly Arg Phe Thr Ile Ser Arg Asp Asp Ala Lys Asn
                85                  90                  95

Ser Val Tyr Leu Gln Met Asn Ser Leu Arg Ala Glu Asp Thr Ala Val
            100                 105                 110

Tyr Tyr Cys Val Arg Asp Ser Pro Tyr Trp Gly Gln Gly Thr Leu Val
        115                 120                 125

Thr Val Ser Ala Ala Ser Thr Lys Gly Pro Ser Val Phe Pro Leu Ala
    130                 135                 140
```

<210> SEQ ID NO 184
<211> LENGTH: 144
<212> TYPE: PRT
<213> ORGANISM: Artificial Sequence
<220> FEATURE:

<223> OTHER INFORMATION: synthetic sequence

<400> SEQUENCE: 184

Met Arg Ala Trp Ile Phe Phe Leu Leu Cys Leu Ala Gly Arg Ala Leu
1               5                   10                  15
Ala Glu Val Gln Leu Val Glu Ser Gly Gly Gly Leu Val Gln Pro Gly
            20                  25                  30
Gly Ser Leu Arg Leu Ser Cys Val Ala Ser Gly Phe Thr Phe Ser Asn
        35                  40                  45
Tyr Trp Met Asn Trp Val Arg Gln Ala Pro Gly Lys Gly Leu Glu Trp
    50                  55                  60
Val Ala Asp Ile Arg Leu Lys Ser Asn Asn Tyr Ala Thr His Tyr Ala
65                  70                  75                  80
Glu Ser Val Lys Gly Arg Phe Thr Ile Ser Arg Asp Asp Ala Lys Asn
                85                  90                  95
Ser Val Tyr Leu Gln Met Asn Ser Leu Arg Ala Glu Asp Thr Ala Val
            100                 105                 110
Tyr Tyr Cys Val Arg Gly Gly Pro Tyr Trp Gly Gln Gly Thr Leu Val
        115                 120                 125
Thr Val Ser Ala Ala Ser Thr Lys Gly Pro Ser Val Phe Pro Leu Ala
    130                 135                 140

<210> SEQ ID NO 185
<211> LENGTH: 144
<212> TYPE: PRT
<213> ORGANISM: Artificial Sequence
<220> FEATURE:
<223> OTHER INFORMATION: synthetic sequence

<400> SEQUENCE: 185

Met Arg Ala Trp Ile Phe Phe Leu Leu Cys Leu Ala Gly Arg Ala Leu
1               5                   10                  15
Ala Glu Val Gln Leu Val Glu Ser Gly Gly Gly Leu Val Gln Pro Gly
            20                  25                  30
Gly Ser Leu Arg Leu Ser Cys Val Ala Ser Gly Phe Thr Phe Ser Asn
        35                  40                  45
Tyr Trp Met Asn Trp Val Arg Gln Ala Pro Gly Lys Gly Leu Glu Trp
    50                  55                  60
Val Ala Asp Ile Arg Leu Lys Ser Asn Asn Tyr Ala Thr His Tyr Ala
65                  70                  75                  80
Glu Ser Val Lys Gly Arg Phe Thr Ile Ser Arg Asp Asp Ala Lys Asn
                85                  90                  95
Ser Val Tyr Leu Gln Met Asn Ser Leu Arg Ala Glu Asp Thr Ala Val
            100                 105                 110
Tyr Tyr Cys Val Arg Ser Gly Pro Tyr Trp Gly Gln Gly Thr Leu Val
        115                 120                 125
Thr Val Ser Ala Ala Ser Thr Lys Gly Pro Ser Val Phe Pro Leu Ala
    130                 135                 140

<210> SEQ ID NO 186
<211> LENGTH: 144
<212> TYPE: PRT
<213> ORGANISM: Artificial Sequence
<220> FEATURE:
<223> OTHER INFORMATION: synthetic sequence

<400> SEQUENCE: 186

Met Arg Ala Trp Ile Phe Phe Leu Leu Cys Leu Ala Gly Arg Ala Leu

```
            1               5                   10                  15
        Ala Glu Val Gln Leu Val Glu Ser Gly Gly Gly Leu Val Gln Pro Gly
                        20                  25                  30

Gly Ser Leu Arg Leu Ser Cys Val Ala Ser Gly Phe Thr Phe Ser Asn
                        35                  40                  45

Tyr Trp Met Asn Trp Val Arg Gln Ala Pro Gly Lys Gly Leu Glu Trp
                        50                  55                  60

Val Ala Asp Ile Arg Leu Lys Ser Asn Asn Tyr Ala Thr His Tyr Ala
         65                     70                  75                  80

Glu Ser Val Lys Gly Arg Phe Thr Ile Ser Arg Asp Asp Ala Lys Asn
                        85                  90                  95

Ser Val Tyr Leu Gln Met Asn Ser Leu Arg Ala Glu Asp Thr Ala Val
                        100                 105                 110

Tyr Tyr Cys Val Arg Thr Gly Pro Tyr Trp Gly Gln Gly Thr Leu Val
                        115                 120                 125

Thr Val Ser Ala Ala Ser Thr Lys Gly Pro Ser Val Phe Pro Leu Ala
                        130                 135                 140

<210> SEQ ID NO 187
<211> LENGTH: 144
<212> TYPE: PRT
<213> ORGANISM: Artificial Sequence
<220> FEATURE:
<223> OTHER INFORMATION: synthetic sequence

<400> SEQUENCE: 187

Met Arg Ala Trp Ile Phe Phe Leu Leu Cys Leu Ala Gly Arg Ala Leu
        1               5                   10                  15

Ala Glu Val Gln Leu Val Glu Ser Gly Gly Gly Leu Val Gln Pro Gly
                        20                  25                  30

Gly Ser Leu Arg Leu Ser Cys Val Ala Ser Gly Phe Thr Phe Ser Asn
                        35                  40                  45

Tyr Trp Met Asn Trp Val Arg Gln Ala Pro Gly Lys Gly Leu Glu Trp
                        50                  55                  60

Val Ala Asp Ile Arg Leu Lys Ser Asn Asn Tyr Ala Thr His Tyr Ala
         65                     70                  75                  80

Glu Ser Val Lys Gly Arg Phe Thr Ile Ser Arg Asp Asp Ala Lys Asn
                        85                  90                  95

Ser Val Tyr Leu Gln Met Asn Ser Leu Arg Ala Glu Asp Thr Ala Val
                        100                 105                 110

Tyr Tyr Cys Val Arg Met Gly Pro Tyr Trp Gly Gln Gly Thr Leu Val
                        115                 120                 125

Thr Val Ser Ala Ala Ser Thr Lys Gly Pro Ser Val Phe Pro Leu Ala
                        130                 135                 140

<210> SEQ ID NO 188
<211> LENGTH: 125
<212> TYPE: PRT
<213> ORGANISM: Artificial Sequence
<220> FEATURE:
<223> OTHER INFORMATION: synthetic sequence

<400> SEQUENCE: 188

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Thr Phe Ser Ser Tyr
                        20                  25                  30
```

```
Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Val Arg Asp Gly Pro Tyr Trp Gly Gln Gly Thr Leu Val Thr Val Ser
            100                 105                 110

Ala Ala Ser Thr Lys Gly Pro Ser Val Phe Pro Leu Ala
            115                 120                 125
```

<210> SEQ ID NO 189
<211> LENGTH: 113
<212> TYPE: PRT
<213> ORGANISM: Artificial Sequence
<220> FEATURE:
<223> OTHER INFORMATION: synthetic sequence

<400> SEQUENCE: 189

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
            35                  40                  45

Pro Arg Arg Leu Ile Tyr Lys Ile Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Thr Lys Leu Glu Ile Lys
            100                 105                 110

Arg
```

<210> SEQ ID NO 190
<211> LENGTH: 130
<212> TYPE: PRT
<213> ORGANISM: Artificial Sequence
<220> FEATURE:
<223> OTHER INFORMATION: synthetic sequence

<400> SEQUENCE: 190

```
Met Arg Ala Trp Ile Phe Phe Leu Leu Cys Leu Ala Gly Arg Ala Leu
 1               5                  10                  15

Ala Asp Val Val Met Thr Gln Ser Pro Leu Ser Leu Pro Val Thr Leu
            20                  25                  30

Gly Gln Pro Ala Ser Ile Ser Cys Arg Ser Ser Gln Ser Leu Val Tyr
            35                  40                  45

Ser Asp Gly Asn Thr Tyr Leu Asn Trp Phe Gln Gln Arg Pro Gly Gln
 50                  55                  60

Ser Pro Arg Arg Leu Ile Tyr Lys Val Ser Asn Arg Asp Ser Gly Val
 65                  70                  75                  80

Pro Asp Arg Phe Ser Gly Ser Gly Ser Gly Thr Asp Phe Thr Leu Lys
                85                  90                  95
```

Ile Ser Arg Val Glu Ala Glu Asp Val Gly Val Tyr Tyr Cys Phe Gln
            100                 105                 110

Gly Ser His Val Pro Arg Thr Phe Gly Gly Gly Thr Lys Leu Glu Ile
            115                 120                 125

Lys Arg
    130

<210> SEQ ID NO 191
<211> LENGTH: 130
<212> TYPE: PRT
<213> ORGANISM: Artificial Sequence
<220> FEATURE:
<223> OTHER INFORMATION: synthetic sequence

<400> SEQUENCE: 191

Met Arg Ala Trp Ile Phe Phe Leu Leu Cys Leu Ala Gly Arg Ala Leu
1               5                   10                  15

Ala Asp Val Val Met Thr Gln Ser Pro Leu Ser Leu Pro Val Thr Leu
            20                  25                  30

Gly Gln Pro Ala Ser Ile Ser Cys Arg Ser Ser Gln Ser Ile Val His
        35                  40                  45

Ser Asn Gly Asn Thr Tyr Leu Glu Trp Tyr Leu Gln Arg Pro Gly Gln
    50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
            100                 105                 110

Gly Ser His Val Pro Arg Thr Phe Gly Gly Gly Thr Lys Leu Glu Ile
            115                 120                 125

Lys Arg
    130

<210> SEQ ID NO 192
<211> LENGTH: 130
<212> TYPE: PRT
<213> ORGANISM: Artificial Sequence
<220> FEATURE:
<223> OTHER INFORMATION: synthetic sequence

<400> SEQUENCE: 192

Met Arg Ala Trp Ile Phe Phe Leu Leu Cys Leu Ala Gly Arg Ala Leu
1               5                   10                  15

Ala Asp Val Leu Met Thr Gln Ser Pro Leu Ser Leu Pro Val Thr Leu
            20                  25                  30

Gly Gln Pro Ala Ser Ile Ser Cys Arg Ser Ser Gln Ser Ile Val His
        35                  40                  45

Ser Asn Gly Asn Thr Tyr Leu Glu Trp Tyr Gln Gln Arg Pro Gly Gln
    50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
            100                 105                 110

Gly Ser His Val Pro Arg Thr Phe Gly Gly Gly Thr Lys Leu Glu Ile
            115                 120                 125

Lys Arg
    130

<210> SEQ ID NO 193
<211> LENGTH: 130
<212> TYPE: PRT
<213> ORGANISM: Artificial Sequence
<220> FEATURE:
<223> OTHER INFORMATION: synthetic sequence

<400> SEQUENCE: 193

Met Arg Ala Trp Ile Phe Phe Leu Leu Cys Leu Ala Gly Arg Ala Leu
1               5                   10                  15

Ala Asp Val Val Met Thr Gln Ser Pro Leu Ser Leu Pro Val Thr Leu
            20                  25                  30

Gly Gln Pro Ala Ser Ile Ser Cys Arg Ser Ser Gln Ser Ile Val His
        35                  40                  45

Ser Asn Gly Asn Thr Tyr Leu Glu Trp Tyr Gln Gln Arg Pro Gly Gln
    50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
            100                 105                 110

Gly Ser His Val Pro Arg Thr Phe Gly Gly Gly Thr Lys Leu Glu Ile
        115                 120                 125

Lys Arg
    130

<210> SEQ ID NO 194
<211> LENGTH: 130
<212> TYPE: PRT
<213> ORGANISM: Artificial Sequence
<220> FEATURE:
<223> OTHER INFORMATION: synthetic sequence

<400> SEQUENCE: 194

Met Arg Ala Trp Ile Phe Phe Leu Leu Cys Leu Ala Gly Arg Ala Leu
1               5                   10                  15

Ala Asp Val Val Met Thr Gln Ser Pro Leu Ser Leu Pro Val Thr Leu
            20                  25                  30

Gly Gln Pro Ala Ser Ile Ser Cys Arg Ser Ser Gln Ser Ile Val His
        35                  40                  45

Ser Gln Gly Asn Thr Tyr Leu Glu Trp Tyr Gln Gln Arg Pro Gly Gln
    50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
            100                 105                 110

Gly Ser His Val Pro Arg Thr Phe Gly Gly Gly Thr Lys Leu Glu Ile
        115                 120                 125

Lys Arg
    130

```
-continued

<210> SEQ ID NO 195
<211> LENGTH: 130
<212> TYPE: PRT
<213> ORGANISM: Artificial Sequence
<220> FEATURE:
<223> OTHER INFORMATION: synthetic sequence

<400> SEQUENCE: 195

Met Arg Ala Trp Ile Phe Phe Leu Leu Cys Leu Ala Gly Arg Ala Leu
1               5                   10                  15

Ala Asp Val Val Met Thr Gln Ser Pro Leu Ser Leu Pro Val Thr Leu
            20                  25                  30

Gly Gln Pro Ala Ser Ile Ser Cys Arg Ser Ser Gln Ser Ile Val His
        35                  40                  45

Ser Leu Gly Asn Thr Tyr Leu Glu Trp Tyr Gln Gln Arg Pro Gly Gln
    50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
            100                 105                 110

Gly Ser His Val Pro Arg Thr Phe Gly Gly Gly Thr Lys Leu Glu Ile
        115                 120                 125

Lys Arg
    130

<210> SEQ ID NO 196
<211> LENGTH: 130
<212> TYPE: PRT
<213> ORGANISM: Artificial Sequence
<220> FEATURE:
<223> OTHER INFORMATION: synthetic sequence

<400> SEQUENCE: 196

Met Arg Ala Trp Ile Phe Phe Leu Leu Cys Leu Ala Gly Arg Ala Leu
1               5                   10                  15

Ala Asp Val Val Met Thr Gln Ser Pro Leu Ser Leu Pro Val Thr Leu
            20                  25                  30

Gly Gln Pro Ala Ser Ile Ser Cys Arg Ser Ser Gln Ser Ile Val His
        35                  40                  45

Ser Ala Gly Asn Thr Tyr Leu Glu Trp Tyr Gln Gln Arg Pro Gly Gln
    50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
            100                 105                 110

Gly Ser His Val Pro Arg Thr Phe Gly Gly Gly Thr Lys Leu Glu Ile
        115                 120                 125

Lys Arg
    130

<210> SEQ ID NO 197
<211> LENGTH: 130
<212> TYPE: PRT
<213> ORGANISM: Artificial Sequence
<220> FEATURE:
```

<223> OTHER INFORMATION: synthetic sequence

<400> SEQUENCE: 197

Met Arg Ala Trp Ile Phe Phe Leu Leu Cys Leu Ala Gly Arg Ala Leu
1               5                   10                  15

Ala Asp Val Val Met Thr Gln Ser Pro Leu Ser Leu Pro Val Thr Leu
            20                  25                  30

Gly Gln Pro Ala Ser Ile Ser Cys Arg Ser Ser Gln Ser Ile Val His
        35                  40                  45

Ser Ser Gly Asn Thr Tyr Leu Glu Trp Tyr Gln Gln Arg Pro Gly Gln
50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
            85                  90                  95

Ile Ser Arg Val Glu Ala Glu Asp Val Gly Val Tyr Tyr Cys Phe Gln
        100                 105                 110

Gly Ser His Val Pro Arg Thr Phe Gly Gly Gly Thr Lys Leu Glu Ile
    115                 120                 125

Lys Arg
    130

<210> SEQ ID NO 198
<211> LENGTH: 130
<212> TYPE: PRT
<213> ORGANISM: Artificial Sequence
<220> FEATURE:
<223> OTHER INFORMATION: synthetic sequence

<400> SEQUENCE: 198

Met Arg Ala Trp Ile Phe Phe Leu Leu Cys Leu Ala Gly Arg Ala Leu
1               5                   10                  15

Ala Asp Val Val Met Thr Gln Ser Pro Leu Ser Leu Pro Val Thr Leu
            20                  25                  30

Gly Gln Pro Ala Ser Ile Ser Cys Arg Ser Ser Gln Ser Ile Val His
        35                  40                  45

Ser Glu Gly Asn Thr Tyr Leu Glu Trp Tyr Gln Gln Arg Pro Gly Gln
50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
            85                  90                  95

Ile Ser Arg Val Glu Ala Glu Asp Val Gly Val Tyr Tyr Cys Phe Gln
        100                 105                 110

Gly Ser His Val Pro Arg Thr Phe Gly Gly Gly Thr Lys Leu Glu Ile
    115                 120                 125

Lys Arg
    130

<210> SEQ ID NO 199
<211> LENGTH: 130
<212> TYPE: PRT
<213> ORGANISM: Artificial Sequence
<220> FEATURE:
<223> OTHER INFORMATION: synthetic sequence

<400> SEQUENCE: 199

Met Arg Ala Trp Ile Phe Phe Leu Leu Cys Leu Ala Gly Arg Ala Leu

```
            1               5                  10                 15
Ala Asp Val Val Met Thr Gln Ser Pro Leu Ser Leu Pro Val Thr Leu
                20                  25                 30

Gly Gln Pro Ala Ser Ile Ser Cys Arg Ser Ser Gln Ser Ile Val His
                35                  40                 45

Ser Thr Gly Asn Thr Tyr Leu Glu Trp Tyr Gln Gln Arg Pro Gly Gln
        50                  55                 60

Ser Pro Arg Leu Leu Ile Tyr Lys Ile Ser Asn Arg Phe Ser Gly Val
 65                  70                  75                  80

Pro Asp Arg Phe Ser Gly Ser Gly Ser Gly Thr Asp Phe Thr Leu Lys
                85                  90                 95

Ile Ser Arg Val Glu Ala Glu Asp Val Gly Val Tyr Tyr Cys Phe Gln
                100                 105                110

Gly Ser His Val Pro Arg Thr Phe Gly Gly Gly Thr Lys Leu Glu Ile
                115                 120                125

Lys Arg
    130

<210> SEQ ID NO 200
<211> LENGTH: 130
<212> TYPE: PRT
<213> ORGANISM: Artificial Sequence
<220> FEATURE:
<223> OTHER INFORMATION: synthetic sequence

<400> SEQUENCE: 200

Met Arg Ala Trp Ile Phe Phe Leu Leu Cys Leu Ala Gly Arg Ala Leu
 1               5                  10                 15

Ala Asp Val Val Met Thr Gln Ser Pro Leu Ser Leu Pro Val Thr Leu
                20                  25                 30

Gly Gln Pro Ala Ser Ile Ser Cys Arg Ser Ser Gln Ser Ile Val His
                35                  40                 45

Ser Asn Ala Asn Thr Tyr Leu Glu Trp Tyr Gln Gln Arg Pro Gly Gln
        50                  55                 60

Ser Pro Arg Leu Leu Ile Tyr Lys Ile Ser Asn Arg Phe Ser Gly Val
 65                  70                  75                  80

Pro Asp Arg Phe Ser Gly Ser Gly Ser Gly Thr Asp Phe Thr Leu Lys
                85                  90                 95

Ile Ser Arg Val Glu Ala Glu Asp Val Gly Val Tyr Tyr Cys Phe Gln
                100                 105                110

Gly Ser His Val Pro Arg Thr Phe Gly Gly Gly Thr Lys Leu Glu Ile
                115                 120                125

Lys Arg
    130

<210> SEQ ID NO 201
<211> LENGTH: 130
<212> TYPE: PRT
<213> ORGANISM: Artificial Sequence
<220> FEATURE:
<223> OTHER INFORMATION: synthetic sequence

<400> SEQUENCE: 201

Met Arg Ala Trp Ile Phe Phe Leu Leu Cys Leu Ala Gly Arg Ala Leu
 1               5                  10                 15

Ala Asp Val Val Met Thr Gln Ser Pro Leu Ser Leu Pro Val Thr Leu
                20                  25                 30
```

```
Gly Gln Pro Ala Ser Ile Ser Cys Arg Ser Ser Gln Ser Ile Val His
            35                  40                  45

Ser Asn Asp Asn Thr Tyr Leu Glu Trp Tyr Gln Gln Arg Pro Gly Gln
 50                      55                  60

Ser Pro Arg Leu Leu Ile Tyr Lys Ile Ser Asn Arg Phe Ser Gly Val
 65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
                100                 105                 110

Gly Ser His Val Pro Arg Thr Phe Gly Gly Gly Thr Lys Leu Glu Ile
            115                 120                 125

Lys Arg
    130

<210> SEQ ID NO 202
<211> LENGTH: 130
<212> TYPE: PRT
<213> ORGANISM: Artificial Sequence
<220> FEATURE:
<223> OTHER INFORMATION: synthetic sequence

<400> SEQUENCE: 202

Met Arg Ala Trp Ile Phe Phe Leu Leu Cys Leu Ala Gly Arg Ala Leu
 1               5                  10                  15

Ala Asp Val Val Met Thr Gln Ser Pro Leu Ser Leu Pro Val Thr Leu
                20                  25                  30

Gly Gln Pro Ala Ser Ile Ser Cys Arg Ser Ser Gln Ser Ile Val His
            35                  40                  45

Ser Phe Gly Asn Thr Tyr Leu Glu Trp Tyr Gln Gln Arg Pro Gly Gln
 50                      55                  60

Ser Pro Arg Leu Leu Ile Tyr Lys Ile Ser Asn Arg Phe Ser Gly Val
 65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
                100                 105                 110

Gly Ser His Val Pro Arg Thr Phe Gly Gly Gly Thr Lys Leu Glu Ile
            115                 120                 125

Lys Arg
    130

<210> SEQ ID NO 203
<211> LENGTH: 130
<212> TYPE: PRT
<213> ORGANISM: Artificial Sequence
<220> FEATURE:
<223> OTHER INFORMATION: synthetic sequence

<400> SEQUENCE: 203

Met Arg Ala Trp Ile Phe Phe Leu Leu Cys Leu Ala Gly Arg Ala Leu
 1               5                  10                  15

Ala Asp Val Val Met Thr Gln Ser Pro Leu Ser Leu Pro Val Thr Leu
                20                  25                  30

Gly Gln Pro Ala Ser Ile Ser Cys Arg Ser Ser Gln Ser Ile Val His
            35                  40                  45

Ser Asn Val Asn Thr Tyr Leu Glu Trp Tyr Gln Gln Arg Pro Gly Gln
 50                      55                  60
```

-continued

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
                100                 105                 110

Gly Ser His Val Pro Arg Thr Phe Gly Gly Gly Thr Lys Leu Glu Ile
        115                 120                 125

Lys Arg
    130

<210> SEQ ID NO 204
<211> LENGTH: 130
<212> TYPE: PRT
<213> ORGANISM: Artificial Sequence
<220> FEATURE:
<223> OTHER INFORMATION: synthetic sequence

<400> SEQUENCE: 204

Met Arg Ala Trp Ile Phe Phe Leu Leu Cys Leu Ala Gly Arg Ala Leu
1               5                   10                  15

Ala Asp Val Leu Met Thr Gln Ser Pro Leu Ser Leu Pro Val Thr Leu
                20                  25                  30

Gly Gln Pro Ala Ser Ile Ser Cys Arg Ser Ser Gln Ser Ile Val His
            35                  40                  45

Ser Asn Gly Asn Thr Tyr Leu Glu Trp Tyr Gln Gln Arg Pro Gly Gln
        50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
                100                 105                 110

Gly Ser His Val Pro Arg Thr Phe Gly Gly Gly Thr Lys Leu Glu Ile
        115                 120                 125

Lys Arg
    130

<210> SEQ ID NO 205
<211> LENGTH: 130
<212> TYPE: PRT
<213> ORGANISM: Artificial Sequence
<220> FEATURE:
<223> OTHER INFORMATION: synthetic sequence

<400> SEQUENCE: 205

Met Arg Ala Trp Ile Phe Phe Leu Leu Cys Leu Ala Gly Arg Ala Leu
1               5                   10                  15

Ala Asp Val Val Met Thr Gln Ser Pro Leu Ser Leu Pro Val Thr Leu
                20                  25                  30

Gly Gln Pro Ala Ser Ile Ser Cys Arg Ser Ser Gln Ser Ile Val His
            35                  40                  45

Ser Asn Gly Asn Thr Tyr Leu Glu Trp Tyr Gln Gln Arg Pro Gly Gln
        50                  55                  60

Ser Pro Arg Leu Leu Ile Tyr Lys Ile Ser Asn Arg Phe Ser Gly Val
65                  70                  75                  80

Pro Asp Arg Phe Ser Gly Ser Gly Ser Gly Thr Asp Phe Thr Leu Lys

```
                85                  90                  95
Ile Ser Arg Val Glu Ala Glu Asp Val Gly Val Tyr Tyr Cys Phe Gln
            100                 105                 110

Gly Ser His Val Pro Arg Thr Phe Gly Gly Gly Thr Lys Leu Glu Ile
        115                 120                 125

Lys Arg
    130

<210> SEQ ID NO 206
<211> LENGTH: 153
<212> TYPE: PRT
<213> ORGANISM: Artificial Sequence
<220> FEATURE:
<223> OTHER INFORMATION: synthetic sequence

<400> SEQUENCE: 206

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Asp Asp Thr Ala Val
            100                 105                 110

Tyr Tyr Cys Ala Lys Ala Pro Gly Pro Met Val Arg Gly Val Ile Pro
        115                 120                 125

Asp Ile Trp Gly Gln Gly Thr Met Val Thr Val Ser Ser Gly Ser Ala
    130                 135                 140

Ser Ala Pro Thr Leu Phe Pro Leu Ala
145                 150

<210> SEQ ID NO 207
<211> LENGTH: 153
<212> TYPE: PRT
<213> ORGANISM: Artificial Sequence
<220> FEATURE:
<223> OTHER INFORMATION: synthetic sequence

<400> SEQUENCE: 207

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Ala Met His Trp Val Arg Gln Ala Pro Gly Lys Gly Leu
    50                  55                  60

Glu Trp Val Ala Val Ile Ser Tyr Asp Gly Asn Asn Lys Tyr Tyr Ala
65                  70                  75                  80

Asp Ser Val Lys Gly Arg Phe Thr Ile Ser Arg Asp Asn Phe Lys Asn
                85                  90                  95
```

```
Thr Leu Tyr Leu Gln Met Asn Ser Leu Arg Ala Asp Asp Thr Ala Val
            100                 105                 110

Tyr Tyr Cys Ala Lys Ala Pro Gly Ser Met Val Arg Gly Val Ile Pro
        115                 120                 125

Asp Ile Trp Gly Gln Gly Thr Met Val Thr Val Ser Ser Gly Ser Ala
    130                 135                 140

Ser Ala Pro Thr Leu Phe Pro Leu Ala
145                 150

<210> SEQ ID NO 208
<211> LENGTH: 153
<212> TYPE: PRT
<213> ORGANISM: Artificial Sequence
<220> FEATURE:
<223> OTHER INFORMATION: synthetic sequence

<400> SEQUENCE: 208

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Val Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Asn Asn
                85                  90                  95

Thr Leu Tyr Leu Gln Met Asn Ser Leu Arg Ala Asp Asp Thr Ala Val
            100                 105                 110

Tyr Tyr Cys Ala Lys Ala Pro Gly Pro Met Val Arg Gly Val Ile Pro
        115                 120                 125

Asp Ile Trp Gly Gln Gly Thr Met Val Thr Val Ser Ser Gly Ser Ala
    130                 135                 140

Ser Ala Pro Thr Leu Phe Pro Leu Ala
145                 150

<210> SEQ ID NO 209
<211> LENGTH: 153
<212> TYPE: PRT
<213> ORGANISM: Artificial Sequence
<220> FEATURE:
<223> OTHER INFORMATION: synthetic sequence

<400> SEQUENCE: 209

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Thr Pro Gly Lys Gly Leu
    50                  55                  60

Glu Trp Val Ala Val Ile Ser Tyr Asp Gly Arg Asn Lys Tyr Tyr Ala
65                  70                  75                  80

Asp Ser Val Lys Gly Arg Phe Thr Ile Ser Arg Asp Asn Phe Asn Asn
                85                  90                  95
```

```
Thr Leu Tyr Leu Gln Met Asn Ser Leu Arg Ala Asp Asp Thr Ala Val
                100                 105                 110

Tyr Tyr Cys Ala Lys Ala Pro Gly Pro Met Val Arg Gly Val Ile Pro
            115                 120                 125

Asp Ile Trp Gly Gln Gly Thr Met Val Thr Val Ser Ser Gly Ser Ala
        130                 135                 140

Ser Ala Pro Thr Leu Phe Pro Leu Ala
145                 150

<210> SEQ ID NO 210
<211> LENGTH: 153
<212> TYPE: PRT
<213> ORGANISM: Artificial Sequence
<220> FEATURE:
<223> OTHER INFORMATION: synthetic sequence

<400> SEQUENCE: 210

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Asn Tyr Val Met His Trp Val Arg Gln Thr Pro Gly Lys Gly Leu
        50                  55                  60

Glu Trp Val Ala Val Ile Ser Tyr Asp Gly Arg Asn Lys Tyr Tyr Ala
65                  70                  75                  80

Asp Ser Val Lys Gly Arg Phe Thr Ile Ser Arg Asp Asn Phe Asn Asn
                85                  90                  95

Thr Leu Tyr Leu Gln Met Asn Ser Leu Arg Ala Asp Asp Thr Ala Val
                100                 105                 110

Tyr Tyr Cys Ala Lys Ala Pro Gly Ser Met Val Arg Gly Val Ile Pro
            115                 120                 125

Asp Ile Trp Gly Gln Gly Thr Met Val Thr Val Ser Ser Gly Ser Ala
        130                 135                 140

Ser Ala Pro Thr Leu Phe Pro Leu Ala
145                 150

<210> SEQ ID NO 211
<211> LENGTH: 153
<212> TYPE: PRT
<213> ORGANISM: Artificial Sequence
<220> FEATURE:
<223> OTHER INFORMATION: synthetic sequence

<400> SEQUENCE: 211

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Asn Tyr Val Met His Trp Val Arg Gln Thr Pro Gly Lys Gly Leu
        50                  55                  60

Glu Trp Val Ala Val Ile Ser Tyr Asp Gly Arg Asn Lys Tyr Tyr Ala
65                  70                  75                  80

Asp Ser Val Lys Gly Arg Phe Thr Ile Ser Arg Asp Asn Ser Asn Asn
```

```
                85                  90                  95

Thr Leu Tyr Leu Gln Met Asn Ser Leu Arg Ala Glu Asp Thr Ala Val
                100                 105                 110

Tyr Tyr Cys Ala Lys Ala Pro Gly Pro Met Val Arg Gly Val Ile Pro
            115                 120                 125

Asp Ile Trp Gly Gln Gly Thr Met Val Thr Val Ser Ser Gly Ser Ala
130                 135                 140

Ser Ala Pro Thr Leu Phe Pro Leu Ala
145                 150

<210> SEQ ID NO 212
<211> LENGTH: 153
<212> TYPE: PRT
<213> ORGANISM: Artificial Sequence
<220> FEATURE:
<223> OTHER INFORMATION: synthetic sequence

<400> SEQUENCE: 212

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Asn Tyr Val Met His Trp Val Arg Gln Thr Pro Gly Lys Gly Leu
        50                  55                  60

Glu Trp Val Ala Val Ile Ser Tyr Asp Gly Arg Asn Lys Tyr Tyr Ala
65                  70                  75                  80

Asp Ser Val Lys Gly Arg Phe Thr Ile Ser Arg Asp Asn Ser Asn Asn
                85                  90                  95

Thr Leu Tyr Leu Gln Met Asn Ser Leu Arg Ala Asp Asp Thr Ala Val
                100                 105                 110

Tyr Tyr Cys Ala Lys Ala Pro Gly Ser Met Val Arg Gly Val Ile Pro
            115                 120                 125

Asp Ile Trp Gly Gln Gly Thr Met Val Thr Val Ser Ser Gly Ser Ala
130                 135                 140

Ser Ala Pro Thr Leu Phe Pro Leu Ala
145                 150

<210> SEQ ID NO 213
<211> LENGTH: 153
<212> TYPE: PRT
<213> ORGANISM: Artificial Sequence
<220> FEATURE:
<223> OTHER INFORMATION: synthetic sequence

<400> SEQUENCE: 213

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Asn Tyr Val Met His Trp Val Arg Gln Thr Pro Gly Lys Gly Leu
        50                  55                  60

Glu Trp Val Ala Val Ile Ser Tyr Asp Gly Arg Asn Lys Tyr Tyr Ala
65                  70                  75                  80
```

Asp Ser Val Lys Gly Arg Phe Thr Ile Ser Arg Asp Asn Phe Lys Asn
            85                  90                  95

Thr Leu Tyr Leu Gln Met Asn Ser Leu Arg Ala Asp Thr Ala Val
        100                 105                 110

Tyr Tyr Cys Ala Lys Ala Pro Gly Ser Met Val Arg Gly Val Ile Pro
        115                 120                 125

Asp Ile Trp Gly Gln Gly Thr Met Val Thr Val Ser Ser Gly Ser Ala
    130                 135                 140

Ser Ala Pro Thr Leu Phe Pro Leu Ala
145                 150

<210> SEQ ID NO 214
<211> LENGTH: 153
<212> TYPE: PRT
<213> ORGANISM: Artificial Sequence
<220> FEATURE:
<223> OTHER INFORMATION: synthetic sequence

<400> SEQUENCE: 214

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Asn Asn
            85                  90                  95

Thr Leu Tyr Leu Gln Met Asn Ser Leu Arg Ala Asp Asp Thr Ala Val
        100                 105                 110

Tyr Tyr Cys Ala Lys Ala Pro Gly Pro Met Val Arg Gly Val Ile Pro
        115                 120                 125

Asp Ile Trp Gly Gln Gly Thr Met Val Thr Val Ser Ser Gly Ser Ala
    130                 135                 140

Ser Ala Pro Thr Leu Phe Pro Leu Ala
145                 150

<210> SEQ ID NO 215
<211> LENGTH: 153
<212> TYPE: PRT
<213> ORGANISM: Artificial Sequence
<220> FEATURE:
<223> OTHER INFORMATION: synthetic sequence

<400> SEQUENCE: 215

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

```
Asp Ser Val Lys Gly Arg Phe Thr Ile Ser Arg Asp Asn Ser Asn Asn
                85                  90                  95

Thr Leu Tyr Leu Gln Met Asn Ser Leu Arg Ala Asp Asp Thr Ala Val
            100                 105                 110

Tyr Tyr Cys Ala Lys Ala Pro Gly Pro Met Val Arg Gly Val Ile Pro
        115                 120                 125

Asp Ile Trp Gly Gln Gly Thr Met Val Thr Val Ser Ser Gly Ser Ala
    130                 135                 140

Ser Ala Pro Thr Leu Phe Pro Leu Ala
145                 150

<210> SEQ ID NO 216
<211> LENGTH: 153
<212> TYPE: PRT
<213> ORGANISM: Artificial Sequence
<220> FEATURE:
<223> OTHER INFORMATION: synthetic sequence

<400> SEQUENCE: 216

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Thr Pro Gly Lys Gly Leu
    50                  55                  60

Glu Trp Val Ala Val Ile Ser Tyr Asp Gly Arg Asn Lys Tyr Tyr Ala
65                  70                  75                  80

Asp Ser Val Lys Gly Arg Phe Thr Ile Ser Arg Asp Asn Ser Asn Asn
                85                  90                  95

Thr Leu Tyr Leu Gln Met Asn Ser Leu Arg Ala Asp Asp Thr Ala Val
            100                 105                 110

Tyr Tyr Cys Ala Lys Ala Pro Gly Pro Met Val Arg Gly Val Ile Pro
        115                 120                 125

Asp Ile Trp Gly Gln Gly Thr Met Val Thr Val Ser Ser Gly Ser Ala
    130                 135                 140

Ser Ala Pro Thr Leu Phe Pro Leu Ala
145                 150

<210> SEQ ID NO 217
<211> LENGTH: 153
<212> TYPE: PRT
<213> ORGANISM: Artificial Sequence
<220> FEATURE:
<223> OTHER INFORMATION: synthetic sequence

<400> SEQUENCE: 217

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Thr Pro Gly Lys Gly Leu
    50                  55                  60

Glu Trp Val Ala Val Ile Ser Tyr Asp Gly Arg Asn Lys Tyr Tyr Ala
```

```
                65                  70                  75                  80
Asp Ser Val Lys Gly Arg Phe Thr Ile Ser Arg Asp Asn Ser Asn Asn
                    85                  90                  95

Thr Leu Tyr Leu Gln Met Asn Ser Leu Arg Ala Asp Asp Thr Ala Val
                100                 105                 110

Tyr Tyr Cys Ala Lys Ala Pro Gly Pro Met Val Arg Gly Val Ile Pro
            115                 120                 125

Asp Ile Trp Gly Gln Gly Thr Met Val Thr Val Ser Ser Gly Ser Ala
        130                 135                 140

Ser Ala Pro Thr Leu Phe Pro Leu Ala
145                 150

<210> SEQ ID NO 218
<211> LENGTH: 130
<212> TYPE: PRT
<213> ORGANISM: Artificial Sequence
<220> FEATURE:
<223> OTHER INFORMATION: synthetic sequence

<400> SEQUENCE: 218

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Gly
                100                 105                 110

Thr His Trp Pro Pro Tyr Thr Phe Gly Gln Gly Thr Lys Leu Glu Ile
            115                 120                 125

Lys Arg
    130

<210> SEQ ID NO 219
<211> LENGTH: 130
<212> TYPE: PRT
<213> ORGANISM: Artificial Sequence
<220> FEATURE:
<223> OTHER INFORMATION: synthetic sequence

<400> SEQUENCE: 219

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ile Ser Ser Tyr Leu Ala Trp Tyr Gln Gln Lys Pro Gly Gln Ala
    50                  55                  60

Pro Arg Leu Leu Ile Tyr Gly Ser Ser Arg Ala Thr Gly Ile Pro
65                  70                  75                  80
```

Asp Arg Phe Ser Gly Ser Gly Ser Gly Thr Asp Phe Thr Leu Thr Ile
            85                  90                  95

Ser Arg Leu Glu Pro Glu Asp Phe Ala Val Tyr Tyr Cys Met Gln Gly
            100                 105                 110

Thr His Trp Leu Pro Tyr Thr Phe Gly Gln Gly Thr Lys Leu Glu Ile
            115                 120                 125

Lys Arg
    130

<210> SEQ ID NO 220
<211> LENGTH: 130
<212> TYPE: PRT
<213> ORGANISM: Artificial Sequence
<220> FEATURE:
<223> OTHER INFORMATION: synthetic sequence

<400> SEQUENCE: 220

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Thr Ser Gln Ser
            35                  40                  45

Val Arg Ser Ser Tyr Leu Gly Trp Tyr Gln Gln Lys Pro Gly Gln Val
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
            85                  90                  95

Ser Arg Leu Glu Pro Glu Asp Phe Ala Val Tyr Tyr Cys Met Gln Ala
            100                 105                 110

Thr His Trp Pro Pro Tyr Thr Phe Gly Gln Gly Thr Lys Leu Glu Ile
            115                 120                 125

Lys Arg
    130

<210> SEQ ID NO 221
<211> LENGTH: 130
<212> TYPE: PRT
<213> ORGANISM: Artificial Sequence
<220> FEATURE:
<223> OTHER INFORMATION: synthetic sequence

<400> SEQUENCE: 221

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Thr Ser Gln Ser
            35                  40                  45

Val Arg Ser Ser Tyr Leu Gly Trp Tyr Gln Gln Lys Pro Gly Gln Val
    50                  55                  60

Pro Arg Leu Leu Ile Tyr Gly Ser Ile Arg Ala Thr Gly Ile Pro
65                  70                  75                  80

Asp Arg Phe Ser Gly Ser Gly Ser Gly Thr Asp Phe Thr Leu Thr Ile
            85                  90                  95

Ser Arg Leu Glu Pro Glu Asp Phe Ala Val Tyr Tyr Cys Met Gln Ala
            100                 105                 110

Thr His Trp Pro Pro Tyr Thr Phe Gly Gln Gly Thr Lys Leu Glu Ile
        115                 120                 125

Lys Arg
    130

<210> SEQ ID NO 222
<211> LENGTH: 147
<212> TYPE: PRT
<213> ORGANISM: Artificial Sequence
<220> FEATURE:
<223> OTHER INFORMATION: synthetic sequence

<400> SEQUENCE: 222

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Thr Ser Gln Ser
        35                  40                  45

Val Arg Ser Ser Tyr Leu Gly Trp Tyr Gln Gln Lys Pro Gly Gln Val
    50                  55                  60

Pro Arg Leu Leu Ile Tyr Gly Thr Ser Ile Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Ala
            100                 105                 110

Thr His Trp Pro Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu
145

<210> SEQ ID NO 223
<211> LENGTH: 130
<212> TYPE: PRT
<213> ORGANISM: Artificial Sequence
<220> FEATURE:
<223> OTHER INFORMATION: synthetic sequence

<400> SEQUENCE: 223

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ile Ser Ser Tyr Leu Ala Trp Tyr Gln Gln Lys Pro Gly Gln Thr
    50                  55                  60

Pro Arg Leu Leu Ile Tyr Gly Thr Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Gly
            100                 105                 110

Thr His Trp Leu Pro Tyr Thr Phe Gly Gln Gly Thr Lys Leu Glu Ile

-continued

<210> SEQ ID NO 224
<211> LENGTH: 130
<212> TYPE: PRT
<213> ORGANISM: Artificial Sequence
<220> FEATURE:
<223> OTHER INFORMATION: synthetic sequence

<400> SEQUENCE: 224

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ile Ser Ser Tyr Leu Ala Trp Tyr Gln Gln Lys Pro Gly Gln Ala
    50                  55                  60

Pro Arg Leu Leu Ile Tyr Gly Thr Ser Ile Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Gly
            100                 105                 110

Thr His Trp Leu Pro Tyr Thr Phe Gly Gln Gly Thr Lys Leu Glu Ile
        115                 120                 125

Lys Arg
    130

<210> SEQ ID NO 225
<211> LENGTH: 130
<212> TYPE: PRT
<213> ORGANISM: Artificial Sequence
<220> FEATURE:
<223> OTHER INFORMATION: synthetic sequence

<400> SEQUENCE: 225

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Thr Ser Gln Ser
            35                  40                  45

Val Arg Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Ala
            100                 105                 110

Thr His Trp Pro Pro Tyr Thr Phe Gly Gln Gly Thr Lys Leu Glu Ile
        115                 120                 125

Lys Arg
    130

```
<210> SEQ ID NO 226
<211> LENGTH: 130
<212> TYPE: PRT
<213> ORGANISM: Artificial Sequence
<220> FEATURE:
<223> OTHER INFORMATION: synthetic sequence

<400> SEQUENCE: 226

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Thr Ser Gln Ser
            35                  40                  45

Val Arg Ser Ser Tyr Leu Gly Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Ala
            100                 105                 110

Thr His Trp Pro Pro Tyr Thr Phe Gly Gln Gly Thr Lys Leu Glu Ile
        115                 120                 125

Lys Arg
    130

<210> SEQ ID NO 227
<211> LENGTH: 130
<212> TYPE: PRT
<213> ORGANISM: Artificial Sequence
<220> FEATURE:
<223> OTHER INFORMATION: synthetic sequence

<400> SEQUENCE: 227

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Thr Ser Gln Ser
            35                  40                  45

Val Ser Ser Ser Tyr Leu Gly Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Ala
            100                 105                 110

Thr His Trp Pro Pro Tyr Thr Phe Gly Gln Gly Thr Lys Leu Glu Ile
        115                 120                 125

Lys Arg
    130

<210> SEQ ID NO 228
<211> LENGTH: 130
<212> TYPE: PRT
<213> ORGANISM: Artificial Sequence
```

<220> FEATURE:
<223> OTHER INFORMATION: synthetic sequence

<400> SEQUENCE: 228

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Thr Ser Gln Ser
            35                  40                  45

Val Ser Ser Ser Tyr Leu Gly Trp Tyr Gln Gln Lys Pro Gly Gln Val
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Ala
            100                 105                 110

Thr His Trp Pro Pro Tyr Thr Phe Gly Gln Gly Thr Lys Leu Glu Ile
        115                 120                 125

Lys Arg
    130

<210> SEQ ID NO 229
<211> LENGTH: 130
<212> TYPE: PRT
<213> ORGANISM: Artificial Sequence
<220> FEATURE:
<223> OTHER INFORMATION: synthetic sequence

<400> SEQUENCE: 229

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Thr Ser Gln Ser
            35                  40                  45

Val Ser Ser Ser Tyr Leu Ala Trp Tyr Gln Gln Lys Pro Gly Gln Val
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Ala
            100                 105                 110

Thr His Trp Pro Pro Tyr Thr Phe Gly Gln Gly Thr Lys Leu Glu Ile
        115                 120                 125

Lys Arg
    130

<210> SEQ ID NO 230
<211> LENGTH: 130
<212> TYPE: PRT
<213> ORGANISM: Artificial Sequence
<220> FEATURE:
<223> OTHER INFORMATION: synthetic sequence

<400> SEQUENCE: 230

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Thr Ser Gln Ser
            35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Ala
                100                 105                 110

Thr His Trp Pro Pro Tyr Thr Phe Gly Gln Gly Thr Lys Leu Glu Ile
            115                 120                 125

Lys Arg
    130

<210> SEQ ID NO 231
<211> LENGTH: 130
<212> TYPE: PRT
<213> ORGANISM: Artificial Sequence
<220> FEATURE:
<223> OTHER INFORMATION: synthetic sequence

<400> SEQUENCE: 231

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Met Gln Ala
                100                 105                 110

Thr His Trp Pro Pro Tyr Thr Phe Gly Gln Gly Thr Lys Leu Glu Ile
            115                 120                 125

Lys Arg
    130
```